(12) United States Patent
Barrett et al.

(10) Patent No.: US 11,331,597 B2
(45) Date of Patent: May 17, 2022

(54) CATION EXCHANGE MATERIALS FOR DIALYSIS SYSTEMS

(71) Applicant: Fresenius Medical Care Holdings, Inc., Waltham, MA (US)

(72) Inventors: Spencer Barrett, Oklahoma City, OK (US); Colin Kaufman, Waltham, MA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 159 days.

(21) Appl. No.: 16/532,161

(22) Filed: Aug. 5, 2019

(65) Prior Publication Data

US 2021/0039016 A1 Feb. 11, 2021

(51) Int. Cl.
*A61M 1/16* (2006.01)
*B01D 15/36* (2006.01)
(Continued)

(52) U.S. Cl.
CPC ......... *B01D 15/362* (2013.01); *A61M 1/1672* (2014.02); *A61M 1/1696* (2013.01);
(Continued)

(58) Field of Classification Search
CPC ... B01D 15/362; A61M 1/672; A61M 1/1696; B01J 47/014; B01J 47/024; B01J 39/02;
(Continued)

(56) References Cited

U.S. PATENT DOCUMENTS 3,485,763 A 12/1969 Lefevre et al.
3,669,878 A 6/1972 Marantz et al.
(Continued)

FOREIGN PATENT DOCUMENTS

AT 224087 11/1962
AU 2013273759 1/2014
(Continued)

OTHER PUBLICATIONS

Sigma-Aldrich, "Zirconium(IV) hydrogen phosphate". Accessed May 7, 2021.*
(Continued)

*Primary Examiner* — Benjamin L Lebron
(74) *Attorney, Agent, or Firm* — Fish & Richardson P.C.

(57) ABSTRACT

A sorbent cartridge device includes an ion-exchange material containing zirconium phosphate and no more than about 0.1 mg of leachable phosphate ions per about 1 g of the ion-exchange material. In one example, the cartridge also includes a phosphate-adsorbing material containing zirconium oxide. In this example, the weight ratio between zirconium phosphate and zirconium oxide in the cartridge is from about 10:1 to about 40:1. The zirconium phosphate may be alkaline zirconium phosphate prepared by a process including the following steps: (i) drying acid zirconium phosphate to obtain a dry acid zirconium phosphate; (ii) combining the dry acid zirconium phosphate with an aqueous solution to obtain an aqueous slurry; and (iii) combining the slurry with an alkali hydroxide to obtain the alkaline zirconium phosphate. During step (ii), any free phosphate ions in the dry acid zirconium phosphate leach out into the aqueous phase of the slurry.

20 Claims, 30 Drawing Sheets

(51) Int. Cl.
B01J 20/02 (2006.01)
B01J 20/08 (2006.01)
B01J 20/32 (2006.01)
B01J 39/02 (2006.01)
B01J 39/12 (2006.01)
B01J 47/014 (2017.01)
B01J 47/024 (2017.01)
C01B 25/37 (2006.01)
C01G 25/00 (2006.01)
B01J 20/28 (2006.01)
B01J 20/20 (2006.01)

(52) U.S. Cl.
CPC ....... *B01J 20/0211* (2013.01); *B01J 20/0292* (2013.01); *B01J 20/08* (2013.01); *B01J 20/28052* (2013.01); *B01J 20/3234* (2013.01); *B01J 39/02* (2013.01); *B01J 39/12* (2013.01); *B01J 47/014* (2017.01); *B01J 47/024* (2013.01); *C01B 25/372* (2013.01); *C01G 25/006* (2013.01); B01J 20/0277 (2013.01); B01J 20/20 (2013.01); B01J 2220/42 (2013.01); B01J 2220/62 (2013.01)

(58) Field of Classification Search
CPC .... B01J 39/12; B01J 20/0211; B01J 20/0277; B01J 20/0292; B01J 20/08; B01J 20/20; B01J 20/28052; B01J 20/3234; B01J 2220/42; B01J 2220/62; C01B 25/372; C01G 25/006
See application file for complete search history.

(56) References Cited

U.S. PATENT DOCUMENTS

| | | | |
|---|---|---|---|
| 4,025,608 A * | 5/1977 | Tawil | C01B 25/45 423/305 |
| 4,512,905 A | 4/1985 | Clearfield et al. | |
| 4,695,642 A * | 9/1987 | Derouane | B01J 29/82 556/14 |
| 7,033,498 B2 | 4/2006 | Wong | |
| 8,647,506 B2 | 2/2014 | Wong | |
| 8,758,626 B2 | 6/2014 | Wong | |
| 9,827,361 B2 | 11/2017 | Pudil et al. | |
| 9,962,477 B2 | 5/2018 | Slade | |
| 2002/0112609 A1 | 8/2002 | Wong | |
| 2003/0103888 A1 * | 6/2003 | Hai | B01J 20/0211 423/308 |
| 2004/0007532 A1 * | 1/2004 | Bortun | C01B 25/372 210/660 |
| 2004/0022717 A1 | 2/2004 | Wong | |
| 2006/0140840 A1 | 6/2006 | Wong | |
| 2010/0078387 A1 | 4/2010 | Wong | |
| 2010/0084330 A1 | 4/2010 | Wong | |
| 2012/0234762 A1 | 9/2012 | Wong | |
| 2013/0213891 A1 | 8/2013 | Karoor | |
| 2014/0217025 A1 | 8/2014 | Sandford | |
| 2014/0336568 A1 | 11/2014 | Wong | |
| 2015/0144539 A1 | 5/2015 | Pudil et al. | |
| 2016/0101225 A1 * | 4/2016 | Smith | A61M 1/1696 210/662 |
| 2017/0189598 A1 | 7/2017 | Slade | |
| 2018/0147558 A1 | 5/2018 | Hobot et al. | |
| 2018/0250461 A1 | 9/2018 | Gura | |

FOREIGN PATENT DOCUMENTS

| | | |
|---|---|---|
| FR | 2871810 | 12/2005 |
| GB | 1094972 | 12/1967 |
| GB | 1484642 | 9/1977 |
| IN | 216964 | 5/2006 |
| WO | WO 2009/064984 | 5/2009 |
| WO | WO 2011/017215 | 2/2011 |
| WO | WO 18/106185 | 6/2018 |
| WO | WO 2018/211389 | 11/2018 |

OTHER PUBLICATIONS

Cheng, Y., et al., "Mechanochemistry-based synthesis of highly crystalline gamma-zirconium phosphate for selective ion exchange", Inorganic Chemistry, 57, pp. 4370-4378. (Year: 2018).*

PCT International Search Report and Written Opinion in International Appln. No. PCT/US2020/044441, dated Nov. 12, 2020, 16 pages.

* cited by examiner

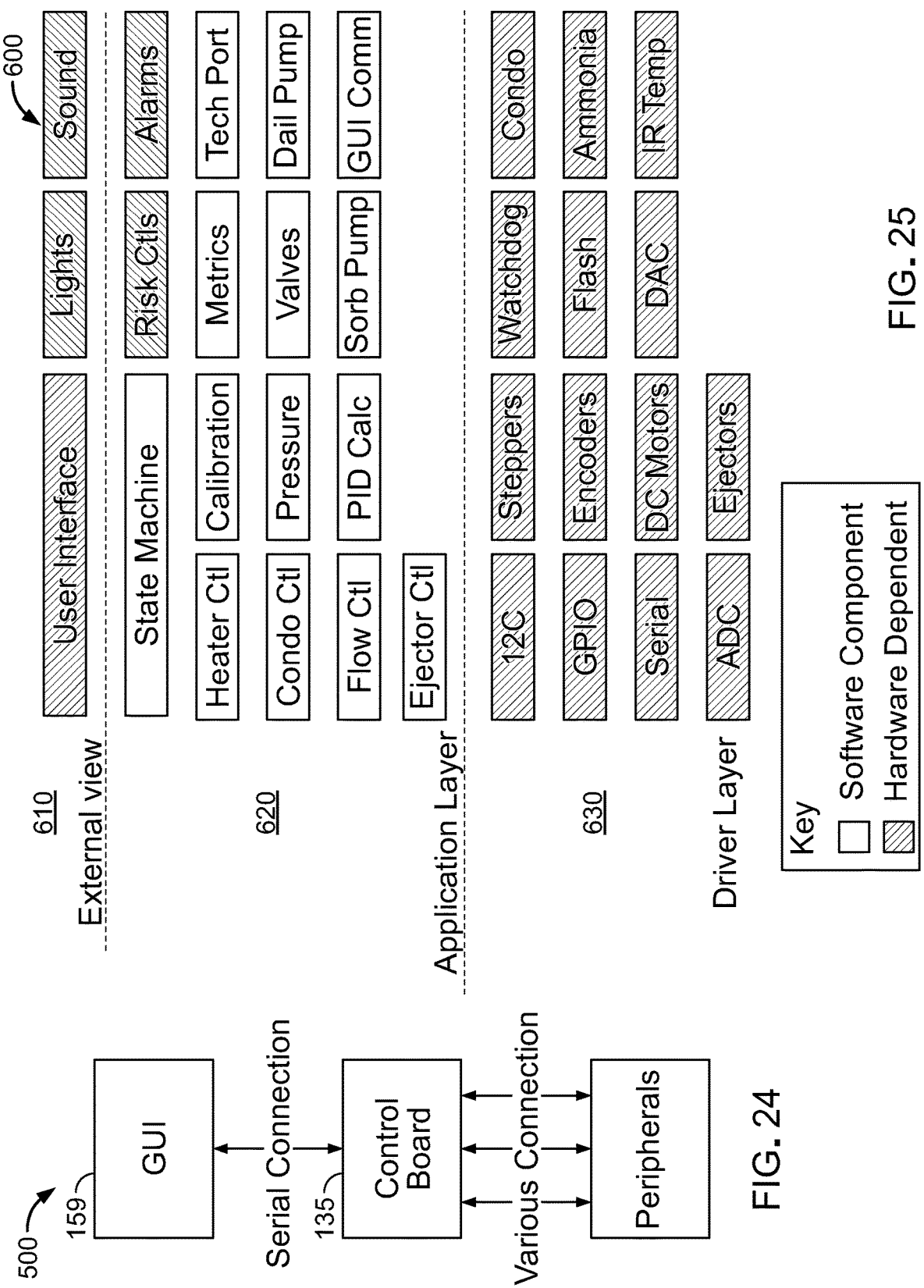

CATION EXCHANGE MATERIALS FOR DIALYSIS SYSTEMS

TECHNICAL FIELD

This disclosure relates to fluid conditioning systems for generating and conditioning dialysis fluid utilized by dialysis machines to carry out dialysis treatments. Such fluid conditioning systems can include sorbent systems containing ion-exchange materials for removing toxic substances (e.g., waste products) from the dialysis fluid.

BACKGROUND

Dialysis is a medical treatment that provides life-saving support to patients with insufficient renal function. The two principal dialysis methods are hemodialysis (HD) and peritoneal dialysis (PD). During HD, the patient's blood is passed through a dialyzer of a dialysis machine, while a dialysis solution (or, dialysate) is also passed through the dialyzer. A semi-permeable membrane in the dialyzer separates the blood from the dialysate and allows fluid exchanges to take place between the dialysate and the blood stream via diffusion, osmosis, and convective flow. These exchanges across the membrane result in the removal of waste products (e.g., such as solutes, like ammonia, urea and creatinine) from the blood. These exchanges also regulate the levels of other substances (e.g., sodium and water) in the blood. In this way, the dialysis machine acts as an artificial kidney for cleansing the blood.

During peritoneal dialysis ("PD"), the patient's peritoneal cavity is periodically infused with dialysate. The membranous lining of the patient's peritoneum acts as a natural semi-permeable membrane that allows diffusion and osmosis exchanges to take place between the solution and the blood stream. These exchanges across the patient's peritoneum result in the removal of waste products (e.g., such as solutes, like urea, ammonia, and creatinine) from the blood and regulate the levels of other substances (e.g., sodium and water) in the blood.

Some dialysis systems also include a sorbent cartridge for regenerating (e.g., recycling) dialysate, substantially reducing the amount of dialysate needed to effect a complete treatment session. For example, the sorbent cartridge can be designed to remove urea, ammonia, and ammonium salts from the dialysate. These sorbent cartridges often include ion-exchange materials containing insoluble inorganic phosphates (e.g., such as zirconium phosphate). Through an ion-exchange reaction, these inorganic phosphates can replace ammonium cations in the dialysate with hydrogen cations or sodium cations.

SUMMARY

This disclosure relates to fluid conditioning systems for generating and conditioning dialysis fluid utilized by dialysis machines to carry out dialysis treatments. In some embodiments, a fluid conditioning system includes a sorbent cartridge device including an ion-exchange material containing zirconium phosphate. Zirconium phosphate material prepared by conventional methods typically includes a high amount (e.g., about 2.5 mg/g) of leachable phosphates. These leachable phosphates often require the use a substantial amount of phosphate-adsorbing materials in conventional cartridges, which increases the cost of the cartridge and concomitantly increases the cost of the dialysis treatment. Advantageously, the zirconium phosphate material of the present disclosure contains almost no leachable phosphates (e.g., about 0.02 mg/g). Using this material in a sorbent cartridge allows a substantially-reduced amount of phosphate-adsorbing materials in the cartridge. This can reduce the overall cost of making and maintaining the dialysis system and can provide a higher degree of transportability compared to dialysis systems prepared with conventional zirconium phosphate materials. In addition, elevated serum phosphate in patients may lead to dangerous conditions, such as various bone pathologies, hypocalcemia, or hyperphosphatemia. Using sorbent cartridges with no leachable phosphates can decrease the likelihood of these dangerous conditions. Furthermore, the process of making nearly leachable-phosphate-free zirconium materials described herein is highly efficient, which can lead to $H_3PO_4$ savings (e.g., savings of nearly 40%), water savings (e.g., savings of over 80%), and an increase in the rate of production of zirconium phosphate product (e.g., an increase to over 65 kg/hr).

In a first general aspect, the present disclosure provides a sorbent cartridge device including an ion-exchange material containing zirconium phosphate and less than about 0.1 mg of leachable phosphate ions per about 1 g of the ion-exchange material.

In a second general aspect, the present disclosure provides a dialysis system including a dialysate generation machine; a pump adapted to move fluid through the dialysate generation machine; and a sorbent cartridge device fluidically connected to the dialysate generation machine, wherein the device includes an ion-exchange material containing zirconium phosphate and less than about 0.1 mg of leachable phosphate ions per about 1 g of the ion-exchange material.

In a third general aspect, the present disclosure provides a method of removing one or more substances from a spent dialysis solution, including passing the spent dialysis solution through a sorbent cartridge device including an ion-exchange material containing zirconium phosphate, wherein the device contains less than about 0.1 mg of leachable phosphate ions per about 1 g of the ion-exchange material.

In some embodiments, the one or more substances include ammonia or ammonium.

Embodiments of the first, second, and third general aspects may include one or more of the following features.

In some embodiments, the device includes from about 0.01 mg to about 0.03 mg of leachable phosphate ions per about 1 g of the ion-exchange material.

In some embodiments, the device includes a phosphate-adsorbing material containing a zirconium oxide.

In some embodiments, the weight ratio between the zirconium phosphate and the zirconium oxide in the device is from about 10:1 to about 40:1.

In some embodiments, the device includes a homogenous mixture of the zirconium phosphate and the zirconium oxide.

In some embodiments, the device includes a layer of the zirconium phosphate and a layer of the zirconium oxide.

In some embodiments, the device includes a urea-decomposing material.

In some embodiments, the urea-decomposing material is a urease enzyme.

In some embodiments, the device also includes alumina.

In some embodiments, the zirconium phosphate includes an alkaline zirconium phosphate.

In some embodiments, the alkaline zirconium phosphate is prepared by a process including the following steps: drying an acid zirconium phosphate to obtain a dry acid zirconium phosphate; combining the dry acid zirconium phosphate with an aqueous solution to obtain an aqueous slurry of the acid zirconium phosphate; and combining the slurry with an alkali hydroxide to obtain the alkaline zirconium phosphate.

In some embodiments, the device includes sodium content of about 60 mg to about 100 mg per about 1 g of the ion-exchange material; ammonia or ammonium adsorption capacity of about 15 mg to about 20 mg per about 1 g of the ion-exchange material; and a weight ratio of P to Zr from about 1.5:1 to about 2:1.

Other aspects, features, and advantages will be apparent from the description, the drawings, and the claims.

DESCRIPTION OF DRAWINGS

FIG. 24 provides a block diagram of a hardware system of the fluid conditioning system of FIG. 1.

FIG. 25 provides a block diagram of a software system of the fluid conditioning system of FIG. 1.

DETAILED DESCRIPTION

Figure 1:
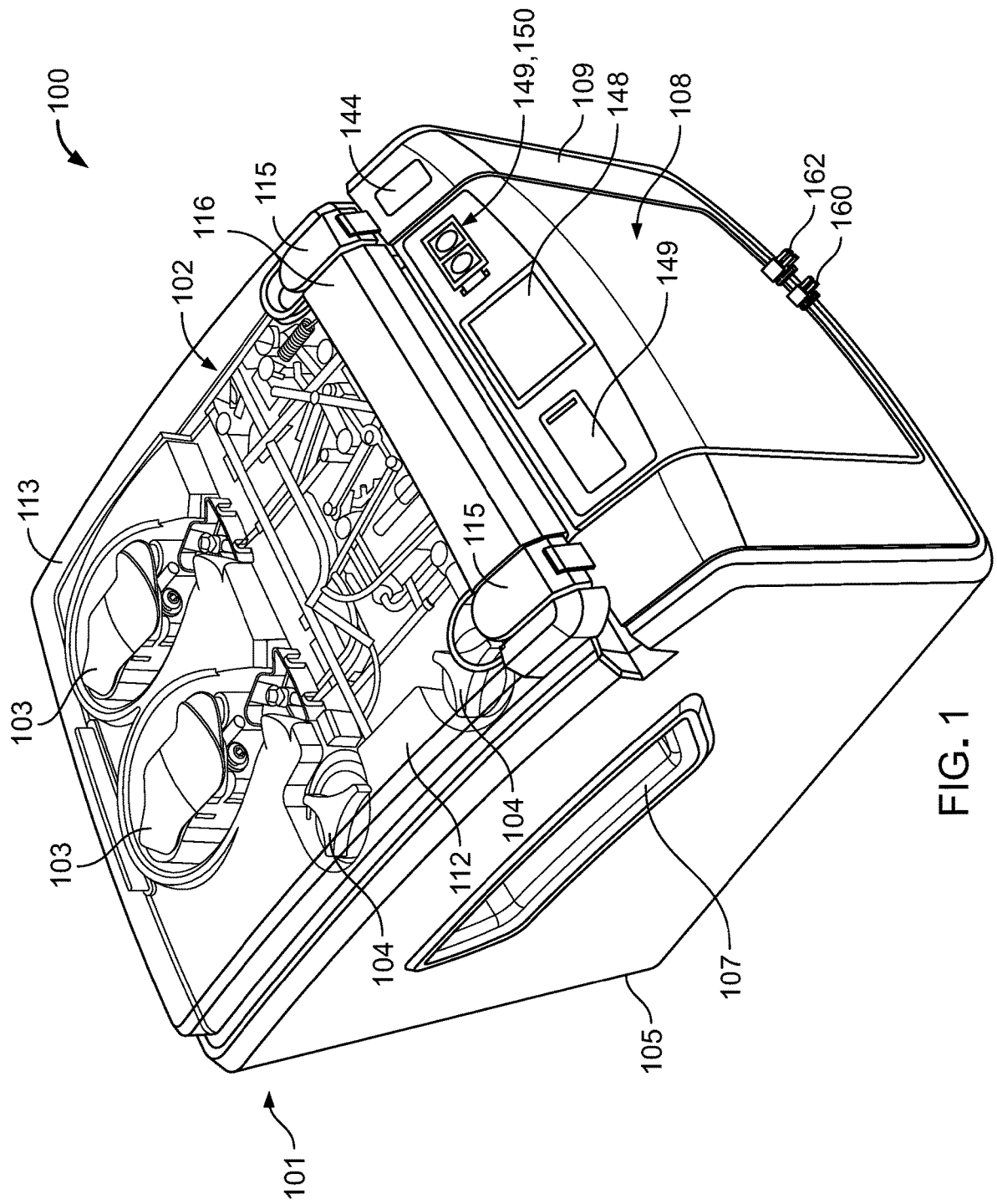
FIG. 1 is a perspective view of a fluid conditioning system that can cooperate with a dialysis system to carry out a fluid conditioning cycle that includes a dialysis treatment.
Figure 2:
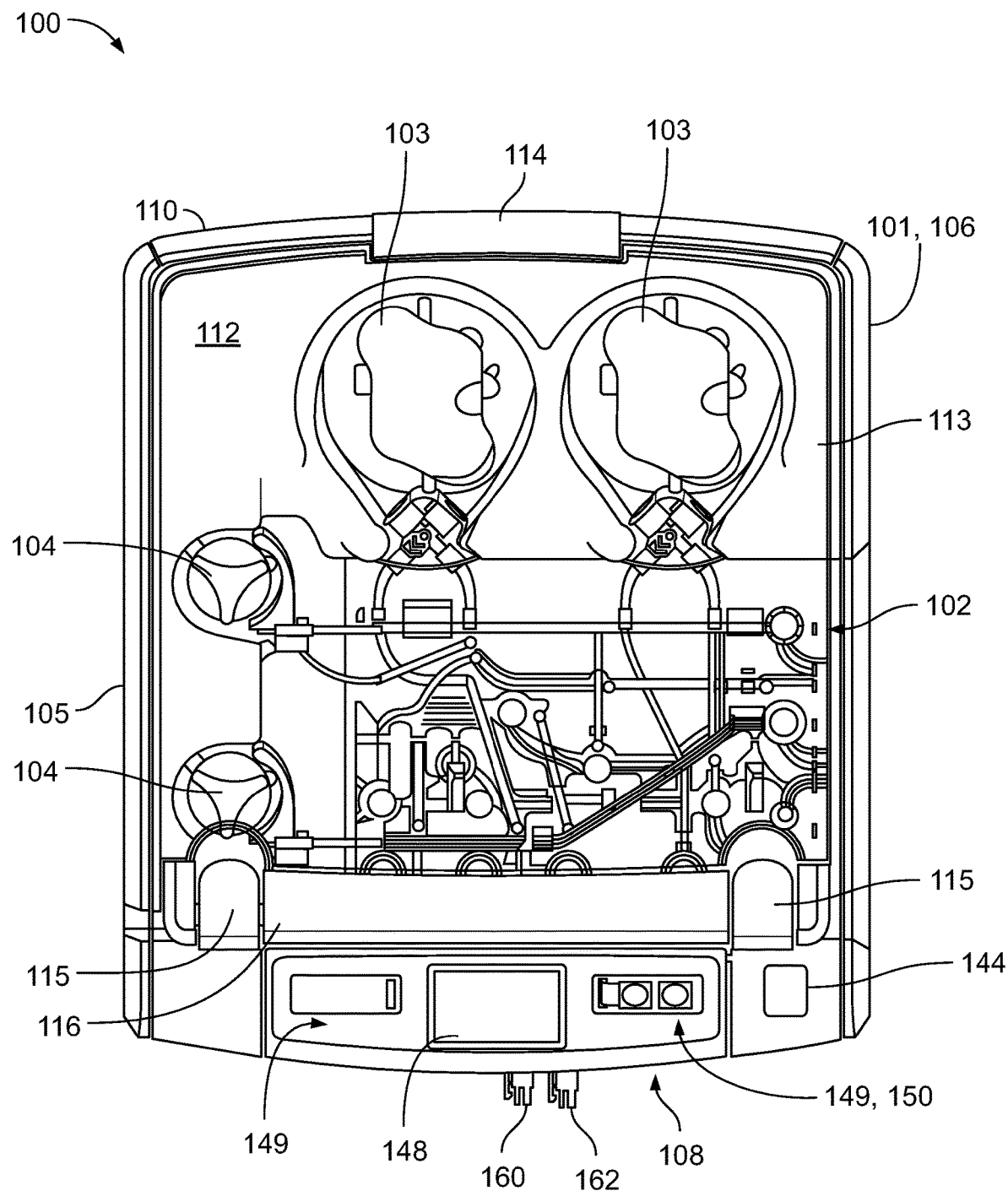
FIG. 2 is a top view of the fluid conditioning system of FIG. 1.
Figure 3:
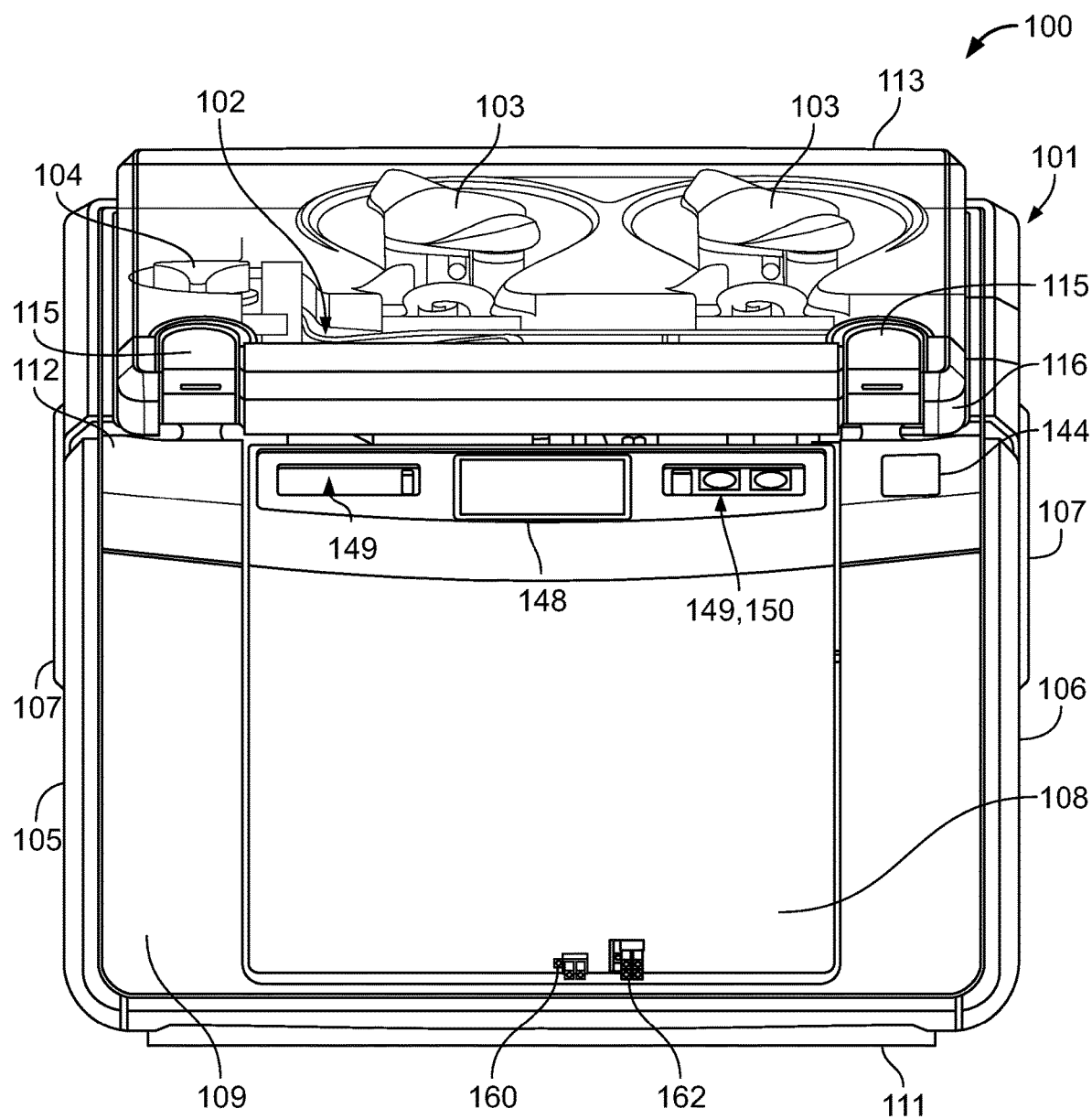
FIG. 3 is a front view of the fluid conditioning system of FIG. 1.
Figure 4:
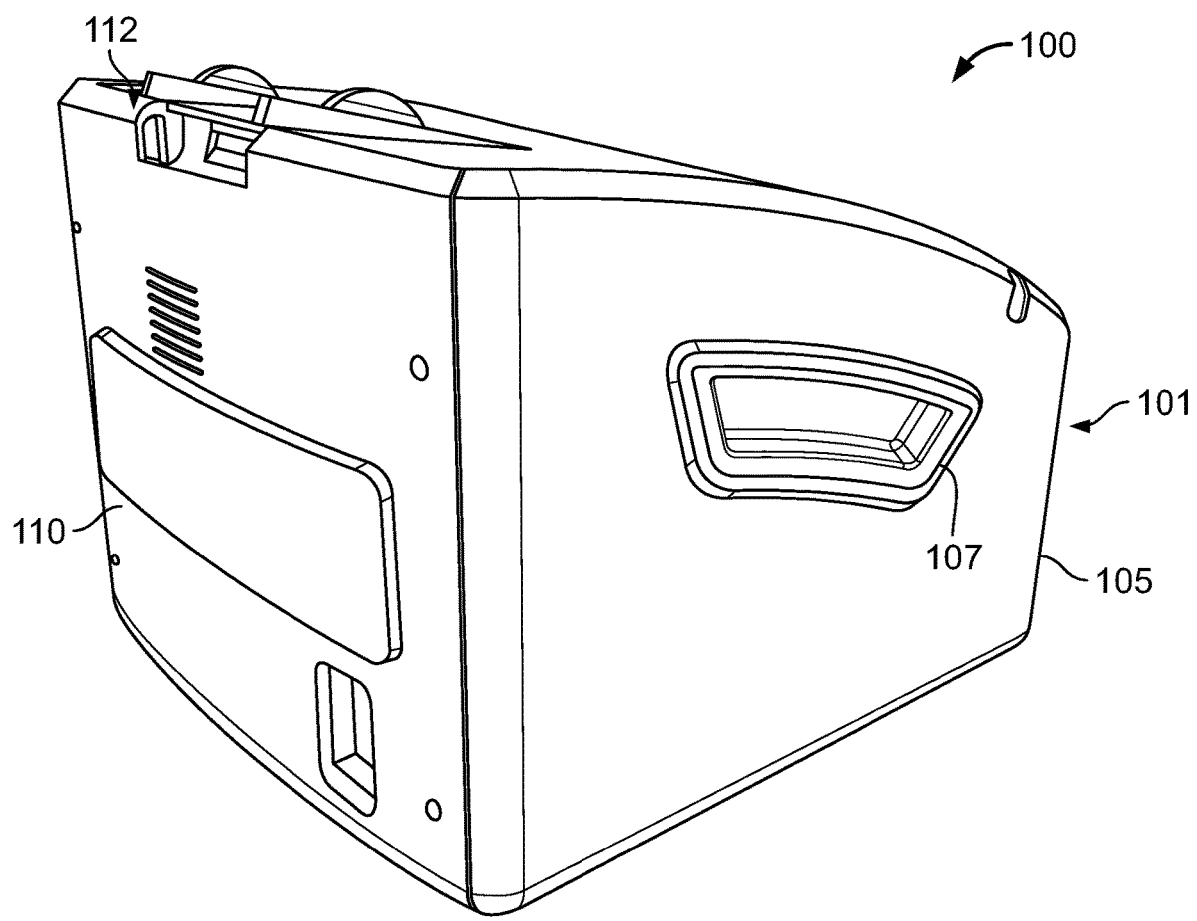
FIG. 4 is a rear view of the fluid conditioning system of FIG. 1.

FIGS. 1-4 illustrate a fluid conditioning system 100 that can be operated to prepare conditioned dialysate for use in a dialysis system. For example, the fluid conditioning system 100 can be fluidly communicated with the dialysis system to deliver "fresh" (e.g., cleaned, conditioned) dialysate to the dialysis system, collect "spent" (e.g., contaminated, unconditioned) dialysate from the dialysis system, and regenerate (e.g., cleanse) and condition the spent dialysate in a continuous fluid flow loop to recycle the spent dialysate. Example dialysis systems with which the fluid conditioning system 100 can be fluidly communicated include hemodialysis (HD) systems, peritoneal dialysis (PD) systems, hemofiltration (HF), hemodiafiltration (HDF) and other related systems. The fluid conditioning system 100 includes a housing 101 that contains or supports components of the fluid conditioning system 100, a fluid cassette 102 that includes multiple fluid lines defining various fluid pathways, two relatively high capacity pumps 103 that can circulate fluid within the fluid lines of the fluid cassette 102, and two relatively low capacity pumps 104 that can deliver (e.g., infuse) conditioning agents into the fluid circulating within the fluid lines of the fluid cassette 102. The fluid conditioning system 100 has a compact footprint that facilitates lifting and transport of the fluid conditioning system 100. For example, the fluid conditioning system 100 typically has a length of about 30 cm to about 50 cm, a width of about 30 cm to about 50 cm, a height of about 30 cm to about 50 cm, and a weight of about 15 kg to about 20 kg.

The housing 101 includes left and right side panels 105, 106, handles 107 positioned along the side panels 105, 106 for carrying the fluid conditioning system 100, a door assembly 108 that can be opened and closed to insert a heater bag, a front panel 109 to which the door assembly 108 is secured, rear and bottom panels 110, 111 that further enclose the interior components, an upper panel 112 that supports the fluid cassette 102 and the pumps 103, 104, and a cover 113 that protects the fluid cassette 102 and the pumps 103, 104. Example materials from which the exterior panels of the housing 101 may be made include plastics, such as acrylonitrile butadiene styrene (ABS) and polycarbonate blends, among others.

The cover 113 is typically made of ABS or polycarbonate and is transparent or translucent to allow visualization of the fluid cassette 102 and the pumps 103, 104. The cover 113 can be pivoted at a rear hinge 114 disposed along the upper panel 112 to open or close the cover 113. The upper panel 112 carries two latches 115 that can be closed upon a front edge 116 of the cover 113 to secure the cover 113 in a closed position. The latches 115 can also be pulled up and apart from the cover 113 to release the cover 113 from the closed position for accessing the fluid cassette 102 and the pumps 103, 104.

Figure 5:
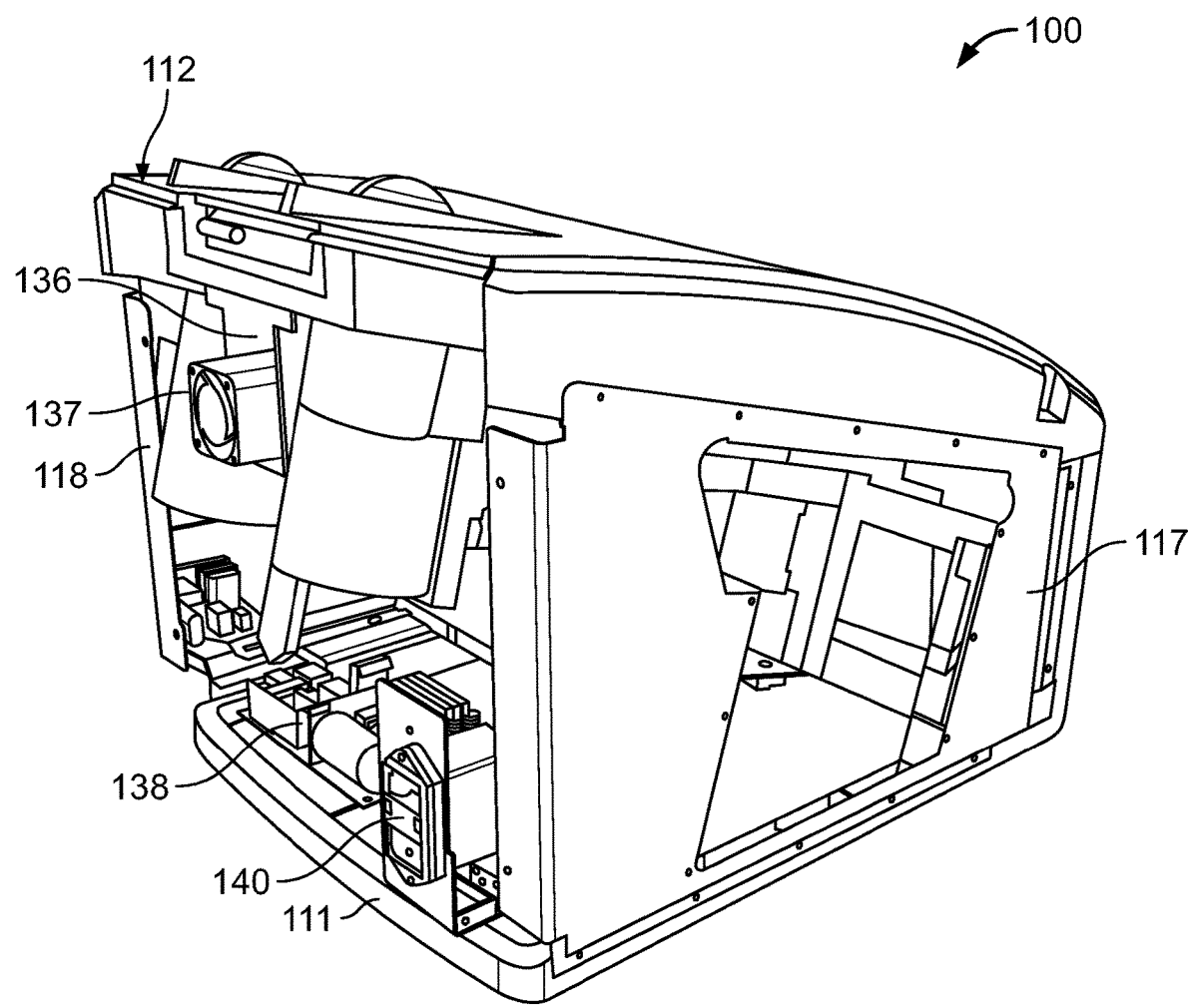
FIG. 5 is a rear view of the fluid conditioning system of FIG. 1, with certain exterior components omitted to expose certain interior components.

Referring to FIG. 5, the fluid conditioning system 100 also includes left and right side interior support frames 117, 118 to which the left side, right side, front, rear, bottom, and upper panels 105, 106, 109, 110, 111, 112 are attached. The interior support frames 117, 118 are typically formed from sheet metal.

Each pump 103, 104 is a peristaltic pump that includes multiple rollers positioned about the circumference of a rotatable frame (e.g., a motor) that carries a fluid line extending from the fluid cassette 102. As the rotatable frame is rotated, the rolling members apply pressure to the fluid line, thereby forcing fluid to flow through the fluid line.

Figure 6:
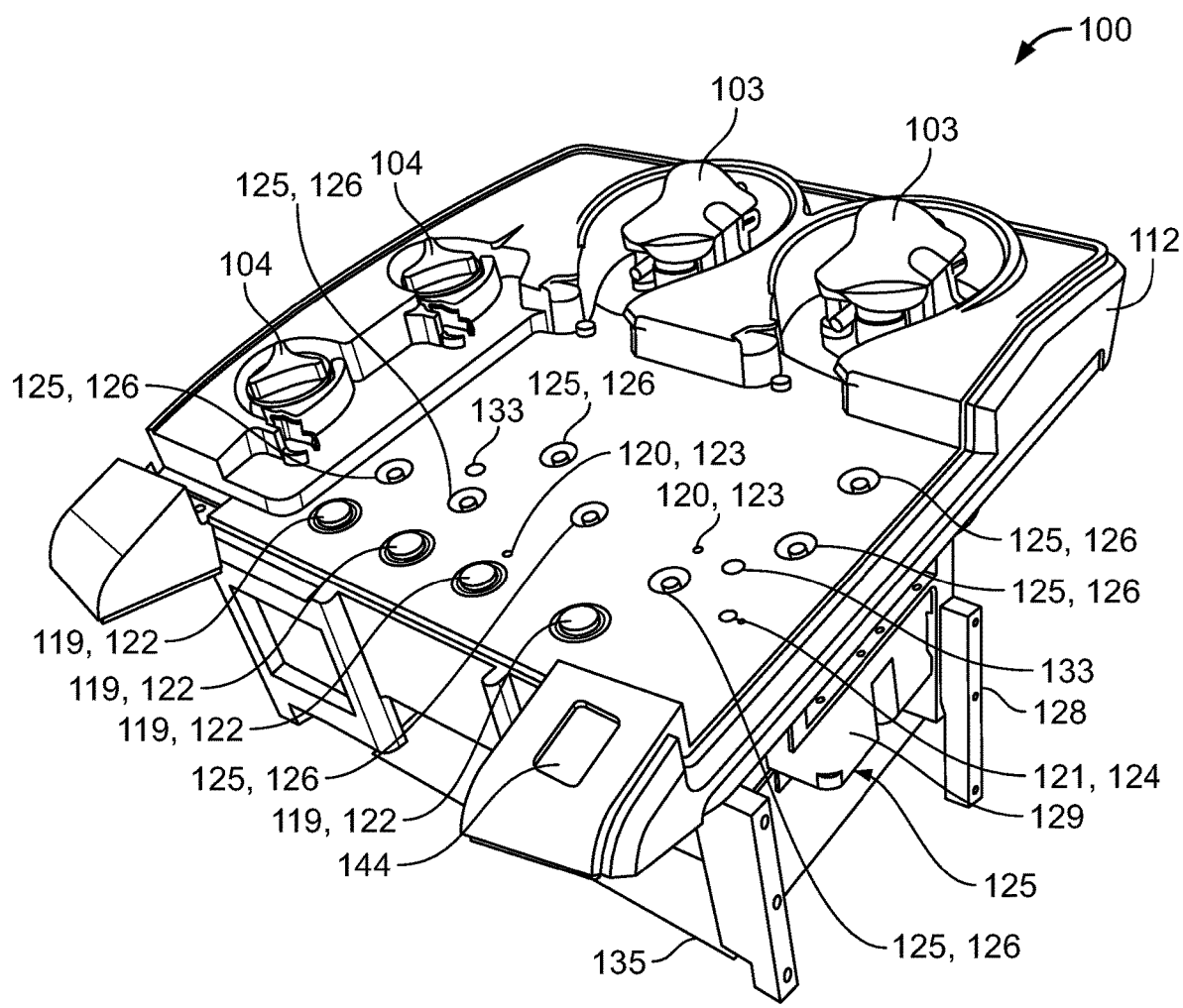
FIG. 6 is a perspective view of the fluid conditioning system of FIG. 1, with certain exterior components omitted to expose certain interior components.
Figure 7:
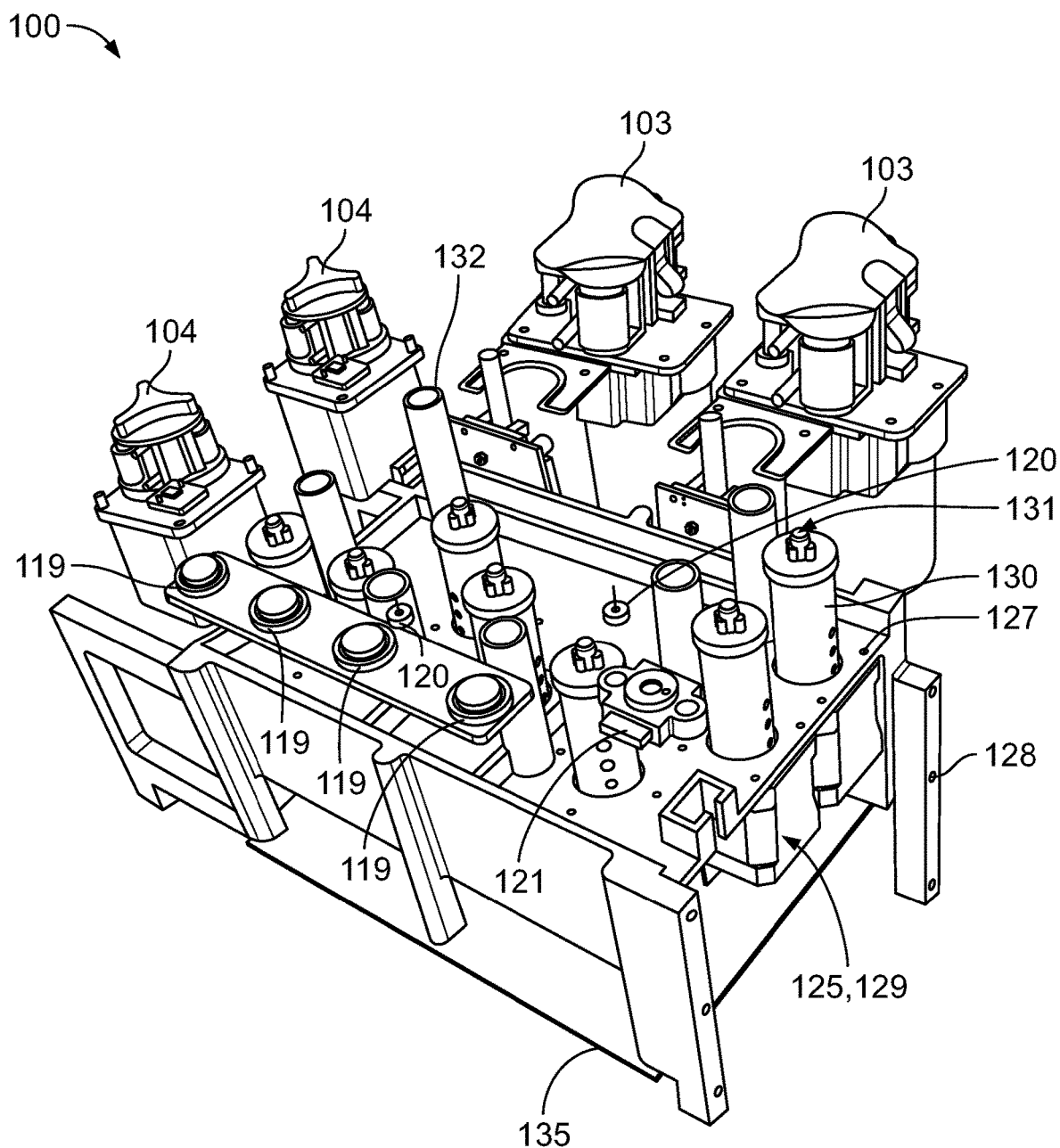
FIG. 7 is a perspective view of the fluid conditioning system of FIG. 1, with certain exterior components omitted to expose certain interior components.
Figure 8:
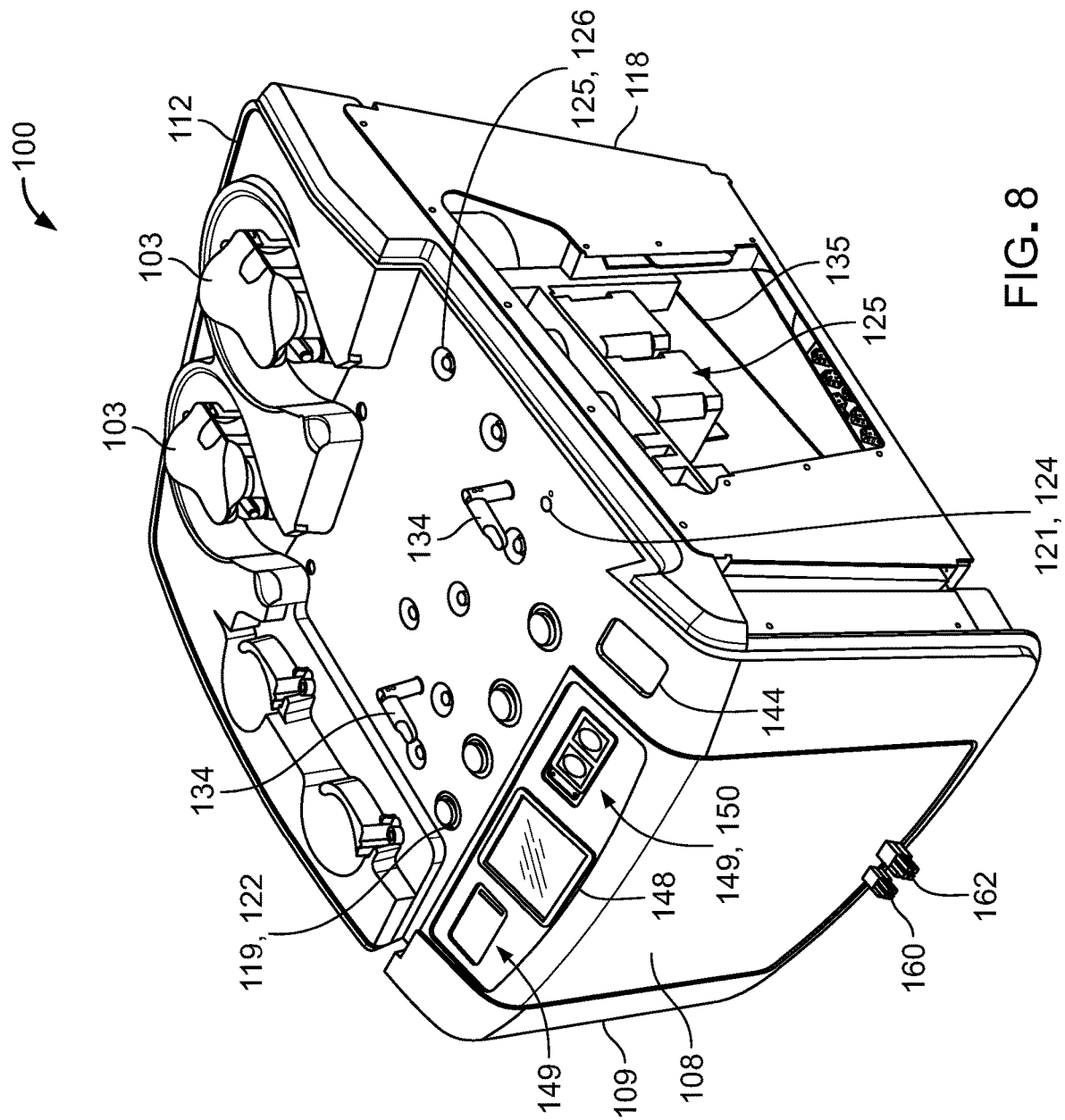
FIG. 8 is a perspective view of the fluid conditioning system of FIG. 1, with certain exterior components omitted to expose certain interior components.

FIGS. 6-8 illustrate certain interior components of the fluid conditioning system 100. For example, the fluid conditioning system 100 further includes multiple pressure transducers 119, two temperature sensors 120, and an ammonia detector 121 that are respectively positioned within holes 122, 123, 124 in the upper panel 112 for engagement with the fluid cassette 102. The pressure transducers 119 are embodied as thin, flexible membranes that contact corresponding thin, flexible membranes 164 within the fluid cassette 102 (refer to FIG. 15) for detecting fluid pressures within certain fluid pathways of the fluid cassette 102. The temperature sensors 120 are infrared (IR) sensors that detect temperatures of the dialysate flowing through certain points of the fluid pathways of the fluid cassette 102. The ammonia detector 121 is a red-green-blue (RGB) color sensor that can detect color changes on a paper strip within the fluid cassette 102 for determining a concentration of ammonium (e.g., which generates ammonia) within the dialysate flowing through a certain fluid pathway of the fluid cassette 102. The fluid conditioning system 100 also includes circuitry that acquires and conditions signals generated by conductivity sensors that are provided on the fluid cassette 102, which will be discussed in more detail below.

The fluid conditioning system 100 also includes multiple actuators 125 that are aligned with holes 126 in the upper panel 112 for respectively and selectively moving multiple valves of the fluid cassette 102. Each actuator 125 is mounted to a platform 127 of an internal frame 128 of the fluid conditioning system 100 and includes a motor 129 and a drive unit 130 that can be moved (e.g., rotated or otherwise manipulated) by the motor 129. The drive unit 130 is equipped with a coupling member 131 that is formed to engage a respective valve of the fluid cassette 102 such that movement of the drive unit 130 produces movement of the valve. The internal frame 128 also includes columnar support members 132 that support and locate the upper panel 112 of the housing 101. The upper panel 112 further defines holes 133 that are positioned and sized to receive locating pins 134 for appropriately positioning the fluid cassette 102 with respect to the upper panel 112. With the fluid cassette 102 in place, the locating pins 134 can be snapped down toward the upper panel 112 to lock the position of the fluid cassette 102. The fluid conditioning system 100 also includes a circuit board 135 equipped with electronics for operating the various electromechanical components of the fluid conditioning system 100. For example, the electronics execute codes for carrying out the various stages of a fluid conditioning cycle (as discussed below with reference to FIGS. 18-20), operating the pumps 103, 104, turning valves for the fluid cassette 102, processing sensor signals, operating the actuators 125, operating a heater assembly 151, and running control loops (e.g., control loops for regulating dialysate temperature, regulating pump speeds to achieve desired flow rates, regulating pump speeds to achieve desired dialysate chemical compositions, and ensuring device safety).

Referring again to FIG. 5, the fluid conditioning system 100 further includes a support bracket 136 and a fan 137 carried therein for cooling the circuit board 135 and other internal components of the fluid conditioning system 100. The fluid conditioning system 100 also includes a power supply 138, as well as a support bracket 139 that carries an A/C-in port 140.

Figure 10:
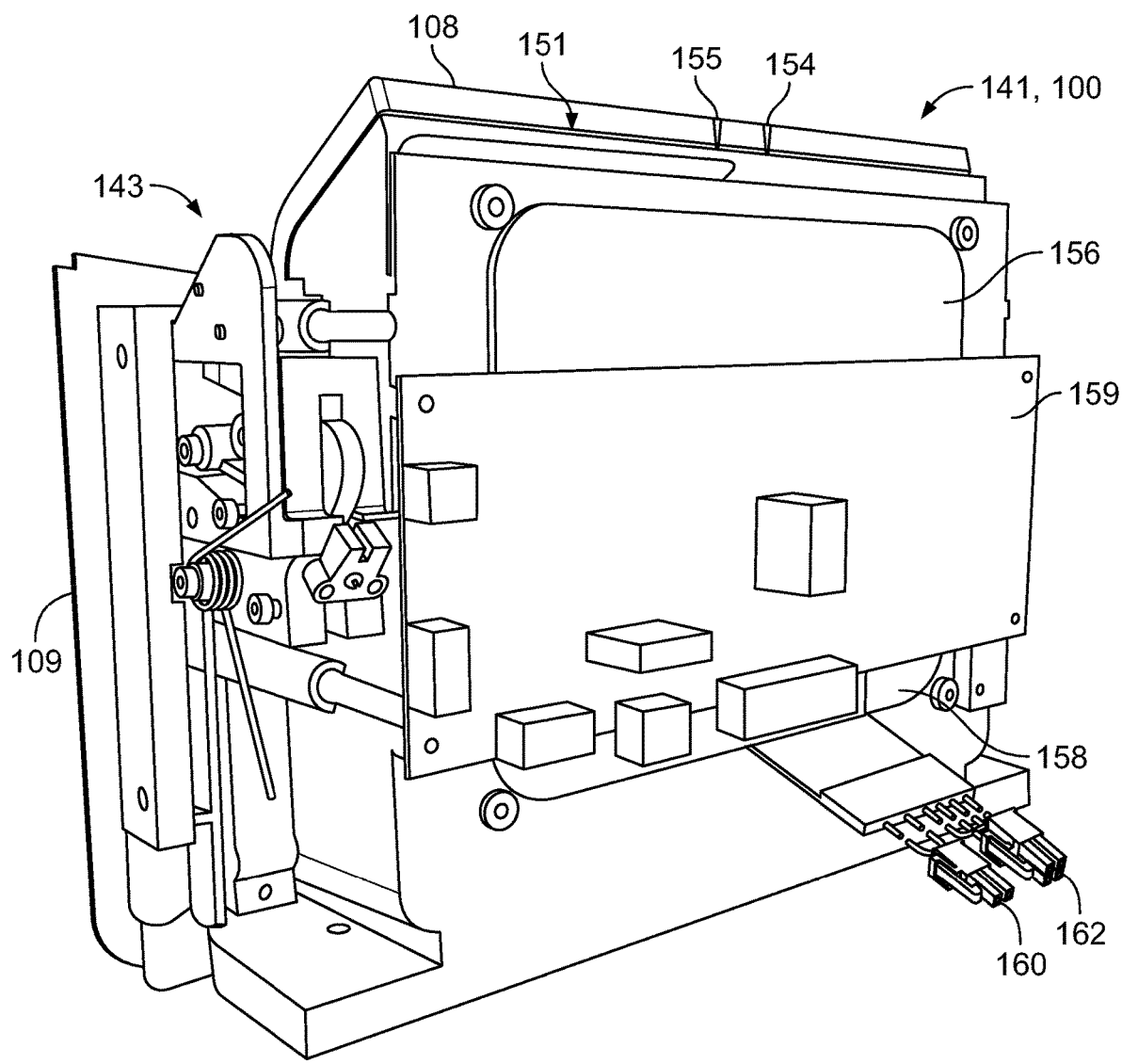
FIG. 10 is a rear perspective view of the front assembly of FIG. 9.
Figure 11:
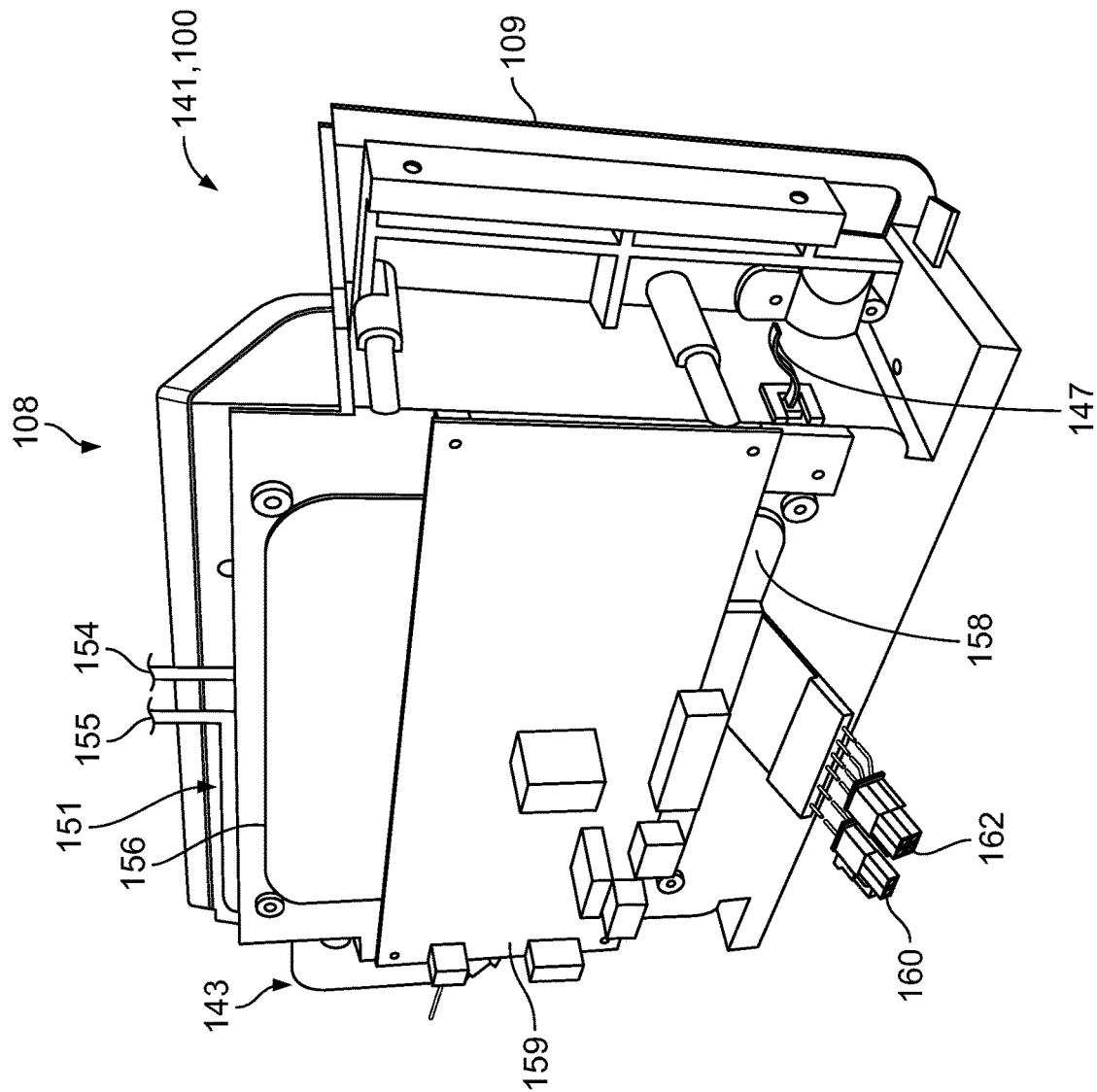
FIG. 11 is a rear perspective view of the front assembly of FIG. 9.
Figure 12:
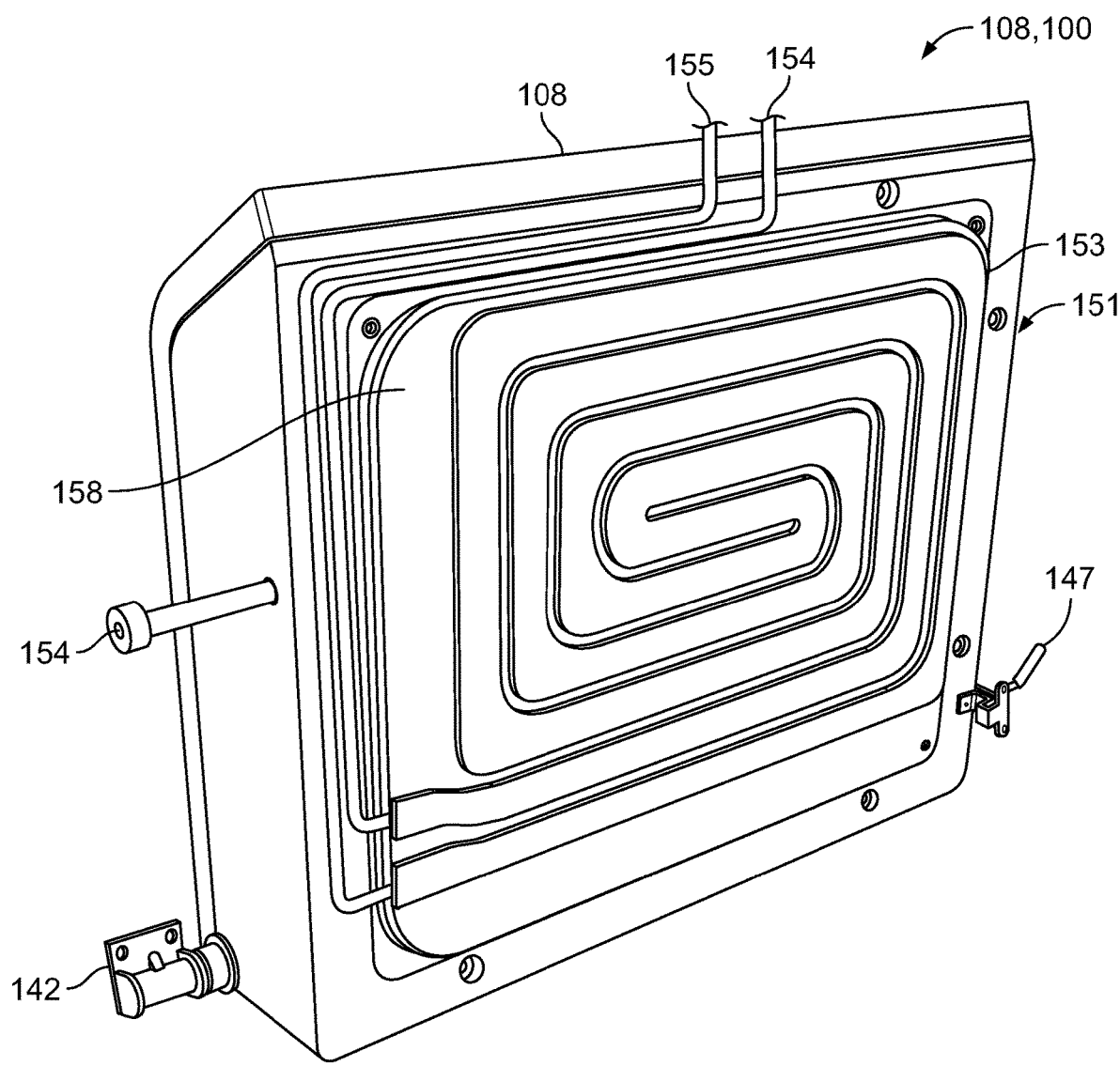
FIG. 12 is a rear perspective view of a heater bag of a door assembly of the front assembly of FIG. 9.

FIGS. 9-13 illustrate various views of a front assembly 141 of the fluid conditioning system 100. The front assembly 141 includes the door assembly 108 and the front panel 109 of the housing 101. The door assembly 108 is pivotable at hinges 142 with respect to the front panel 109 to allow loading of the heater bag 153 into the fluid conditioning system 100. The hinges 142 are friction hinges located along opposite sides of the door assembly 108, as shown in FIG. 12.

Figure 13:
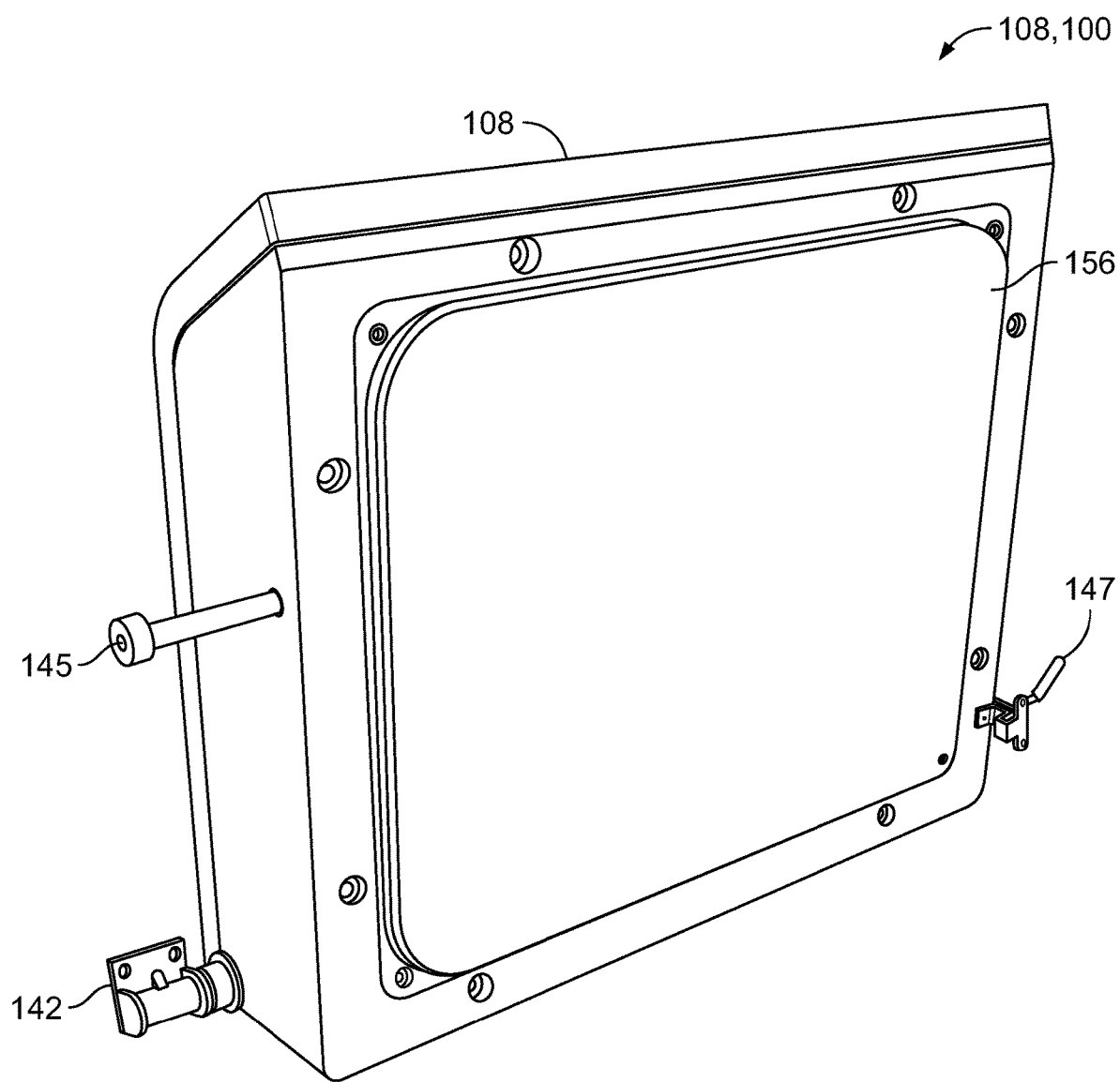
FIG. 13 is a rear perspective view of a heater plate of a door assembly of the front assembly of FIG. 9.

The front panel 109 carries a latch assembly 143 that cooperates with a button 144 carried by the upper panel 112 (shown in FIGS. 1-4) to releasably secure the door assembly 108 to the front panel 109 in a closed position. For example, depression of the button 144 adjusts the latch assembly 143 so that the door assembly 108 can be unlocked from a closed position and pivoted to an open position. The door assembly 108 can alternatively be pivoted inward from an open configuration until oppositely positioned screws 145 (e.g., shoulder screws, shown in FIG. 12) engage the latch assembly 131 to lock the door assembly 108 in the closed position. The latch assembly 131 has a contact switch for determining whether the door assembly 108 is open or closed. Referring particularly to FIGS. 11 and 13, the door assembly 108 includes an optical switch 147 that indicates whether or not the heater bag is inserted. In some embodiments, the fluid conditioning system 100 may be inoperable when the door assembly 108 is open.

Figure 9:
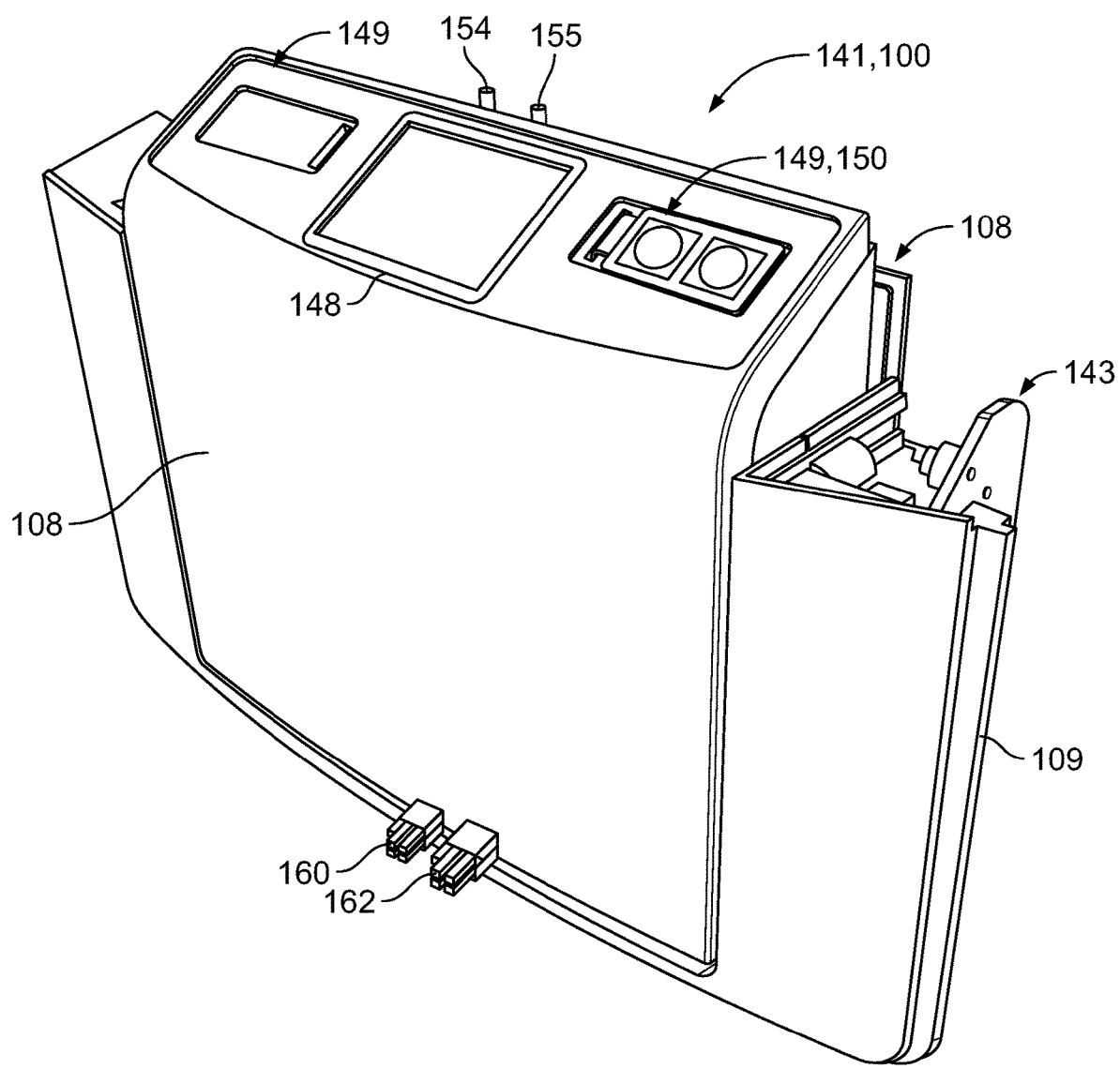
FIG. 9 is a perspective view of a front assembly of the fluid conditioning system of FIG. 1.

Referring particularly to FIG. 9, the door assembly 108 supports a display screen 148 (e.g., a touchscreen display) on which graphical user interfaces (GUIs) can be displayed and two control panels 149 that can each be equipped with selectors 150 (e.g., buttons) for providing inputs at the GUIs to operate the fluid conditioning system 100. Example parameters and processes that may be controlled by a user via the display screen 148 using the selectors 150 include starting and stopping a treatment, initiating a drain cycle, changing a flowrate, initiating a priming stage of a fluid conditioning cycle, initiating system preparation to start a fluid conditioning cycle, adjusting a temperature according to patient comfort, confirming correct placement of the fluid cassette 102, or confirming correct placement of fluid lines that interface with the pumps 103, 104.

Referring to FIGS. 10-13, the front assembly 141 includes components of a heater assembly 151 that is designed to regulate fluid temperatures of dialysate transported along the fluid pathways of the fluid cassette 102. Referring particularly to FIG. 12, the heater assembly 151 includes a heater bag 153 that is equipped with an input connection 154 and an output connection 155 that can interface with the fluid cassette 102 for allowing dialysate to circulate through the heater bag 153 to be warmed. The heater bag 153 is formed as a plastic channel that has a generally flat, collapsed shape when empty, that inflates upon filling with fluid, and that transfers heat from an exterior surface to dialysate flowing through the heater bag 153.

Figure 14:
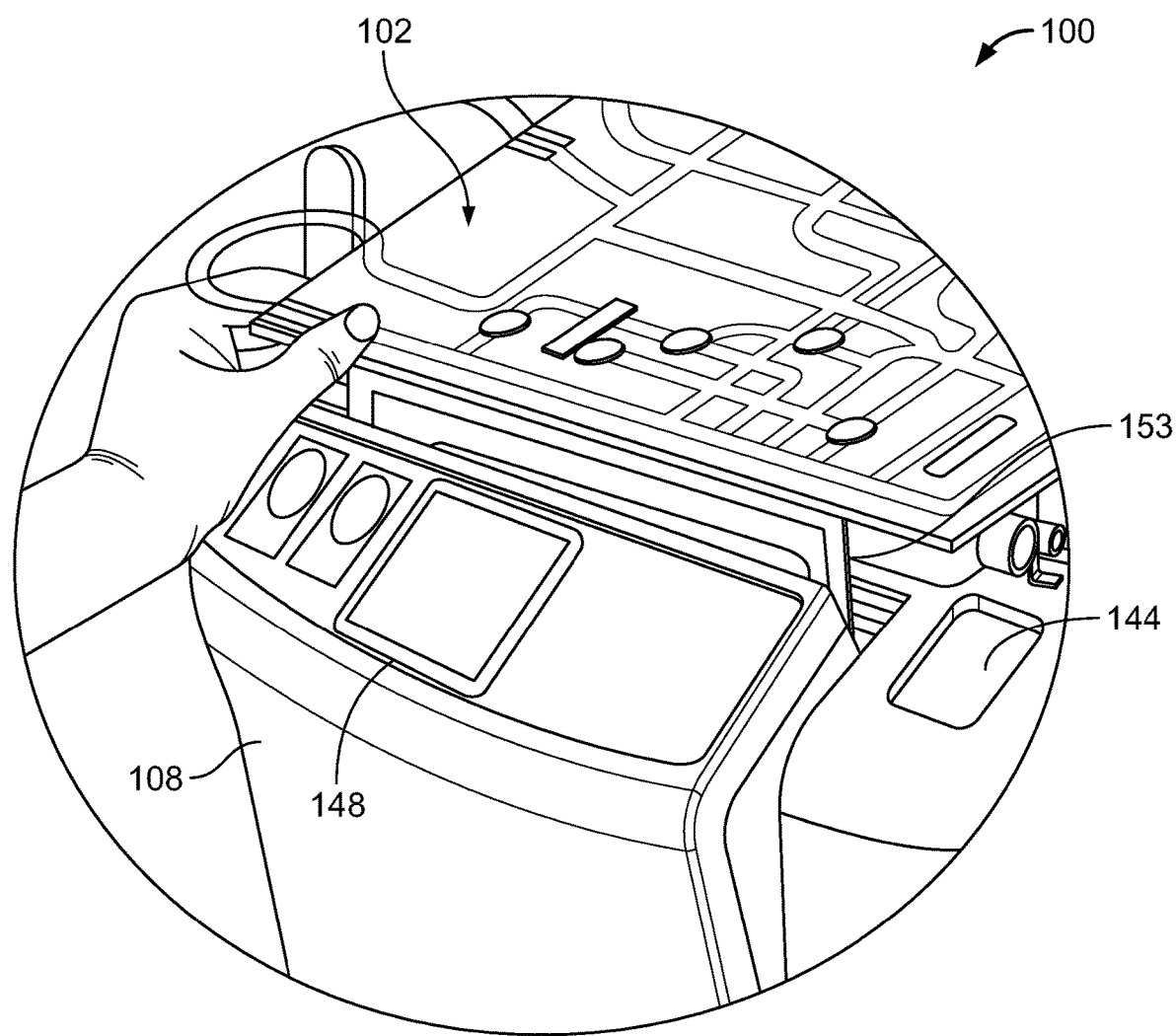
FIG. 14 is a perspective view illustrating installation of the heater bag of FIG. 12 and a fluid cassette of the fluid conditioning system of FIG. 1.

Referring particularly to FIG. 13, the heater assembly 151 further includes two plates 156 (e.g., aluminum plates) that position and support the heater bag 153 and that are heated for transferring heat to fluid within the heater bag 153. Referring particularly to FIG. 14, the heater bag 153 can be slid between heater plates 156 (not visible in FIG. 14) within the door assembly 108 when the door assembly 108 is in the open configuration. Referring particularly to FIGS. 10-12, the heater assembly 151 further includes one or more heating elements (for example, resistive type heating elements that are not shown) by which fluid in the heater bag 153 can be warmed and two insulation pads 158 disposed on opposite sides of the heater bag 153. The one or more heating elements are carried by or otherwise attached to one or both of the plates. The heater assembly 151 also includes a circuit board 159 that provides electronics for operating the heater assembly 151, a feed line 160 for each heating pad 156 that provides power, and thermocouple connections 162 for determining a temperature of the respective heating plates 156.

Figure 15:
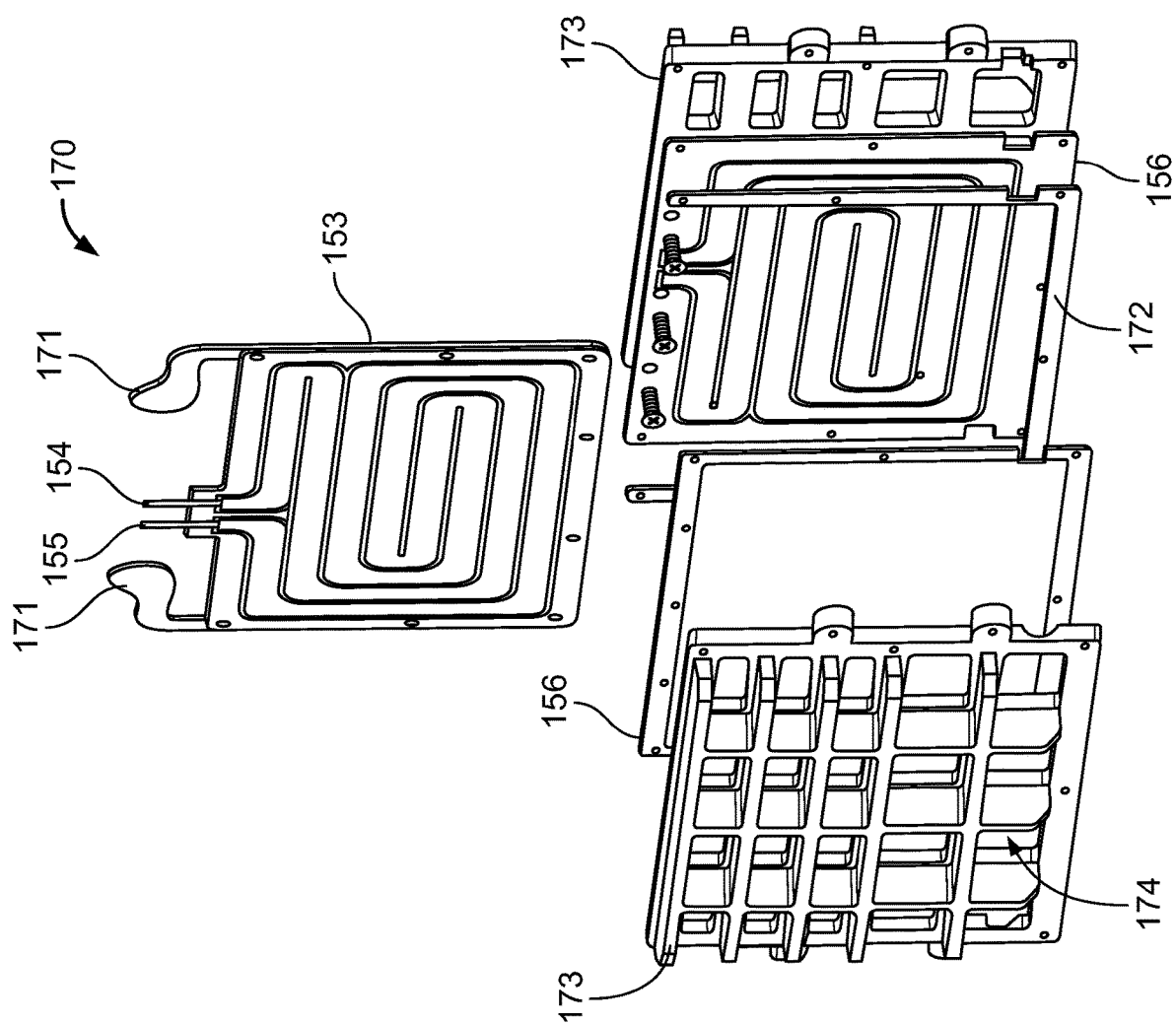
FIG. 15 is a perspective view of the fluid cassette of FIG. 14, along with the heater bag of FIG. 12.
Figure 16:
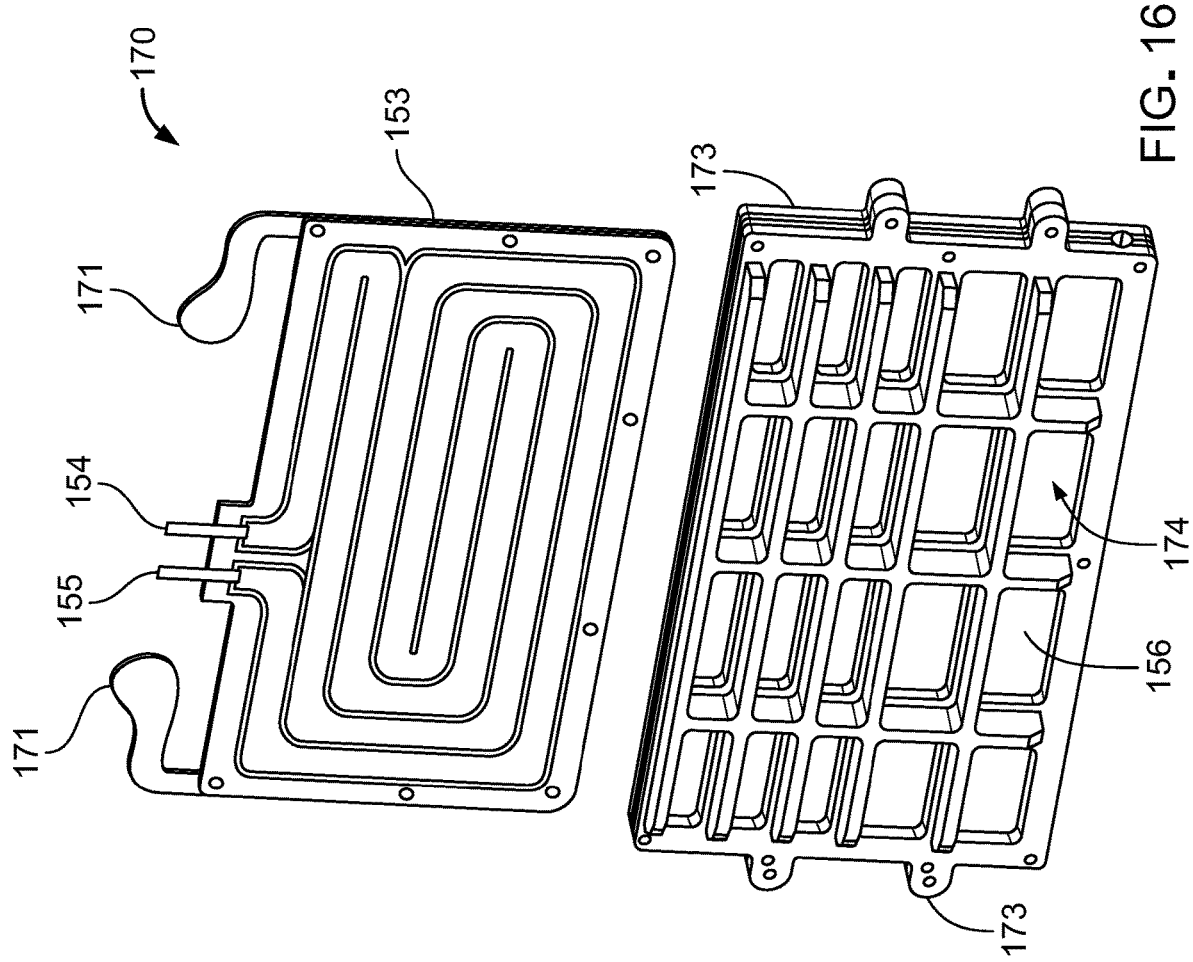
FIG. 16 is a full exploded perspective view of an embodiment of a heater assembly that may be included within the fluid conditioning system of FIG. 1.

FIGS. 15 and 16 illustrate another embodiment of a heater assembly 170 that may be included in the fluid conditioning system 100 instead of the heater assembly 151. The heater assembly 170 is similar in construction and function to the heater assembly 151 and accordingly includes the heater bag 153 sandwiched between the two heater plates 156. The heater assembly 170 further includes two handles 171 attached to the heater bag 153 for easy placement of the heater bag 153, a u-shaped heater frame 172 that supports the heater bag 153, and two support members 173 of a generally matrix construction that support the heater plates 156. The support members 173 further serve to insulate the heater bag 153 and the heater plates 156 from surrounding components via air gaps 174 defined by the matrix construction that are disposed between the heater plates 156 and such components.

Figure 17:
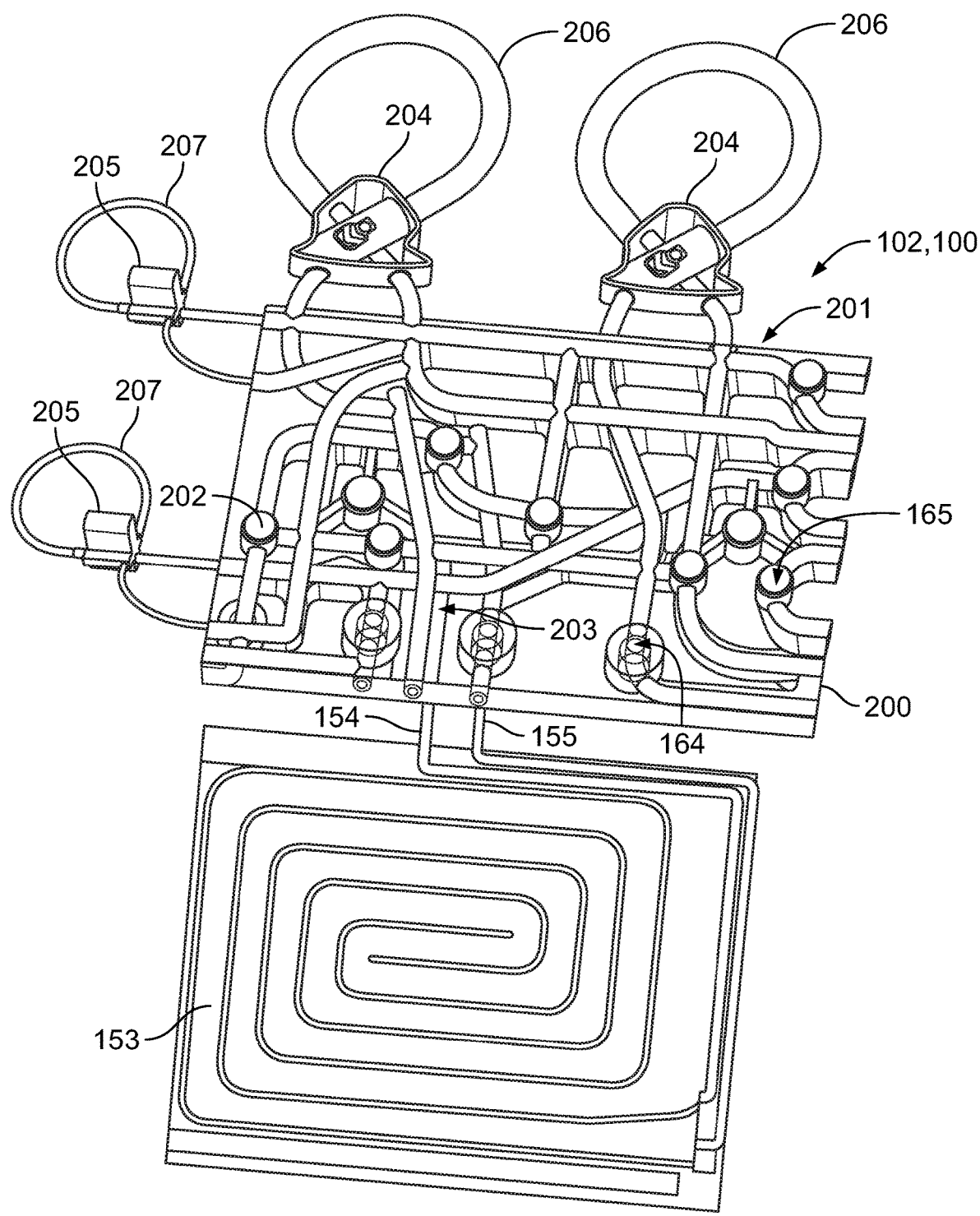
FIG. 17 is a partially exploded perspective view of the heater assembly of FIG. 16.

Referring to FIG. 17, the fluid cassette 102 is a single-use, disposable cartridge that includes a housing 200, multiple fluid lines 201 arranged within the housing 200, multiple valves 202 positioned along the fluid lines 201, two conductivity sensors 203 positioned along the fluid lines 201, an ammonia sensor 165 positioned along the fluid lines 201 for cooperation with the ammonia detector 121, two fluid line connectors (e.g., pump segment clips) 204, and two fluid line connectors (e.g., pump segment clips) 205. The fluid lines 201 cooperate with the heater bag 153 and a dialysis system to form a fluid circuit 350 for carrying out a fluid conditioning cycle. For example, the fluid lines 201 include ports to which the input and output connections 154, 155 of the heater bag 153 can be connected for providing fluid communication between the fluid lines 201 and the heater bag 153. The fluid line connectors 204 locate fluid line segments 206 about the high-capacity pumps 103, and the fluid line connectors 205 locate fluid line segments 207 about the low-capacity pumps 104. The fluid cassette 102 also includes additional fluid lines that extend from the fluid cassette 102 to various fluid containers, as illustrated in FIG. 19.

The valves 202 are three-way valves by which two alternative fluid pathways can be selected by a control system of the fluid conditioning system 100. Lower portions of the valves 202 are formed to engage with the coupling members 131 of the actuators 125 for movement of the valves 202. Example types of valves 202 that may be included in the fluid cassette 102 include rotary valves, push-pull valves, sliding valves, and shuttle valves.

Figure 18:
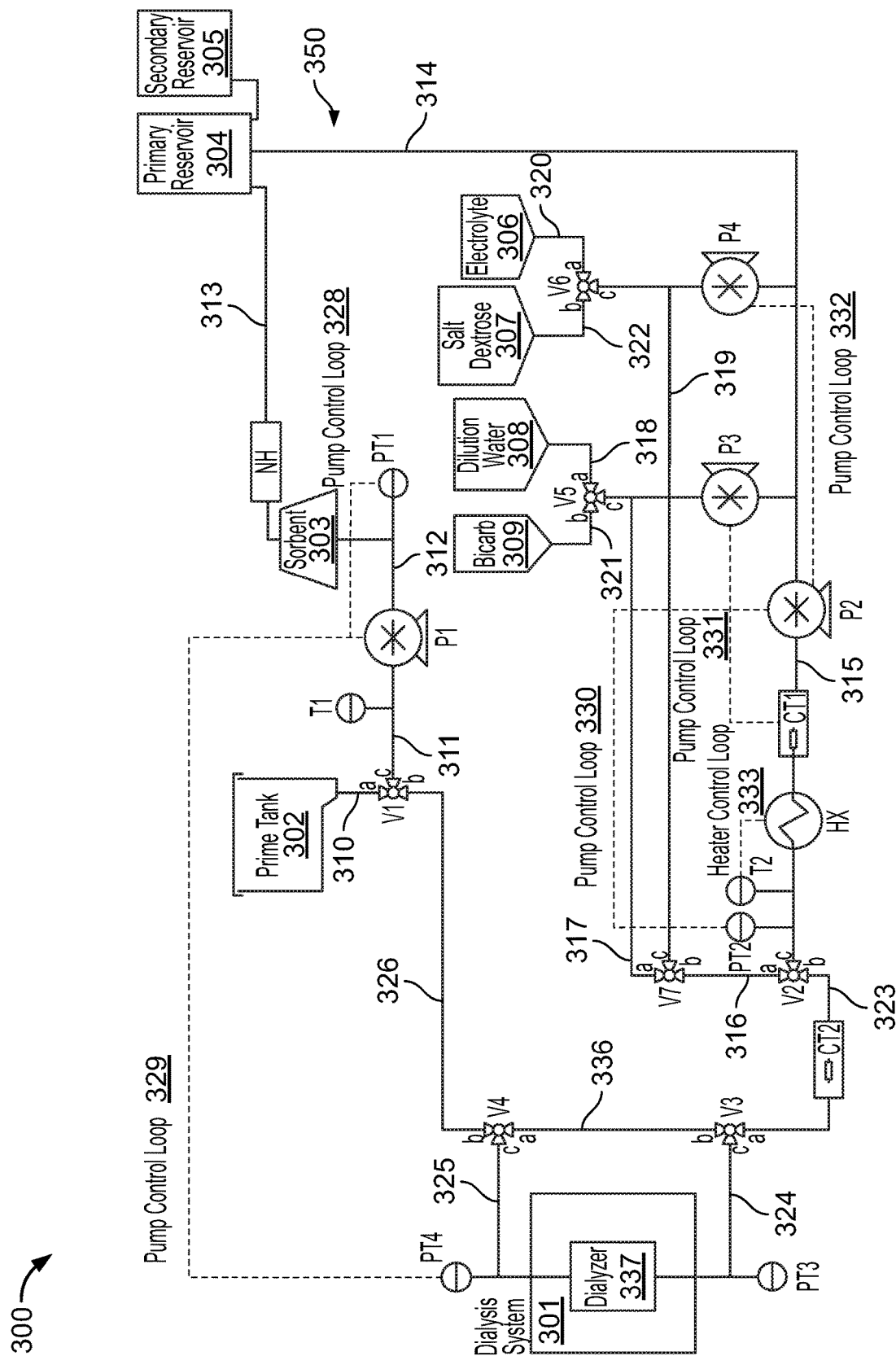
FIG. 18 provides an operational diagram by which the fluid conditioning system of FIG. 1 can cooperate with a dialysis system to form a fluid circuit for carrying out the fluid conditioning cycle.
Figure 19:
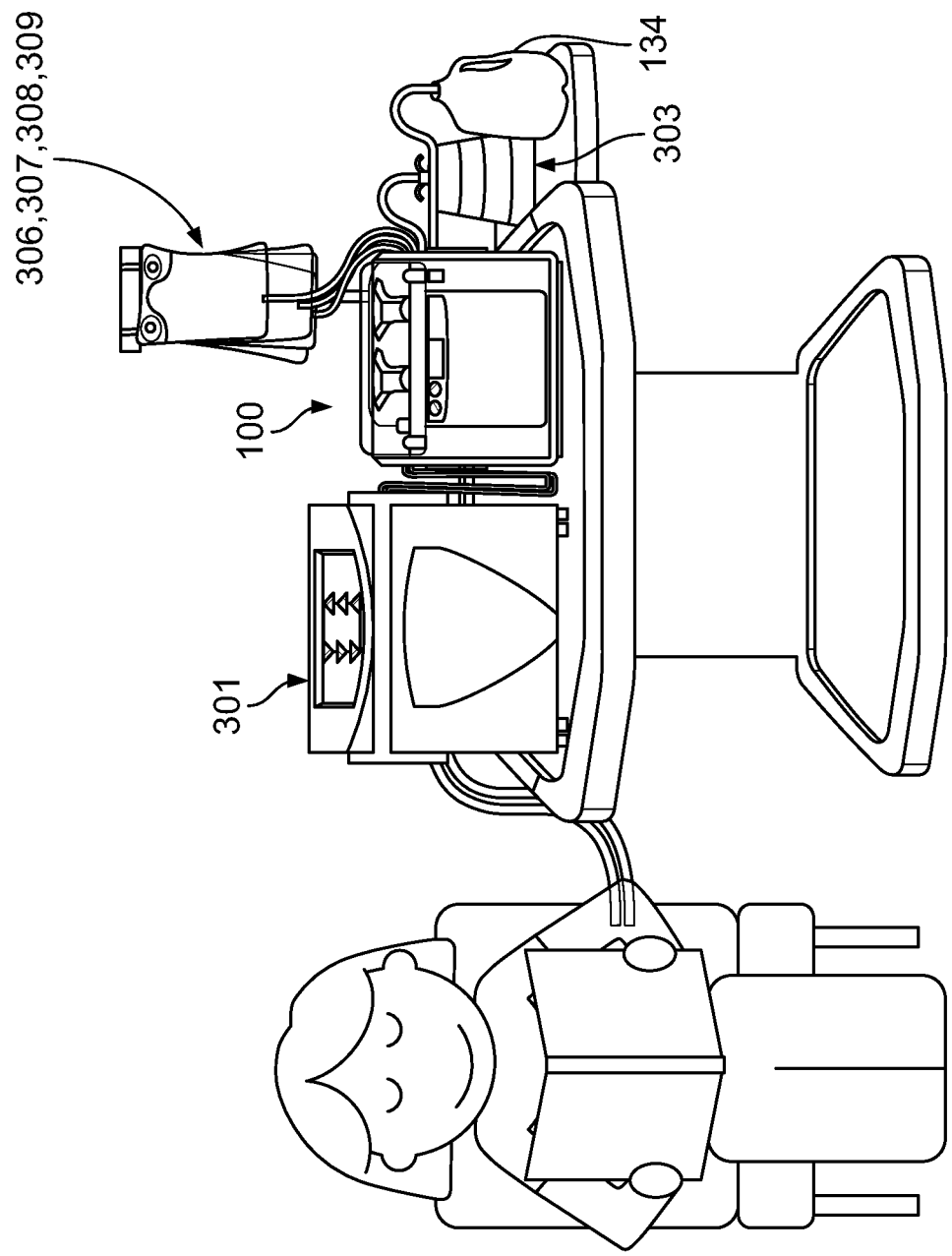
FIG. 19 illustrates an example setup of the fluid conditioning system of FIG. 1 with the dialysis system of FIG. 16.

FIG. 18 illustrates an operational diagram 300 by which the fluid conditioning system 100 can cooperate with a dialyzer 337 of a dialysis system 301 to form the fluid circuit 350 (indicated by solids lines) for carrying out a fluid conditioning cycle, while FIG. 19 illustrates an example setup of the fluid conditioning system 100 with the dialysis system 301. Example types of dialysis systems 301 that may be coupled to the fluid conditioning system 100 include HD systems, PD systems, HF systems, and HDF systems. The fluid circuit 350 incorporates components of the fluid cassette 102, as well as various other components of the fluid conditioning system 100.

For example, in addition to the components discussed above with respect to FIGS. 1-17, the fluid conditioning system 100 also includes a control system 161 (e.g., including the circuit boards 135, 159, as well as additional circuit boards for sensor circuitry) for controlling various operations of the fluid conditioning system 100 and several other, peripheral components positioned along the fluid circuit 350. These components include a prime tank 302 for collecting water to produce dialysate (e.g., sometimes referred to as dialysis fluid), a sorbent cartridge 303 for filtering tap water to provide purified water suitable for creating dialysate and for cleansing dialysate exiting the dialysis system 301, a primary reservoir 304 for collecting fluid (e.g., unconditioned water or dialysate) exiting the sorbent cartridge 303, a secondary reservoir 305 for collecting fluid that exceeds a capacity of the primary reservoir 304, a bag 306 for containing an electrolyte solution, a bag 307 for containing a salt-dextrose (SD) solution, a bag 308 for containing dilution water (DW), and a bag 309 for containing a bicarbonate (BC) solution that are positioned along the fluid flow path arrangement 300.

The bags 306, 307, 309 are pre-loaded with appropriate amounts of dry chemicals that can be dissolved in water to produce the electrolyte solution, the salt-dextrose solution, and the bicarbonate solution. Each bag 306, 307, 309 includes a nozzle that is designed to increase a velocity of a fluid flow entering the bag 306, 307, 309 and to create turbulence needed for adequate mixing and dissolution of the dry chemicals in water.

Table 1 lists approximate capacities of the various fluid-containing components of the fluid conditioning system 100.

TABLE 1

Capacities of fluid-containing components of the fluid conditioning system 100.

| Component | Capacity (mL) |
|---|---|
| Prime Tank (302) | 8,000 |
| Primary Reservoir (304) | 7,500 |
| Secondary Reservoir (305) | 4,500 |
| Electrolyte Bag (306) | 500 |
| Salt/Dextrose Bag (307) | 160 |
| Dilution Water Bag (308) | 4,000 |
| Bicarbonate Bag (309) | 1,000 |

The three-way valves 202 of the fluid cassette 102 are indicated as V1-V7 in the fluid circuit 350. Each valve includes three fluid ports (a), (b), (c) by which a flow path in the valve can be adjusted. A valve may be referred to as closed when two or three of its ports are closed and may be referred to as open when two or three of its ports are open. The valves include a prime valve V1, a dissolution valve V2, a bypass out valve V3, a bypass in valve V4, a BC/DW valve V5, an S/D/Electrolyte valve V6, and a fluid selector valve V7 The fluid lines 201 of the fluid cassette 102 will be referenced individually further below with respect to an operation of the fluid conditioning system 100. The high-capacity pumps 103 and the low-capacity pump 104 of the fluid conditioning system 100 are indicated respectively as P1, P2, P3, and P4 in the fluid circuit 350. The pumps include a cassette-in pump P1, a dialysate pump P2, a conductivity control pump P3, and an electrolyte/salt-dextrose pump P4. Table 2 lists approximate operational (e.g., fluid flow rate) ranges of the pumps P1-P4.

TABLE 2

Operational ranges of pumps of the fluid conditioning system 100.

| Pump | Operational Range (mL/min) |
|---|---|
| P1 | 20-600 |
| P2 | 20-600 |
| P3 | 0.5-90 |
| P4 | 0.5-90 |

The heater assembly 151 and the ammonia sensor 165 of the fluid conditioning system 100 are respectively indicated as a heat exchanger HX and an ammonia sensor NH in the fluid circuit 350. The conductivity sensors 203 of the fluid cassette 102 are indicated as a conductivity sensor CT1 associated with a fluid temperature upstream of the heat exchanger HX and a conductivity sensor CT2 associated with a fluid temperature downstream of the heat exchanger HX. In addition to having a capability to measure fluid conductivity, conductivity sensors CT1 and CT2 also have a capability to measure fluid temperature. Given that conductivity changes with temperature, the temperatures measured by the conductivity sensors CT1 and CT2 may, in some implementations, be used to correct conductivity values measured by the conductivity sensors CT1 and CT2 to provide temperature-compensated conductivity measurements. In some implementations, a fluid temperature measured by the conductivity sensor CT2 may also provide a safety check on a final temperature of dialysate that exits the fluid conditioning system 100 to flow into the dialysis system 303. The temperature sensors 120 of the fluid conditioning system 100 are indicated as a cassette-in temperature sensor T1 and a heat exchanger temperature sensor T2 in the fluid circuit 350. The pressure transducers 119 of the fluid conditioning system 100 are indicated as pressure transducers PT1, PT2, PT3, and PT4 in the fluid circuit 350.

The fluid conditioning system 100 can be operated in multiple stages to cooperate with the dialysis system 301 (e.g., with the dialyzer 337) for carrying out a fluid conditioning cycle in which a dialysis treatment is administered to a patient via the dialysis system 301. For example, the fluid conditioning cycle includes a priming stage, an infusion stage, and a treatment stage. The fluid conditioning cycle typically has a total duration of about 135 min to about 300 min.

Figure 20:
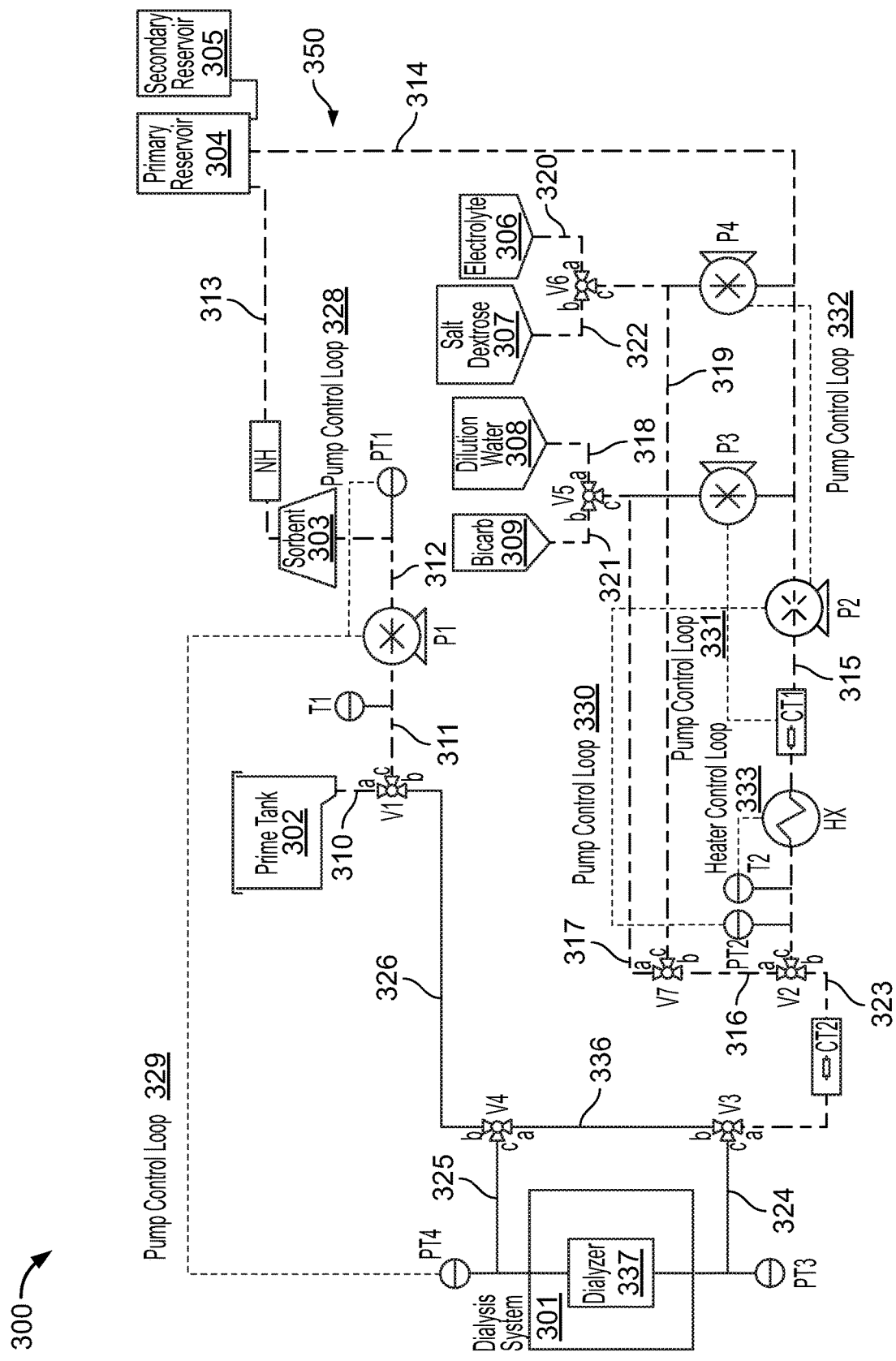
FIG. 20 illustrates a fluid flow path (indicated by highlighted fluid lines) of a priming stage of the fluid conditioning cycle carried out via the fluid circuit of FIG. 16.

FIG. 20 illustrates operation of the fluid conditioning system 100 during the priming stage, in which an initial volume of water is drawn into the fluid circuit 350 for subsequent creation of dialysate. At the beginning of the priming stage, the prime tank 302 is filled to about 7.6 L with water (e.g., tap water, bottled water, reverse osmosis water, distilled water, or drinking water) from a water source (e.g., a container 134 of water, shown in FIG. 19), pump P1 is turned on, and heat exchanger HX is turned on. The water is pumped by pump P1 from the prime tank 302 into a fluid line 310, through ports (a) and (c) of valve V1, into a fluid line 311, past temperature sensor T1, and into pump P1. At this stage of operation, pump P1 pumps water at a flow rate in a range of about 200 mL/min to about 600 mL/min, and heat exchanger HX is powered to maintain a fluid temperature at a set point in a range of about 15° C. to about 42° C.

If temperature sensor T1 detects a water temperature of greater than about 42° C., then a message is displayed on the display screen 148 to advise a user that the water temperature is too warm, valve V1 is closed, and pump P1 is turned off to prevent additional water from entering the fluid circuit 350. If temperature sensor T1 detects a water temperature of less than or equal to about 42° C., then ports (a) and (c) of valve V1 remain open, and pump P1 pumps the water through a fluid line 312 into the sorbent cartridge 303, into a fluid line 313, past ammonia sensor NH, and into the primary reservoir 304. At this stage of operation, the sorbent cartridge 303 purifies the water circulating in the fluid circuit 350, such that the water meets or exceeds water quality standards for drinking water as set by the Environmental Protection Agency (EPA) and water quality standards for hemodialysis water as set by the Association for the Advancement of Medical Instrumentation (AAMI) standard.

Once the primary reservoir 304 collects about 100 mL to about 500 mL of water, then pump P2 is turned on and pumps water into a fluid line 314, through pump P2, into a fluid line 315, past conductivity sensor CT1, and past the heat exchanger HX1, which heats the water in the fluid line 315 to the set point temperature. Pump P2 is controlled to pump water at a flow rate that is about equal to the flow rate at which water is pumped by pump P1. Water moves from the fluid line 315 through ports (c) and (a) of valve V2, into a fluid line 316, through ports (b) and (a) of valve V7, into a fluid line 317, through ports (c) and (a) of valve V5, into a fluid line 318, and further into the bag 308 until the bag 308 is filled to about 3.5 L to about 4.0 L with water (e.g., dilution water).

Next, ports (a) and (c) of valve V5 are closed, port (a) of valve V7 is closed, and port (c) of valve V7 is opened such that the pump P2 pumps water into a fluid line 319, through ports (c) and (a) of valve V6, into a fluid line 320, and further into the bag 306 until the bag 306 is filled to capacity with water to produce the electrolyte solution. Ports (a) and (c) of valve V6 are closed, port (c) of valve V7 is closed, port (a) of valve V7 is reopened, and ports (b) and (c) of valve V5 are opened. Pump P2 then pumps water into the fluid line 317, through ports (c) and (b) of valve V5, into a fluid line 321, and further into the bag 309 until the bag 309 is filled to capacity with water to produce the bicarbonate solution.

At this point in the priming stage, the set point temperature of the heat exchanger HX is increased to a range of about 31° C. to about 39° C. (e.g., where 39° C. is the maximum temperature achievable by heat exchanger HX), and the flow rate of pump P2 is reduced to a value within a range of about 100 mL/min to about 300 mL/min to increase an exposure time of the water within the heat exchanger HX for achieving the higher set point temperature. Ports (b) and (c) of valve V5 are closed, port (a) of valve V7 is closed, port (c) of valve V7 is opened, and ports (b) and (c) of valve V6 are opened. Accordingly, pump P2 pumps water into the fluid line 319, though ports (c) and (b) of valve V6, into a fluid line 322, and further into the bag 307 until the bag 307 is filled to capacity to produce the salt-dextrose solution. The higher set point temperature of heat exchanger HX facilitates dissolution of the salt-dextrose substance with the water flowing into the bag 309. At this point during the fluid conditioning cycle, the priming stage concludes, the prime tank 302 has substantially emptied, the pumps P1, P2 are turned off and the infusion stage can begin. The priming stage typically lasts a duration of about 10 min to about 30 min (e.g., about 20 min).

Figure 21:
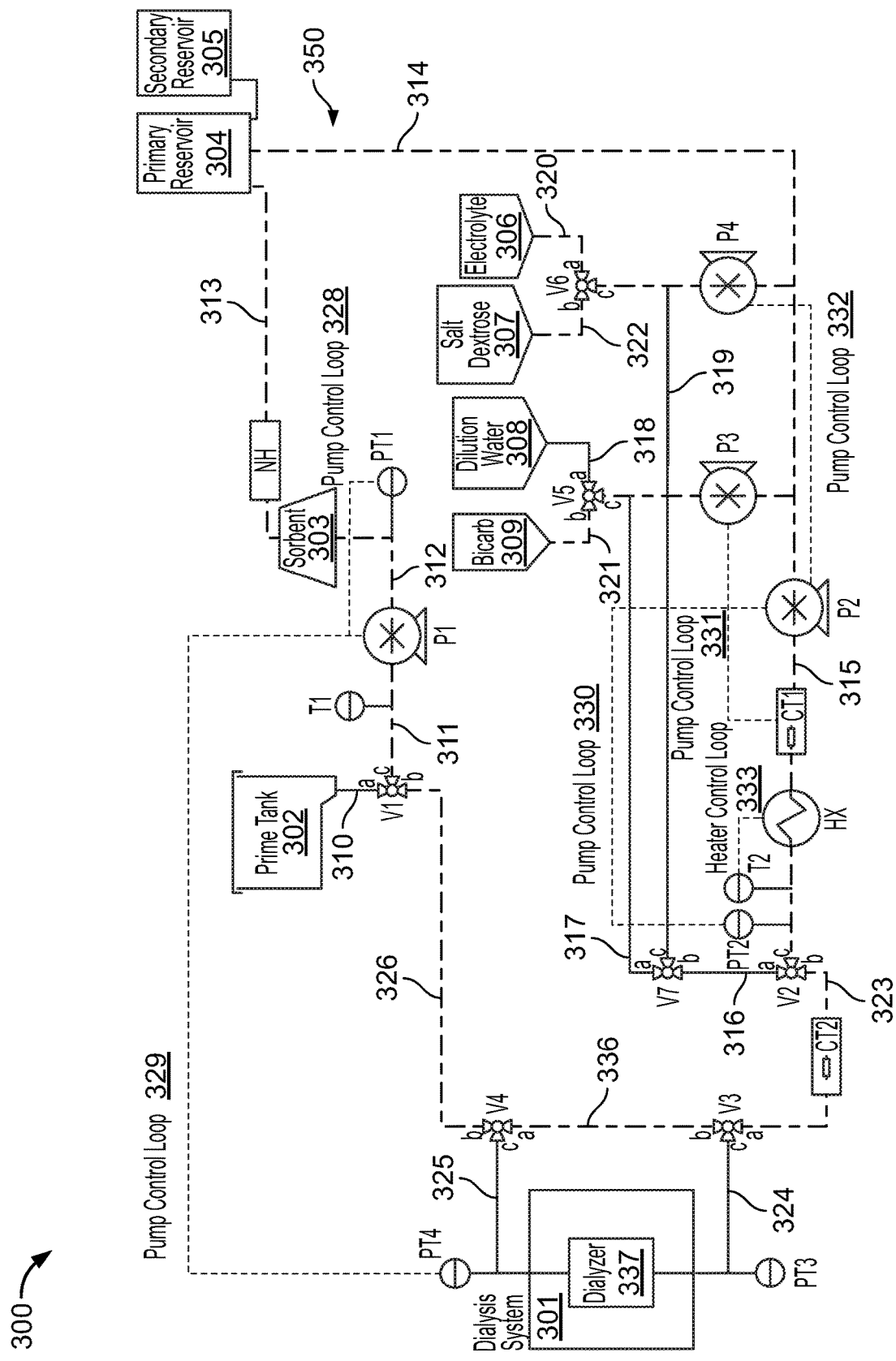
FIG. 21 illustrates a fluid flow path (indicated by highlighted fluid lines) of an infusion stage of the fluid conditioning cycle carried out via the fluid circuit of FIG. 16.

FIG. 21 illustrates operation of the fluid conditioning system 100 during the infusion stage, in which bicarbonate, salt, and dextrose are added to the water in the fluid circuit 350 to produce dialysate. In particular, bicarbonate, salt, and dextrose are added to the water in a controlled manner (e.g., under flow rate control) until the salt and dextrose reach physiologically acceptable concentrations and until the bicarbonate yields a physiologically acceptable fluid conductivity and fluid pH. During the infusion stage, heat exchanger HX is powered to maintain a fluid temperature at a set point in a range of about 35° C. to about 39° C.

At the beginning of the infusion stage, valve V7 is closed, port (a) of valve V2 closes, port (b) of valve V2 opens, ports (a) and (b) of both valves V3 and V4 open, port (b) of valve V1 opens, port (a) of valve V1 closes, ports (b) and (c) of valve V6 remain open, and ports (b) and (c) of valve V5 open. Pumps P1, P2 immediately turn on to pump water at a flow rate in a range of about 300 mL/min to about 600 mL/min within the fluid circuit 350. At the same time, pumps P3 and P4 are turned on. Pump P3 pumps bicarbonate solution out of the bag 309 at a flow rate of about 10 mL/min to about 100 mL/min, into the fluid line 317, through the pump P3, and into the fluid line 314. Pump P4 pumps salt-dextrose solution out of the bag 307 at a variable flow rate into the fluid line 319, through pump P4, and into the fluid line 314. The flow rate at which P4 initially pumps fluid is in a range of about 1 mL/min to about 100 mL/min. The flow rate is gradually stepped down by a factor of 2 at periodic time increments of about 1 min. The flow rates of pumps P3 and P4 are set to completely add the infusion volume respectively of the BC solution and the SD solution over a single revolution around the fluid circuit 350. Accordingly, the flow rates of pumps P3 and P4 depend on the flow rates of pumps P1 and P2 during the infusion stage. For example, if the flow rates of pumps P1 and P2 are set to 200 mL/min, then the flow rates of pumps P3 and P4 will be relatively slow. Conversely, if the flow rates of pumps P1 and P2 are set to 600 mL/min, then the flow rates of pumps P3 and P4 will be relatively fast.

Once the bag 307 empties of the salt-dextrose solution, port (b) of valve V6 closes, and port (a) of valve V6 opens to allow pump P4 to pump the electrolyte solution out of the bag 306 at a flow rate of about 0.5 mL/min to about 5 mL/min into the fluid line 314. Once the electrolyte solution reaches valve V3, the infusion stage concludes, and the treatment stage can begin. However, if the treatment stage does not begin immediately, the fluid conditioning system 100 can be operated to continue to circulate dialysate around the fluid circuit 350 through fluid lines 311, 312, 313, 314, 315, 323, 336, 326 or to allow the dialysate to remain static (e.g., without circulation) until the treatment stage begins. The infusing stage typically lasts a duration of about 5 min to about 6 min.

Figure 22:
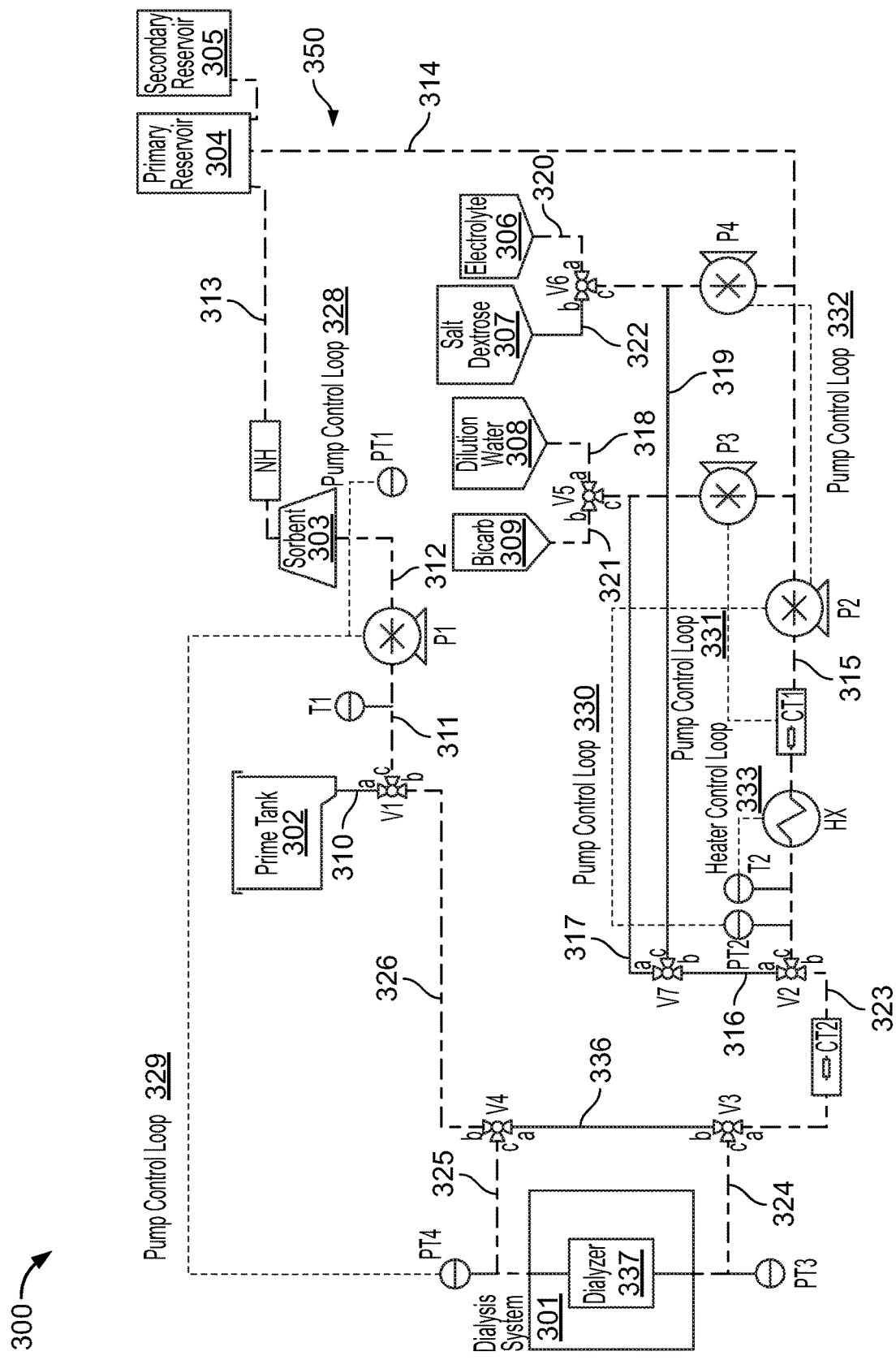
FIG. 22 illustrates a fluid flow path (indicated by highlighted fluid lines) of a treatment stage of the fluid conditioning cycle carried out via the fluid circuit of FIG. 16.

FIG. 22 illustrates operation of the fluid conditioning system 100 during the treatment stage, in which bicarbonate, salt, and dextrose are added to the water in the fluid circuit 350 to produce dialysate. The treatment stage includes a first phase in which bicarbonate solution is used to regulate a conductivity of the dialysate and a second phase in which dilution water is used to regulate a conductivity of the dialysate. Pumps P1 and P2 pump dialysate at a flow rate in a range of about 200 mL/min to about 600 mL/min. The set point temperature of heat exchanger HX is maintained at a physiologically acceptable temperature in an acceptable range of about 35° C. to about 39° C. (e.g., about 37° C.), as specifically selected by a user of the fluid conditioning system 100 to suit patient comfort. At any point during the treatment stage, if the dialysate fluid temperature measured at CT2 is outside of a range of about 35° C. to about 42° C., then the fluid conditioning system 100 will enter a bypass mode in which dialysate will flow through fluid line 336 to bypass flow through the dialysis system 301 via fluid lines 324, 325. While the fluid conditioning system 100 is operating in the bypass mode, a message will be displayed on the display screen 148 indicating that the fluid temperature is too low or too high. The fluid conditioning system 100 will remain in bypass mode until the fluid temperature stabilizes within the acceptable range.

During the first phase of the treatment stage, port (b) of valve V3 is closed, port (c) of valve V3 is opened to allow pump P2 to pump "fresh" dialysate (e.g., cleaned, conditioned dialysate) through a fluid line 324 and into the dialysis system 301, port (a) of valve V4 is closed, and port (c) of valve V4 is opened to allow pump P1 to pump "spent" dialysate (e.g., contaminated dialysate) through a fluid line 325 out of the dialysis system 301 and further into a fluid line 326. Accordingly, a bypass fluid line 336 that extends between valves V3 and V4 is closed. The spent dialysate has been infused with ultra-filtrate from the patient's blood within the dialysis system 301. The ultra-filtrate carries toxic substances, such as urea, all of the small water-soluble uremic toxins, and other toxic substances (e.g., guanidosuccinic acid, methylguanidine, 1-methyladenosine, 1-methylinosine, N2,N2-dimethylguanosine, pseudouridine, arab(in)itol, mannitol, α-N-acetylarginine, orotidine, oxalate, guanidine, erythritol, creatine, orotic acid, phenylacetylglutamine, creatinine, myoinositol, γ-guanidinobutyric acid, β-guanidinopropionic acid, (symmetric dimethyl-arginine) SDMA, asymmetric dimethyl-arginine (ADMA), sorbitol, uridine, and xanthosine).

From the fluid line 326, the spent dialysate is pumped through ports (b) and (c) of valve V1, the fluid line 311, pump P1, the fluid line 312, and into the sorbent cartridge 303. Within the sorbent cartridge 303, the toxic substances are removed from (e.g., filtered out of) the spent dialysate to produce "regenerated" dialysate (e.g., cleaned, unconditioned dialysate).

Figure 26:
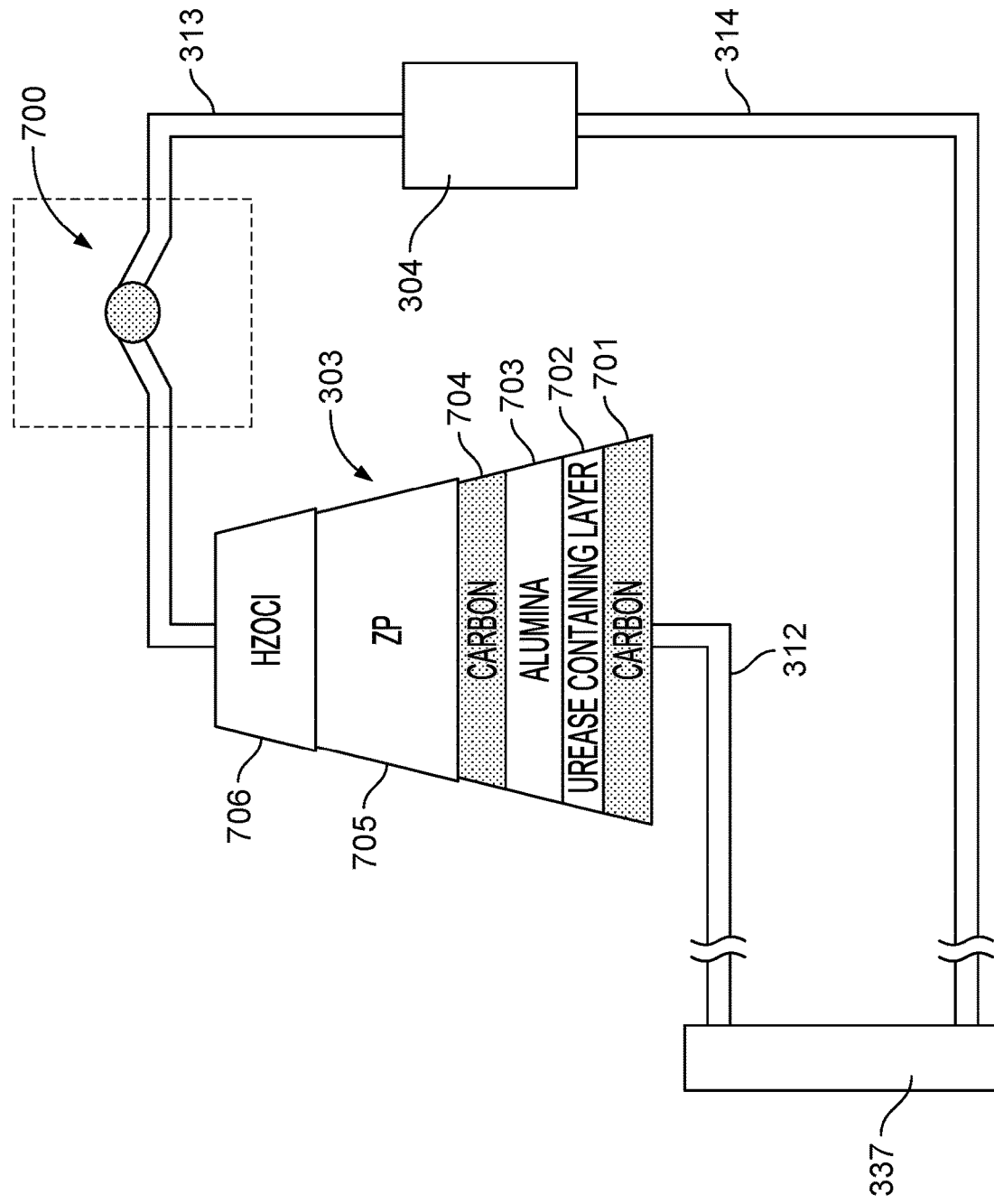
FIG. 26 shows a portion of the operational diagram of FIG. 18, including an ammonia detection system, a sorbent cartridge, and a primary reservoir of the fluid conditioning system of FIG. 1.

The sorbent cartridge 303 may include various layers that together regenerate the spent dialysate. The composition of an exemplary sorbent cartridge 303 is shown in FIG. 26. In one example, the sorbent cartridge 303 may include one or more of the following layers: a first carbon layer 701, a layer 702 containing material to convert urea to ammonia (e.g., a urease enzyme), a urease binding layer (e.g., an alumina layer) 703, a second (intermediate) carbon layer 704, a layer 705 containing an ion-exchange material (e.g., zirconium phosphate, ZP), and a phosphate adsorbent layer 706 (e.g., hydrous zirconium oxide with chloride counter ion, HZOCl). These layers are designed to remove contaminants and uremic solutes while at the same time maintaining an appropriate dialysate chemical composition. Spent dialysate flows through the cartridge from bottom to top (passing through layer 701 first).

The carbon layers 701 and 704 may adsorb heavy metals (e.g., lead, mercury, arsenic, cadmium, chromium and thallium), oxidants (e.g., chlorine and chloramine), other contaminants that may be present in tap water, and many organic and middle molecule uremic solutes found in spent dialysate, such as creatinine and uric acid. Suitable examples of the materials of each carbon layer include granular activated carbon and charcoal.

The material in layer 702 decomposes the urea in the dialysate into ammonium (e.g., positively charged ammonium ions, $NH_4^+$) and bicarbonate ($HCO_3^-$). Suitable examples of the urea-decomposing materials include urease, other immobilized enzyme, diatomaceous earth, and zirconium oxide. Suitable examples of urease enzyme include naturally occurring urease (e.g. urease from jack beans, other seeds or bacteria), urease produced by recombinant technology (e.g., in bacterial, fungal, insect, or mammalian cells that express and/or secrete urea-degrading enzymes), and urease produced synthetically (e.g., chemically synthesized). In some embodiments, the enzyme is urease.

The urease binding layer 703, when present, may include basic or neutral material. The materials of layer 703 immobilize the urease enzyme and other proteins leaching out of the urease layer 702. Suitable examples of urease binding materials include basic or neutral alumina ($Al_2O_3$). Other suitable examples of urease-binding materials include silica gel and diatomaceous earth. In some embodiments, the sorbent cartridge may omit the urease binding layer (e.g., an alumina layer), and/or the urease-containing layer may incorporate urease stabilized with and/or immobilized on a suitable material, such as, for example, silica gel or diatomaceous earth.

The ion-exchange material in the layer 705 adsorbs ammonium thereby removing ammonium from the circulating dialysate. In addition, the cation exchange material 705 adsorbs other positively charged species such as magnesium, calcium, and potassium, as well as heavy metal cations that may be found in tap water such as copper and iron. In exchange for the adsorbed cations, the ion-exchange material 705 releases hydrogen and sodium cations. Suitable examples of the ion-exchange materials 705 of the present disclosure include polymeric phosphate binders (e.g., polyamines), natural zeolites, and insoluble inorganic phosphates, or any combination thereof. Suitable examples of inorganic phosphates include Group IV metal phosphates, such as titanium phosphate, zirconium phosphate (ZP), and hafnium phosphate. In some embodiments, the ion-exchange material of the layer 705 is zirconium phosphate. In some embodiments, the zirconium phosphate is acid zirconium phosphate (AZP). In other embodiments, the zirconium phosphate is alkaline (AlkZP). In yet other embodiments, the zirconium phosphate is a combination of AZP and AlkZP (e.g., 10 wt. %, 30 wt. %, or 50 wt. % of AZP in the mixture of AZP and AlkZP).

The phosphate adsorbent layer 706 adsorbs all phosphates in the dialysate, including phosphates leached from ZP layer 705 and phosphates derived from the patient during the dialysis treatment. In addition to phosphates, the adsorbent layer 706 also adsorbs fluoride and other anions, such as oxoanions of heavy metals, and in exchange releases chloride ($Cl^-$) and hydroxyl ($OH^-$) anions. Suitable examples of the phosphate-adsorbing materials in the layer 706 include Group IV metal oxides, Group IV metal salts, and mixtures of Group IV metal oxides and salts. In one example, the phosphate-adsorbing material in the layer 706 is sodium zirconium carbonate, zirconium acetate, zirconium oxide (acid zirconium oxide or alkaline zirconium oxide), or hydrous zirconium oxide (e.g., hydrous zirconium oxide containing acetate or hydrous zirconium oxide with chloride counterion). In another example, zirconium oxide can be blended with the sodium zirconium carbonate when positioned in the layer 706 of the sorbent cartridge 303. In such a blend, exemplary concentrations of zirconium oxide include 10 wt. %, 50 wt. %, and 80 wt. %. The layer 706 must contain sufficient amount of hydrous zirconium oxide to adsorb all phosphates, including phosphates leached from ZP layer 705 and the phosphates derived from the patient during a dialysis treatment, in order to avoid an undesirable level of phosphates in the regenerated ("clean") dialysate. In one example, the ion-exchange layer 705 is zirconium phosphate (ZP), and the hydrous zirconium oxide (HZO) in the layer 706 adsorbs all phosphates leaching out of the ZP layer 705.

In some embodiments, the layer 705, or the layer 706, or both layers 705, 706 may contain a mixture of zirconium phosphate (e.g., acid zirconium phosphate) with hydrous zirconium oxide (e.g., alkaline hydrous zirconium oxide). Suitable amounts of ZP in such a mixture include about 10 wt. %, about 30 wt. %, and about 70 wt. %.

In some embodiments, the sorbent cartridge 303 includes an additional layer on top of the adsorbent layer 706 containing sodium bicarbonate. It does not bind anything but releases $Na^+$ and $HCO_3^-$ into the regenerated dialysate. Table 3 shows a typical composition of a sorbent cartridge.

TABLE 3

Composition of a typical sorbent cartridge 303.

| component | amount (g) |
| --- | --- |
| NaHCO$_3$ | 35 |
| HZOCl | 200 |
| ZP | 1600 |
| activated carbon | 325 |
| alumina | 20 |
| urease | 110 |
| activated carbon | 100 |

Methods are described herein for making ZP containing substantially no leachable phosphates (e.g., no more than 0.02 mg/g leachable phosphates). It is understood that the amount of "leachable phosphate(s)" (e.g., 0.02 mg) refers to the amount of phosphorous (P) in the phosphate ions that leach or are otherwise released from the sorbent cartridge (sometimes denoted as $PO_4$—P or phosphate-phosphorous).

The ZP prepared by the methods of the present disclosure can be used, for example, in the ZP layer 705 of the sorbent cartridge 303. Using ZP containing substantially no leachable phosphates advantageously allows preparation of a sorbent cartridge 303 with substantially less hydrous zirconium oxide (HZO) in the layer 706 as compared to the cartridge with conventional ZP in the layer 705 containing about 2.5 mg of leachable phosphates per one gram of the material. For example, using the ZP of the present disclosure can result in sorbent cartridges containing 3 times, 40 times, or 80 times less HZO as compared to cartridges prepared with conventional ZP containing about 2.4 mg/g or more of the leachable phosphates (e.g., 2.5 mg/g of leachable phosphates). Because the amount of zirconium material required in the cartridge is greatly reduced, the cost of the sorbent cartridge is also reduced, leading to the overall reduction in costs of the dialysis treatment. In addition, elevated serum phosphate in patients may lead to dangerous conditions, such as various bone pathologies, hypocalcemia, or hyperphosphatemia. Using ZP with substantially no leachable phosphates in the sorbent cartridge of the present dialysis system advantageously avoids and prevents these dangerous conditions.

Zirconium phosphate is an acidic inorganic compound having a layered structure with a general formula $Zr(OPO_3H)_2$. In its hydrous form, zirconium phosphate has formula $Zr(OPO_3H)_2 \cdot nH_2O$, where variable n is from 1 to 4. Zirconium phosphates have high thermal and chemical stability, solid-state ion conductivity, resistance to ionizing radiation, and the capacity to incorporate different types of ions and molecules with different sizes between their layers (e.g., free phosphates). When reacted with alkali hydroxide (e.g. sodium hydroxide), the acid zirconium phosphate exchanges some of the $H^+$ cations within its structure for the alkali metal cations (e.g., sodium cations, $Na^+$), to become an alkaline zirconium phosphate (AlkZP). In one example, the alkaline zirconium phosphate has formula $Zr(OPO_3H)_2$. In another example, the alkaline zirconium phosphate has formula $Zr(OPO_3(H)_x(Na)_y)_2$, where the sum of x and y is 1. In some implementations, x is 0.3 and y is 0.7, x is 0.1 and y is 0.9, or x is 0.5 and y is 0.5.

Figure 27:
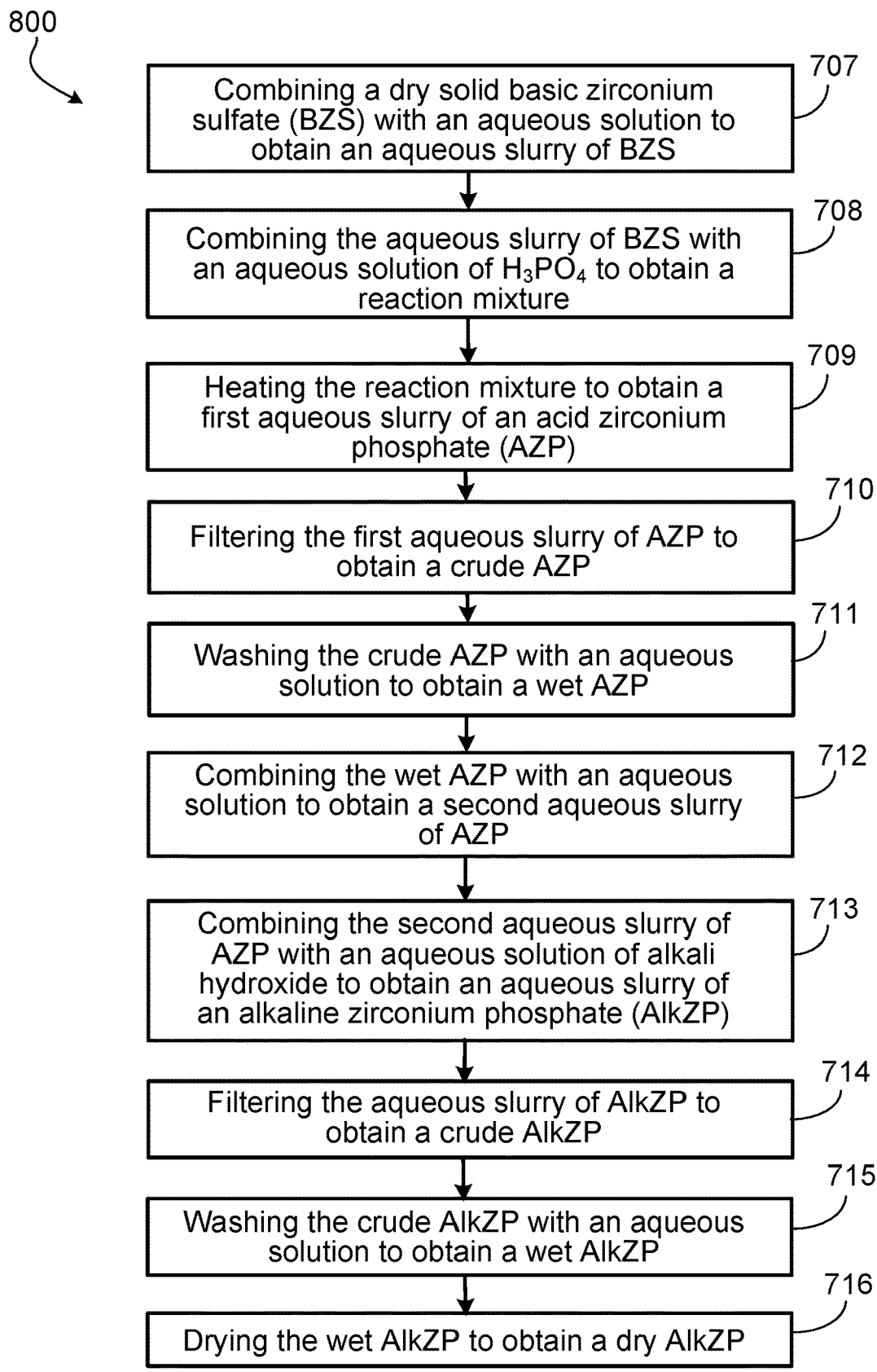
FIG. 27 contains a flow-chart for an exemplary method of making an alkaline zirconium phosphate which does not include a step of drying an acid zirconium phosphate prior to reacting the acid zirconium phosphate with an alkali hydroxide.

Traditionally, alkaline zirconium phosphate is prepared by treating acid zirconium phosphate with alkali hydroxide. FIG. 27 contains a flow chart showing operations in an exemplary process 800 for making alkaline zirconium phosphate from the basic zirconium sulfate starting material. In 707, the source material basic zirconium sulfate is combined with an aqueous solution to yield an aqueous slurry. Generally, zirconium sulfate is an inorganic compound of formula $Zr(SO_4)_2 \cdot nH_2O$, where n is 0, 2, 4, or 6, which is readily available from numerous commercial sources. The aqueous solution contains primarily water as an aqueous solvent, and may optionally contain various solutes that control viscosity of the fluid and facilitate the slurry formation. The aqueous solution may also contain an acid or a base to control pH, stability, and chemical composition of the slurry. For example, the aqueous solution in 707 may contain sulfuric acid ($H_2SO_4$). In 708, the aqueous slurry of basic zirconium sulfate is combined with an aqueous solution of phosphoric acid ($H_3PO_4$) to obtain a reaction mixture. An ambient temperature is typically insufficient to drive the reaction between the phosphoric acid and the zirconium sulfate to completion. Hence, in 709, the reaction mixture is heated to a temperature sufficiently high to facilitate the reaction, such as a temperature in a range of about 70° C. to about 90° C. When sufficiently heated, zirconium sulfate reacts with the phosphoric acid to form acid zirconium phosphate, for example, as shown below:

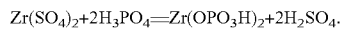

The reaction time in 709 varies and is typically sufficient to achieve complete conversion of zirconium sulfate to zirconium phosphate. In one example, the reaction mixture in 709 may be heated from about 15 min to about 1 hour. In some implementations, the reaction time is about 30 min. Once the reaction is complete, the reaction mixture is filtered in 710 to separate the crude solid AZP and the filtrate containing excess of phosphoric acid. The crude AZP is then washed with an aqueous solution in 711 to yield wet AZP. The washing may be carried out by adding an aqueous solution (e.g., pure water such as tap water) to the crude solid AZP to yield an aqueous slurry, and then filtering the slurry to separate the aqueous filtrate from the washed wet AZP. During the washing process, excess phosphoric acid and other impurities are carried away in the filtrate leaving pure wet AZP as a filter cake. In the next step of the AlkZP preparation, wet AZP is combined with an aqueous solution to obtain an AZP slurry in 712, and then the AZP slurry is treated with a sufficient amount of an aqueous solution of an alkali hydroxide (e.g., NaOH) in 713 to obtain a slurry of AlkZP. Typically, alkali hydroxide is added to the AZP slurry to a pH from about 8 to about 9. Using NaOH as an example, the following reaction may occur between AZP and alkali hydroxide during the addition (titration):

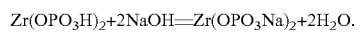

Once the reaction has reached equilibrium (stable pH), the AlkZP slurry is filtered in 714 to obtain a crude wet AlkZP, which is then washed with water in 715 to yield a wet AlkZP. In some implementations, the AlkZP may be washed with water as described for 711. During the washing process, excess alkali hydroxide and other impurities are carried away in the filtrate leaving pure wet AlkZP as a filter cake. Finally, the wet AlkZP can be dried, e.g., in an oven, to a moisture level of about 14 wt. % to about 18 wt. % loss on drying (LOD).

The process of preparation of AlkZP can be carried out using conventional equipment generally used in the chemical industry. Suitable examples of the conventional equipment include vessels, apparatuses, and machinery that are generally used in preparation of inorganic adsorbent materials, such as reactors, agitators, mixers, pumps, funnels, centrifuges, filters, and ovens. The equipment can be made from stainless steel, glass (including borosilicate glass), aluminum, or plastic, or any combination thereof (e.g., glass-lined steel). Such equipment is schematically shown in FIG. 28.

Figure 28:
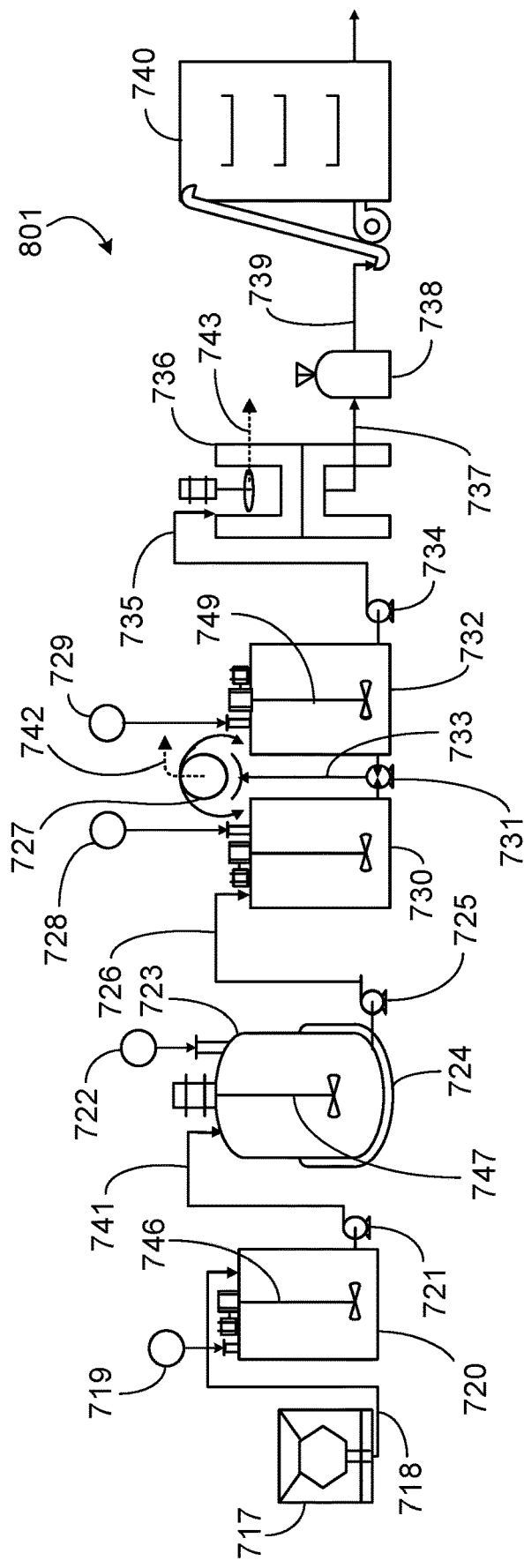
FIG. 28 contains a schematic representation of a process of making zirconium phosphate from zirconium sulfate.

Referring to FIG. 28, basic zirconium sulfate is supplied from the storage unit 717 through the line 718 to a reaction vessel 720. Aqueous solution (e.g., tap water or distilled water) is then added to the reactor 720 from the fluid tank 719 to create an aqueous slurry of BZS in the reactor 720. In some implementations, density of the slurry is about 4 mL of the aqueous solution per about 1 g of the dry material (BZS). The reactor is equipped with a mechanical agitator 746 (e.g., anchor-, propeller-, or paddle-type agitator) to mix the BZS and water to create a homogenous slurry. In some implementations, the BZS slurry in reactor 720 can be stirred from about 50 revolutions per minute (RPM) to about 100 RPM, for a time period from about 2 hours to about 3 hours. Pump 721 then pumps the homogenous BZS slurry from reaction vessel 720, through the pipe 741, to the reactor 723. An aqueous solution of phosphoric acid is then added to the reactor 723 from fluid tank 722 at a rate from about 5 gal/min to about 15 gal/min. In some implementations, the concentration of phosphoric acid in the aqueous solution 722 is about 37 wt. % (e.g., 37.7 wt. %). In one example, an amount of phosphoric acid added to the reactor 723 is in about 60 vol. % excess of the amount of the BZS in the reactor. Reactor 723 is equipped with a mechanical agitator 747 (e.g., anchor-, propeller-, or paddle-type agitator) to ensure homogeneity of the reaction mixture. In some implementations, the reaction mixture is stirred at about 85 RPM (the speed of the agitator is generally dependent on the size of the agitator, the size of the reactor, the volume of the slurry, and the density of the slurry). The parameters in this example apply to full scale plant conditions (as opposed to laboratory conditions). Laboratory conditions may include stirring a slurry at 100-500 RPM, stirring a reaction mixture at 85 RPM, and adding $H_3PO_4$ at 5-15 mL/min. In one example, steam or hot water may be supplied to the reactor through jacket 724 to heat the reactor mixture to the reaction temperature of about 70° C. to about 90° C., or about 75° C. to about 85° C. In some embodiments, the reactor is heated to the reaction temperature of about 85° C. Once temperature has been reached, the reaction between zirconium sulfate and phosphoric acid may occur for a time period from about 30 min to about 90 min (e.g., 30 min or 60 min). If reactor heating time in included in the reaction time, the exposure of BZS to phosphoric acid is no more than about 2-4 hours. In some implementations, the reaction time is from about 15 min to about 45 min. Once the reaction is complete (e.g., all or substantially all of the zirconium sulfate is converted to zirconium phosphate), the reaction mixture in reactor 723 is allowed to cool to a temperature below about 50° C. to 65° C. and pumped, by pump 725, through the fluid line 726, to the vessel 730, and then, by the pump 731, to the vacuum drum filter 727. The drum filter 727 separates filtrate (effluent) from the crude reaction product (crude wet acid zirconium phosphate). In some implementations, filtrate contains, in addition to water, the excess amount of phosphoric acid, trace amounts of sulfuric acid, and various other water-soluble impurities. At the same time, the crude wet (damp) zirconium phosphate product after filtration on filter 727 contains, in addition to the solid AZP, some amount of phosphoric acid and the phosphate ions intercalated between the layers of the zirconium phosphate crystal structure. After separation, AZP remains at the top of the drum filter as a filter cake, while filtrate is removed to the waste neutralization system through the fluid line 742.

In order to wash the crude AZP from the remainder of the phosphoric acid and other impurities, the solid filter cake from vacuum drum filter 727 is returned to the vessel 730. At the same time, an aqueous solution (e.g., water) is added to the vessel 730 from the fluid tank 728 to create a slurry. In some implementations, the density of this slurry is from about 2 mL to about 6 mL of the aqueous solution per about 1 g of the crude AZP material. The slurry is stirred in the vessel 730 at about 70 RPM to about 85 RPM using mechanical agitator 748. During the stirring, free phosphoric acid, free phosphate ions, and other water-soluble impurities dissipate from the crude AZP into the aqueous phase of the slurry. In one example, the stirring in vessel 730 is carried out for about 40 min or about 2 hours. In some implementations, the slurry is stirred (and the crude AZP is washed) for about 6 hours (or about 12-15 hours if the slurry is left in the tank overnight). After completion (e.g., when the concentration of free phosphoric acid in the aqueous phase of the slurry remains constant), the slurry is pumped by pump 731 to the drum filter 727 to obtain washed wet AZP as a filter cake and an effluent containing the remainder of the excess phosphoric acid. The effluent is dumped from the filter 727 to a waste neutralization system through the fluid line 742. Referring to FIG. 28, if the drum filter rotates counterclockwise, the AZP filter cake is transferred back to the vessel 730 and the washing cycle is repeated. The washing cycle can be repeated until free phosphoric acid is detected in the filtrate in the fluid line 742 below a predetermined concentration limit (e.g., about 600 ppm to about 2000 ppm). In some implementations, about 18 to 24 washing cycles are carried out to obtain a wet AZP as a filter cake that is substantially free from phosphoric acid. With all the washing cycles, the entire washing phase of the process takes from about 24 to about 26 hours. At the completion of the washing phase, the drum filter 727 rotates clockwise to transfer wet AZP to the vessel 732. At the same time, an aqueous solution is added to the vessel 732 from the fluid tank 729 to obtain a slurry having a density of about 2 mL to about 6 mL of the aqueous solution per about 1 g of the wet AZP material. Then, an aqueous solution of an alkali hydroxide (e.g., sodium hydroxide) is added to the slurry from the fluid tank 729 to obtain a pH of about 8 to about 9. In one example, the rate of addition of alkali hydroxide solution to the slurry is from about 1 gal/min to about 11 gal/min. Concentration of alkali hydroxide in the aqueous solution is typically from about 25 wt. % to about 50 wt. %. The resultant reaction mixture is stirred in the vessel 732 using a mechanical agitator 749 for about 1 hour or about 2 hours at about room temperature, until the AZP and converted AlkZP in the slurry reach equilibrium and the pH has stabilized. Pump 731 then pumps the slurry containing AlkZP from vessel 732 to vacuum drum filter 727. The drum filter separates crude solid AlkZP from liquid filtrate containing excess alkali hydroxide and other impurities. The drum filter rotates counterclockwise to transfer crude AlkZP to the vessel 732, and an aqueous solution (e.g., water) in an amount of about 2 mL to about 6 mL per 1 g of crude AlkZP is added to the vessel to create a washing slurry. The washing cycle may be repeated as necessary as described above for AZP until no more alkali hydroxide is detected in the waste line 742. At the completion of the washing phase, wet AlkZP (e.g., a sludge) is transferred by pump 734 through the pipe 735 to the centrifuge 736. A variety of centrifuges may be employed at this stage to dewater wet AlkZP. Suitable examples of the centrifuges include a solid bowl basket, a tubular bowl centrifuge, screen scroll centrifuge, vibrating screen centrifuge, pusher centrifuge, cascade sliding centrifuge, filter press, and a decanter. The dewatering is typically carried out in the centrifuge 736 for about 5 hours (depending on the batch size.), and the filtrate (effluent) is removed from the centrifuge 736 to the waste management system through the fluid line 743. Dewatered (substantially dewatered, slightly damp to touch) powder of AlkZP is transferred to the storage unit 738 through a pipe 737, and then from the storage unit 738 to the drying unit 740 through a pipe 739. Any dryer that is capable to reduce moisture level in a solid inorganic material can be used in the process. Suitable examples of a dryer 740 include a fluidized bed drier, a rotary drier, a rolling bed drier, a conduction dryer, a tray drier, a rotary drier, an oven, a microwave drier, and a convection dryer. In some implementations, hot gas, such as air or nitrogen, may be used to dry AlkZP. A typical drying process takes from about 18 hours to about 22 hours (depending on the type of dryer used and batch size). Typically, AlkZP is dried in 740 until the measured loss on drying (LOD) is from about 12 wt. % to about 38 wt. %. In some implementations, the LOD is from about 14 wt. % to about 18 wt. % (e.g., about 14 wt. %, about 16 wt. %, about 17 wt. %, or about 18 wt. %). In some implementations, using a highly efficient drier 740, such as a rotary drier, eliminates the need to use a centrifuge 736 to prepare wet AlkZP for drying. That is, wet AlkZP may be transferred directly from the vessel 732 to the dryer 740, which is a rotary drier or another drier of similar efficiency. A whole step elimination yields a rate of production of AlkZP of about 66 kg/hr. In some implementations the centrifuge step may be avoided by either (1) collecting the material directly off of the drum filter 727; or (2) pump the slurry from a reaction tank (724 or 730, 732) directly to a filter press instead of the drum filter. The filter press would act as the filter, wash station, and de-watering station all in one. The material collected directly from the drum filter or filter press could then be used in the dryer 740.

For a conventional process using 60 vol. % excess of $H_3PO_4$ relative to BZS, the total time of making one batch of AlkZP is from about 60 hours to about 62 hours (including about 2 hours for making slurry of BZS, about 9 hours for reacting BZS with phosphoric acid, about 26 hours for washing crude AZP, reacting AZP with NaOH, and washing the resultant crude AlkZP, about 5 hours for dewatering, and about 20 hours for drying AlkZP to desired LOD). This conventional process achieves final production rate of dry AlkZP from about 24 kg/hr to about 28 kg/hr. Table 4 summarizes performance characteristics of the sorbent cartridge 303 prepared with AlkZP in layer 705:

TABLE 4

Operational ranges of AlkZP in layer 705 prepared by a conventional method.

| Cartridge characteristic | Operational range |
| --- | --- |
| leachable phosphate | 2.4–2.5 mg/g |
| sodium content | 80-94 mg/g |
| ammonium adsorption | ~17-19 mg/g |
| P:Zr ratio | ~1.7-1.8 |

Referring to process 800 (FIG. 27), it was unexpectedly found that using only about 10 vol. % excess of $H_3PO_4$ relative to BZS in 708, 709 allows to achieve the desired cartridge performance characteristics for the AlkZP layer while simultaneously reducing the leachable phosphates to about 0.8 mg/g, and further allows to significantly improve the AlkZP manufacturing process parameters. Referring to FIG. 28, in the improved process, only about 10 vol. % excess of $H_3PO_4$ is added to the reactor 723. As a result, the reaction time in reactor 723 can be reduced to less than about 4 hours. This significantly reduces the amount of excess phosphoric acid in the reaction slurry that needs to be washed off in the subsequent washing phase using the vessels 730, 732, pumps 727, 731, and fluid tanks 728, 729. Instead of 18-24 washes, the excess phosphoric acid can be eliminated in only 4 one-hour washes, so that the overall washing phase of the manufacturing process takes only about 4 hours. This results in $H_3PO_4$ savings of about 40% (e.g., 37%)) and water savings of about 80% when compared to the conventional process using 60 wt. % $H_3PO_4$ excess. The timing of the washing phase of the process is reduced by about 18-20 hours, the drying time is reduced by about 5-10 hours, and the overall time of the batch preparation is reduced to about 20-22 hours. In sum, a reduction of $H_3PO_4$ used to prepare AZP from BZS leads to about 47% increase in production rate of dry AlkZP while maintaining the advantageous material properties. Using the improved process, production rate of dry AlkZP is from about 36 kg/hr to about 40 kg/hr.

It was also unexpectedly found that (i) using only about 10 vol. % excess of $H_3PO_4$ relative to BZS and (ii) drying wet AZP prior to combining AZP with alkali hydroxide allows not only to achieve the desired cartridge performance characteristics for the AlkZP layer 705, but also to reduce the leachable phosphates to about 0.02-0.03 mg/g. That is, the intermediate step of drying AZP prior to reaction with alkali hydroxide allows a 40-fold reduction in the levels of leachable phosphate in the ZP cartridge material as compared to the process that does not include the AZP drying step (a reduction from 0.8 mg/g leachable phosphate to 0.02 mg/g amounts to 40-fold reduction).

Figure 29:
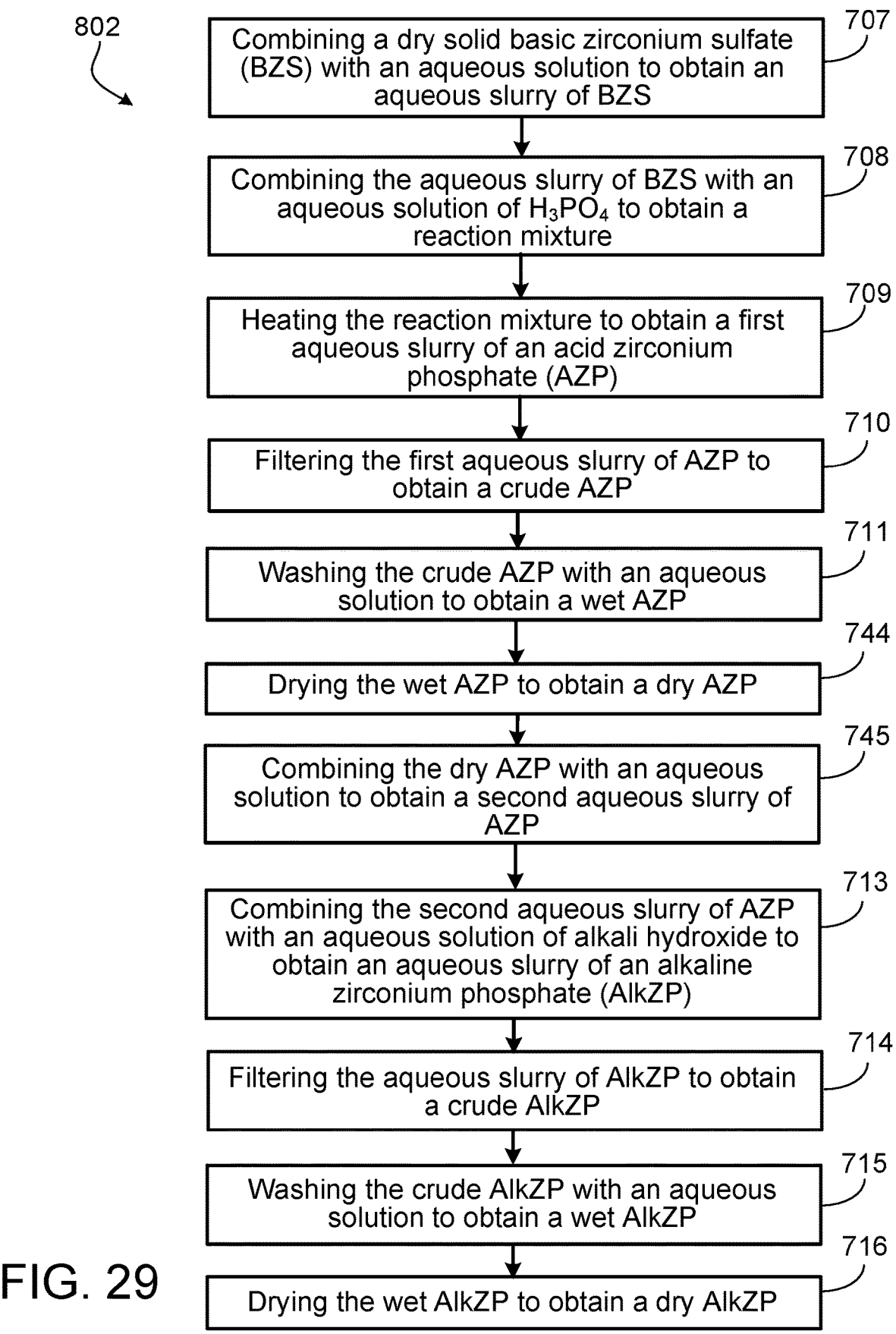
FIG. 29 contains a flow-chart for an exemplary method of making an alkaline zirconium phosphate which does include a step of drying an acid zirconium phosphate prior to reacting the acid zirconium phosphate with an alkali hydroxide.

FIG. 29 contains a flow chart showing operations in an exemplary process 802 for making AlkZP from BZS starting material using dry AZP as an intermediate. Steps 707, 708, 709, 710, 711 can be carried out as described previously for conventional process of FIG. 27, including using only 10 vol. % excess of $H_3PO_4$ relative to BZS in steps 708, 709. The conventional process used 60% excess $H_3PO_4$ volume above what was calculated to be the stoichiometrically required volume. The improved process described here uses 10% excess volume above that required volume. The wet AZP that was obtained in step 711 can be dried in 744 (e.g., in an oven) to a moisture level of about 14 wt. % to about 18 wt. % loss on drying (LOD) to yield a dry AZP. The dry AZP can be re-slurried in 745 to obtain an aqueous slurry of AZP, which can be used for further titration with alkali hydroxide in 713 to obtain an aqueous slurry of the desired AlkZP product. Steps 713, 714, 715, 716 can be carried out as described previously for the conventional process depicted in FIG. 27. The drying of wet AZP occurs as follows. Referring to FIG. 28, wet AZP in vessel 732, instead of being reacted with alkali hydroxide, is transferred by pump 734 through pipe 735 directly to the centrifuge 736. After dewatering in the centrifuge, AZP is dried in the drying unit 740 to a moisture level of about 14% to about 18% LOD. Dry AZP is a commercial product. Using the procedures described for steps 707-711 and 744, a batch of dry AZP product may be prepared in about 20-22 hours with an overall production rate of about 40 kg/hr. Because only 10 vol. % excess of $H_3PO_4$ was used in 708, only four 40 minute to one-hour washes are needed to rid AZP of the excess phosphoric acid (i.e., the wash phase of the process takes about 4 hours), and the dry time is only about 6 hours. The leachable phosphate level in wet AZP (e.g., AZP prepared in step 711) is about 1.2 mg/g to about 1.4 mg/g. The leachable phosphate level in dry AZP (e.g., AZP prepared in step 744) is about 0.08 mg/g to about 0.1 mg/g. This material can be used in cartridge layer 705, alone or in combination, for example, with zirconium oxide or with AlkZP. In order to prepare AlkZP, dry AZP is placed in vessel 732. Aqueous solution (e.g., tap water) is added to vessel 732 at the same time from fluid source 729 to make a slurry having a density of about 1 mL to about 3 mL of the aqueous solution per about 1 g of the dry AZP material. The slurry is stirred using mechanical agitator 749, e.g., until the concentration of phosphoric acid and free phosphates in the aqueous phase of the slurry remains constant. In one example, the slurry is stirred for about 15 min to about 1 hour. After this time, an aqueous solution of alkali hydroxide is added to reactor 732 from fluid source 729 until pH of the aqueous phase of the slurry reaches about 8 to about 9. Exemplary rate of addition of alkali hydroxide solution to the slurry is from about 1 gal/min to about 11 gal/min, and exemplary concentration of alkali hydroxide in the aqueous solution is from about 25 wt. % to about 50 wt. %. Once the reaction is complete, the slurry of AlkZP product in the vessel 732 is handled as described previously for the conventional process using centrifuge 736 and drier 740 to the LOD level of about 14% to about 18%. Unexpectedly, the levels of leachable phosphates in the dry AlkZP product obtained from drier 740 is from about 0.01 mg/g to about 0.03 mg/g.

Without being bound by a theory, it is believed that wet AZP obtained after washing (e.g., wet AZP obtained in step 711) contains two types of phosphate ions: (i) the phosphate ions that are a part of the ZP structure and that are strongly bound to zirconium atom through ionic bonds; and (ii) free phosphates that are weakly bound to the molecules of water through, e.g., electrostatic interactions and Van der Vaal's forces. The water molecules, in turn, are bound to zirconium atom through weak coordinate bonds. It is believed that only the phosphates that are weakly bound to the molecules of water in the wet AZP become leachable phosphates when the resultant AlkZP is used in layer 705 of the sorbent cartridge 303. It is further believed that when wet AZP is used to prepare AlkZP (e.g., in 712), the phosphate ions that are loosely bound to water remain within the ZP material throughout the process. That is, during the step of drying of AlkZP (e.g., 716), water evaporates out of the material, but the leachable phosphates remain entrapped within the compound structure, and leach out of the material during the dialysis when dialysate fluid flows through the layer 705. It is believed that upon addition of NaOH to AZP that contains leachable phosphates, the leachable phosphates in the resultant AlkZP may be "salting out" into the material matrix (e.g., in the form of $Na_3(PO_4)$), or undergoing some other reaction that retards volatilization of $PO_4^-$ as the material is dried. In contrast, when dry AZP is used to prepare AlkZP, it is believed that when the water is evaporated off during the AZP drying step, the weakly bound phosphates are also volatilized with the evaporated water and are thus removed from the AZP material during the drying process. Thus, when dry AZP is re-slurried for the preparation of AlkZP in 745, there are no more weakly bound, leachable phosphates left in the material. When AlkZP is washed after reaction of AZP with alkali hydroxide and subsequently dried (e.g., in 715, 716), no more leachable phosphates remain entrapped within the material (e.g., there no more phosphate material to "salt out" in the form of $Na_3PO_4$). The differences between amounts of leachable phosphates and subsequent amounts of zirconium oxide material that are necessary in the cartridge to adsorb these leachable phosphates are shown in Tables 5 and 6. Table 5 summarizes cartridge contents when conventional AlkZP is used in layer 705, while Table 6 summarizes cartridge contents when low-leachable phosphate AlkZP of the present disclosure is used in layer 705.

TABLE 5

Operational ranges of AlkZP in layer 705 prepared by a conventional method.

| Cartridge component | amount |
|---|---|
| ZP65 | 1600 g |
| AZP leachable phosphates | 0.2 mg/g |
| AlkZP leachable phosphates | 2.5 mg/g |
| Total patient phosphates | 1.6 g |
| Total ZP phosphates | 2.9 g |
| HZO-Cl required | 137 g |

TABLE 6

Operational ranges of AlkZP in layer 705 prepared by an improved method.

| Cartridge component | amount |
|---|---|
| ZP65 | 1600 g |
| AZP leachable phosphates | 0.2 mg/g |
| AlkZP leachable phosphates | 0.03 mg/g |
| Total patient phosphates | 1.6 g |
| Total ZP phosphates | 0.1 g |
| HZO-Cl required | 52 g |

As can be seen in Tables 5 and 6, using the AlkZP of the present disclosure reduces the amount of HZO (material of layer 706) in the cartridge by about 60%. That is, when AlkZP containing low leachable phosphates is used in the cartridge in place of the conventional AlkZP material, the amount of phosphate adsorbing material in layer 706 of the cartridge can advantageously be reduced by more than half. This material reduction significantly reduces the cost of the cartridge and subsequently the cost of the dialysis treatment.

Figure 30:
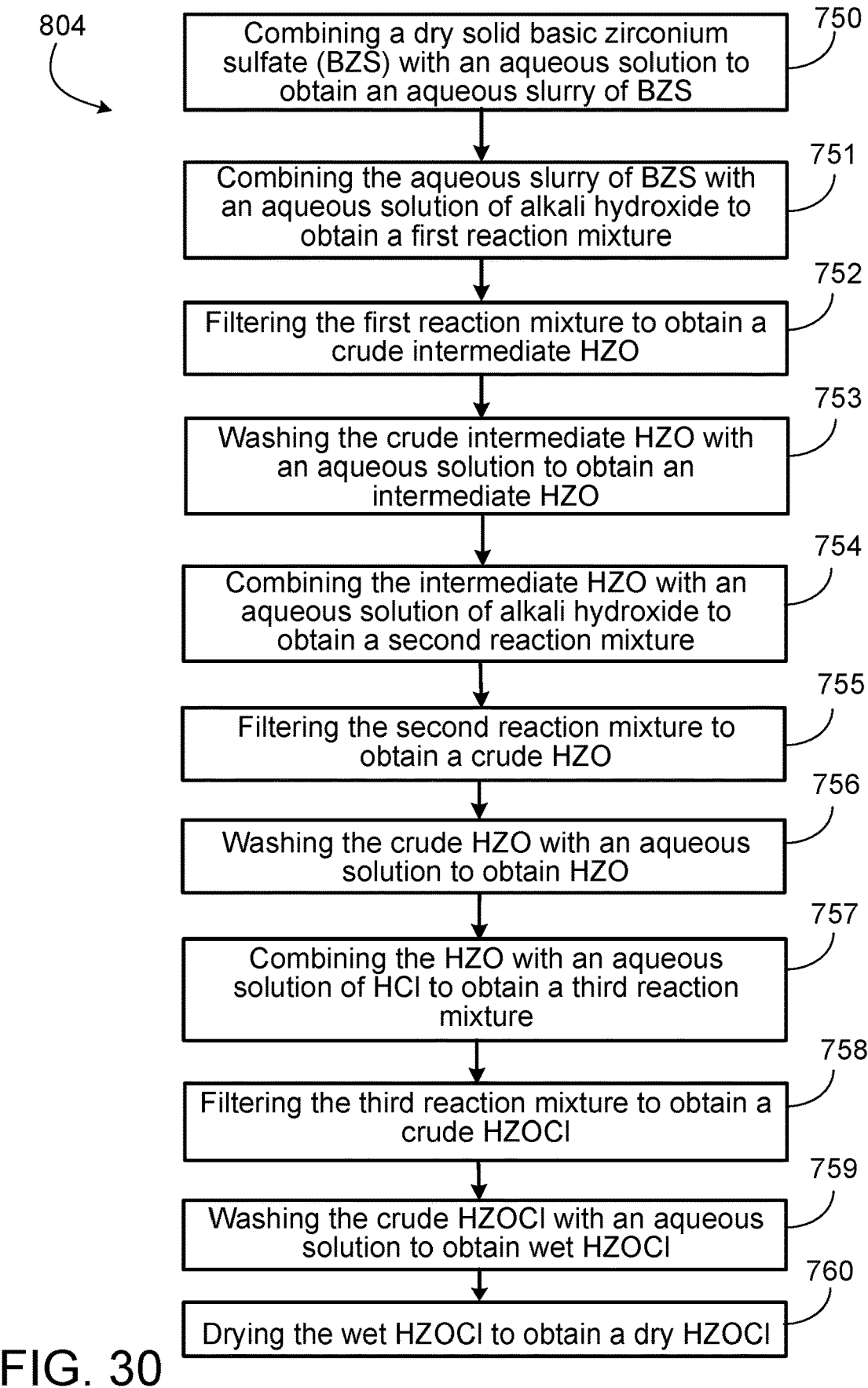
FIG. 30 contains a flow-chart for an exemplary method of making hydrous zirconium oxide with chloride counterion, which includes two steps of treating zirconium sulfate with an alkali hydroxide.

Traditionally, hydrous zirconium oxide with chloride counter ion (HZOCl) is prepared by treating basic zirconium sulfate with an alkali hydroxide to obtain HZO and then treating HZO with hydrochloric acid to obtain HZOCl. FIG. 30 contains a flow chart showing operations in a conventional process 804 for preparing HZOCl. Referring to FIG. 30, in 750, the source material basic zirconium sulfate is combined with an aqueous solution to yield an aqueous slurry, having a density of, for example, 4 mL of water per 1 g of solid BZS. In 751, the aqueous slurry of BZS is combined with an aqueous solution of an alkali hydroxide (e.g., NaOH) to obtain a reaction mixture. Exemplary concentration of alkali hydroxide in the solution may be from about 5 wt. % to about 50 wt. %. Alkali hydroxide is added to the reaction mixture in an amount sufficient to achieve pH greater than about 4.5. The reaction mixture is then stirred in a reactor for a sufficient amount of time to achieve conversion of BZS to zirconium oxide, e.g., from about 30 min to about 2 hours. An ambient temperature is typically sufficient to drive the reaction between the BZS and the alkali hydroxide. Optionally, the reaction mixture can be heated to a temperature from about 40° C. to about 80° C. Using NaOH as an example, the following reaction may take place between BZS and NaOH in 751:

$$Zr(SO_4)_2 + 2NaOH = ZrO(SO_4) + Na_2SO_4 + H_2O,$$

where $ZrO(SO_4)$ is an exemplary intermediate HZO compound. This compound is a zirconium oxide sulfate (having sulfate as a counteranion). In 752, the reaction mixture containing intermediate HZO is filtered off to yield a crude product. A vacuum drum filer or any other suitable filter can be used to separate HZO intermediate and the filtrate in this step. Filtrate in 752 may contain excess alkali hydroxide, alkali sulfate, sulfuric acid, and various other water-soluble impurities. In 753, the crude intermediate may be washed with water. For example, the crude solid HZO may be slurried in a vessel and stirred using a mechanical agitator until concentration of various solutes in the aqueous phase of the slurry remains constant (e.g., no longer increase with time). Then, the slurry is filtered using a drum filter and the process is repeated several times, e.g., 2, 3, or 4 times. In some implementations, each wash pass takes from about 1 hour to about 2 hours. In some embodiments, the intermediate HZO is washed 3 times and each pass takes about 1 hour. In 754, the solid HZO intermediate is mixed with an aqueous solution of alkali hydroxide (e.g., NaOH) to obtain a second reaction mixture. Typically, 50 wt. % alkali hydroxide solution is used in the second reaction. An amount of alkali hydroxide in the second reaction mixture is sufficient to achieve pH of greater than about 12.5. The process may be carried out as described previously for the first reaction in 751 (e.g., the second reaction may occur at room temperature of at an elevated temperature). Using NaOH as an example, the following reaction may take place between zirconium oxide sulfate and NaOH in 754:

$$ZrO(SO_4)+2NaOH=ZrO_2+Na_2SO_4+H_2O.$$

Upon completion of the second reaction (e.g., from about 30 min to about 2 hours), the reaction mixture is filtered off in 755 to yield a crude HZO product, which may be further washed with water in 756 as described here for the intermediate HZO product. In order to obtain HZOCl, the washed HZO is mixed with an aqueous solution of HCl in 757 to obtain a third reaction mixture. Exemplary concentration of HCl in the solution may be from about 0.1M to about 12M (e.g., about 0.5M or about 1M). HCl is added to the reaction mixture in an amount sufficient to achieve pH of about 7 (e.g., 6.9-7.1). The reaction mixture is then stirred in a reactor for a sufficient amount of time to achieve conversion of zirconium oxide to HZOCl, e.g., from about 30 min to about 2 hours. An ambient temperature is typically sufficient to drive this reaction. However, the reaction mixture can be heated to a temperature from about 40° C. to about 80° C. The following reaction may take place between HZO and HCl in 757:

$$ZrO_2+HCl=ZrO_2 \times HCl.$$

The third reaction mixture (slurry) is further filtered in 758 to obtain a crude HZOCl product, and the crude product may be washed with water in 759, for example, as described previously for washing crude HZO in 756. In some implementations, the HZOCl product is washed with water once for about 1 hour. In 760, the wet washed solid product can be dewatered using a centrifuge and dried (e.g., in a tray drier), for example, to a LOD of about 12% to about 40% (e.g., about 14-18% LOD). The process of preparing HZOCl can be carried out using conventional industrial equipment, for example, as described here for the preparation of AlkZP (e.g., reactors, agitators, mixers, pumps, funnels, centrifuges, filters, and driers).

Figure 31:
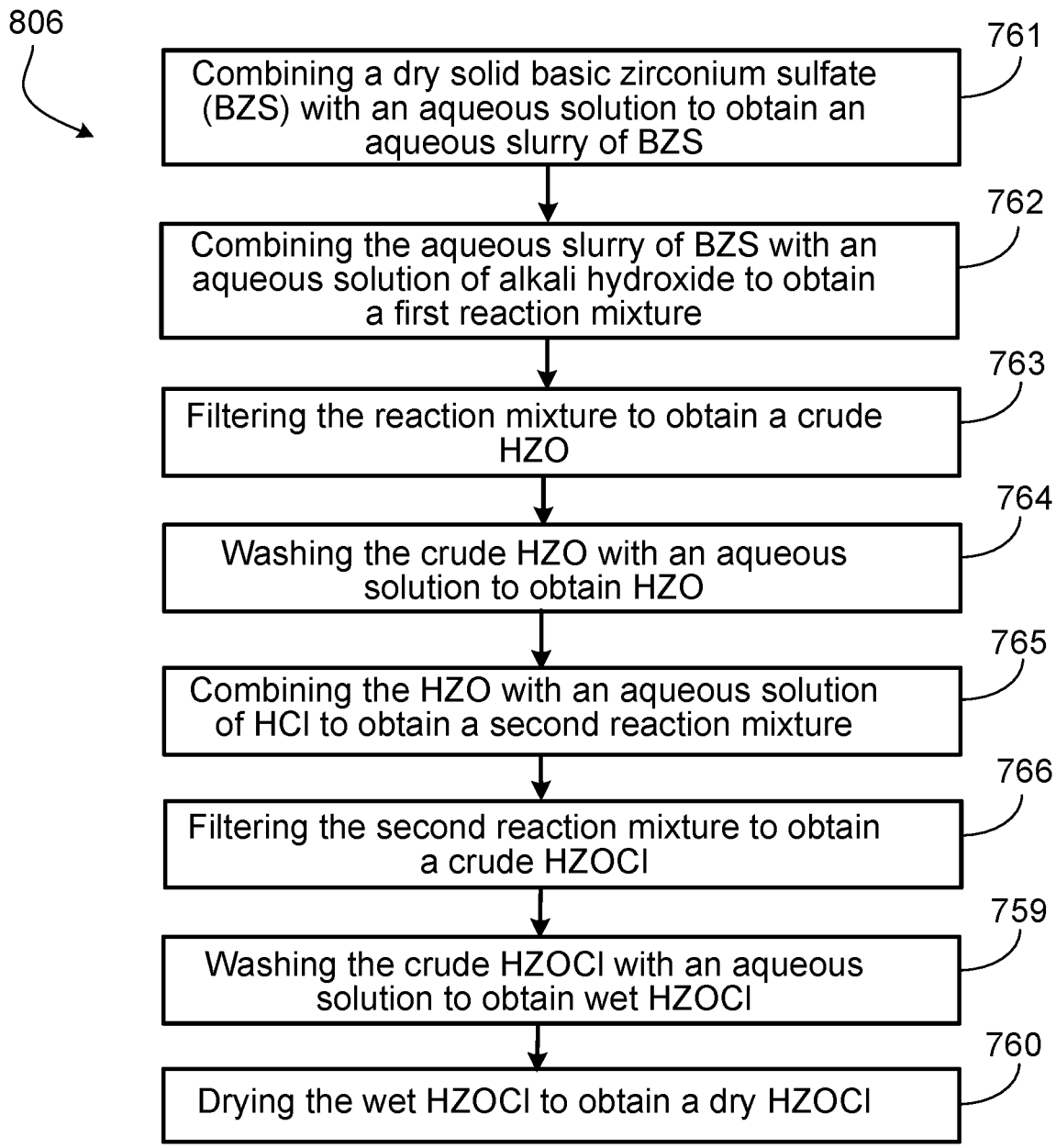
FIG. 31 contains a flow-chart for an exemplary method of making hydrous zirconium oxide with chloride counterion, which includes a single step of treating zirconium sulfate with an alkali hydroxide.

The HZOCl material obtained as described in the process 804 possesses the desirable characteristics of a phosphate adsorbent. For example, the $PO_4^-$ adsorption for the HZOCl material is from about 40 mg/g to about 50 mg/g (e.g., about 45 mg/g). However, the process requires two separate alkali hydroxide treatments, and eight wash passes, thereby greatly increasing the cost of the phosphate adsorbent material being produced. It was unexpectedly found that the HZOCl material with similar $PO_4^-$ adsorbent characteristics (from about 40 mg/g to about 50 mg/g, or about 45 mg/g) can be prepared from BZS using only one alkali hydroxide treatment step. Eliminating the step of second alkali hydroxide treatment eliminates three of the eight wash passes, reduces the process time and the amount of water used, and therefore reduces the overall cost of the cartridge adsorbent material. The improved process can be described as follows. Referring to FIG. 31, in 761, basic zirconium sulfate is combined with an aqueous solution to yield an aqueous slurry, having a density of, for example, from about 1 mL to about 6 mL of water per 1 g of solid BZS. In 751, the aqueous slurry of BZS is combined with an aqueous solution of an alkali hydroxide (e.g., NaOH) to obtain a reaction mixture. Exemplary concentration of alkali hydroxide in the solution may be from about 5 wt. % to about 50 wt. %. Alkali hydroxide is added to the reaction mixture in an amount sufficient to achieve pH greater than about 12.5. The reaction mixture is then stirred in a reactor for a sufficient amount of time to achieve conversion of BZS to zirconium oxide, e.g., from about 30 min to about 4 hours. An ambient temperature is typically sufficient to drive the reaction between the BZS and the alkali hydroxide to obtain HZO. Optionally, the reaction mixture can be heated to a temperature from about 40° C. to about 80° C. Using NaOH as an example, the following reaction may take place between BZS and NaOH in 762:

$$Zr(SO_4)_2+4NaOH=ZrO_2+4Na_2SO_4+2H_2O.$$

The crude zirconium oxide from the reaction mixture is filtered off in 763, e.g., using a vacuum drum filter, and then washed with water in 764 to obtain pure wet HZO. The washing phase may be repeated as necessary, until no more excess alkali hydroxide remains in the filtrate. In some implementations, the crude HZO is washed four times before reacting with HCl in 765. To obtain HZOCl, wet HZO is combined with an aqueous solution of HCl, having a concentration from about 0.1M to about 12M (e.g., about 0.5M or about 1M). HCl is added to the reaction mixture in an amount sufficient to achieve pH between about 6 and about 7. The reaction mixture is then stirred in a reactor for a sufficient amount of time to achieve conversion of zirconium oxide to HZOCl, e.g., from about 30 min to about 4 hours. An ambient temperature is typically sufficient to drive this reaction. However, the reaction mixture can be heated to a temperature from about 40° C. to about 80° C. To isolate and obtain dry HZOCl product, the reaction mixture can be worked up in 759, 760 as described previously for the conventional process.

In some implementations, the sorbent cartridge assembly includes a housing containing the sorbent cartridge 303. In some embodiments, the cartridge 303 is disposable. The cartridge can, for example, be constructed such that it can be removed from the housing after use and disposed of when there is a decrease in the dialysate regeneration efficiency of the cartridge (e.g., through layer saturation) or the cartridge becomes worn or damaged. The cartridge could then be replaced with a similar cartridge for a subsequent use of the dialysate system 301.

In certain embodiments, the sorbent cartridge 303 includes hollow fibers. The hollow fibers can reject positively charged ions, as well as increase the capacity of the cartridge. The hollow fibers can be coated with an ion-rejecting material, which through a water-purification like mechanism allows the urea through but rejects positively charged ions such as calcium and magnesium. The material coating the hollow fibers can be any such material known to one of skill in the art (e.g., fatty acids or polymer chains like polysulfone) that can effectively reject calcium and magnesium and therefore retain those ions in the dialysis solution The clean ("regenerated") dialysate flows out of the sorbent cartridge 303 and into the fluid line 313, past the ammonia sensor NH, and into the primary reservoir 304. In some cases, a volume of the regenerated dialysate within the primary reservoir 304 exceeds a capacity of the primary reservoir 304 and therefore flows through a fluid line 327 into the secondary reservoir 305, which remains in fluid communication with the primary reservoir 304 throughout the treatment stage. Pump P2 pumps regenerated dialysate out of the primary reservoir 304, into the fluid line 314, and into pump P2.

While the regenerated dialysate exiting the sorbent cartridge 303 has been stripped of toxic substances that were absorbed from the patient's blood in the dialysis system 301, the regenerated dialysate must be further conditioned to meet acceptable physiological properties before being circulated back into the dialyzer 337 of the dialysis system 301 as fresh dialysate. Over time, the sorbent cartridge 303 changes a composition of the regenerated dialysate exiting the sorbent cartridge 303 during the first phase of the treatment stage (e.g., an early, initial phase in which the patient's blood is initially circulated through the dialysis machine 301). For example, during the initial phase, levels of toxic substances (e.g., ammonia) within the spent dialysate entering the sorbent cartridge 303 are relatively high. Hence, at this phase, the sorbent cartridge 303 releases relatively high levels of hydrogen cations, sodium cations and other cations into the dialysate, leading to high conductivity and low pH of the regenerated dialysate exiting the cartridge. However, as the initial phase of the treatment progresses, spent dialysate entering the sorbent cartridge 303 contains fewer toxic substances (e.g., ammonia), and the cartridge releases less hydrogen and sodium cations leading to lower conductivity and higher pH of the "clean" dialysate as compared to the regenerated dialysate at an earlier point in time.

Accordingly, pump P4 continues to pump the electrolyte solution out of the bag 306 and into the fluid line 320, through ports (a) and (c) of valve V6, into an upper segment of the fluid line 319, through pump P4, and into the fluid line 314 at a flow rate that depends on (e.g., is a fraction of) the flow rate at which pump P2 pumps dialysate. Thus, pumps P2 and P4 together form a closed pump control loop 332 that governs the flow rate at which pump P4 pumps the electrolyte solution, which is in a range of about 0.5 mL/min to about 5 mL/min. Furthermore, pump P3 continues to pump either the bicarbonate solution out of the bag 309 or the dilution water out of the bag 308, through port (c) of valve V5, into an upper segment of the fluid line 317, through pump P3, and into the fluid line 314 to further condition the dialysate.

As the dialysate passes through pump P2 and conductivity sensor CT1, the conductivity sensor CT1 detects a conductivity of the dialysate. Based on continuous measurements of the conductivity of the dialysate, either the bicarbonate solution or the dilution water will be continuously selected for addition to the dialysate through port (c) of valve V5, and the flow rate at which pump P3 pumps dialysate will be continuously adjusted to maintain a conductivity of the dialysate within a physiologically acceptable range of 13.5 mS/cm to 14.2 mS/cm. Generally, as a difference between the measured conductivity and an acceptable conductivity increases, the flow rate at which the pump P3 pumps fluid increases. Accordingly, as the difference between the measured conductivity and the acceptable conductivity decreases, the flow rate at which the pump P3 pumps fluid decreases. In this manner, the conductivity meter CT1 and the pump P3 together form a closed pump control loop 331 that regulates a flow rate at which the pump P3 pumps fluid. If the conductivity of the dialysate is too low during the first phase of the treatment stage, then bicarbonate solution is infused into the dialysate to raise the conductivity.

After passing the conductivity sensor CT1, the dialysate flows past the heat exchanger HX and temperature sensor T2. Based on a fluid temperature detected by temperature sensor T2, a power level of the heat exchanger HX will be adjusted to maintain the temperature of the dialysate at the set point temperature of the heat exchanger HX. In this way, temperature sensor T2 and heat exchanger HX form a closed heater control loop 333. The dialysate flows from the fluid line 315 through ports (c) and (b) of valve V2 into the fluid line 323 and past conductivity sensor CT2. As the dialysate passes conductivity sensor CT2, conductivity sensor CT2 performs a second check (e.g., downstream of heat exchanger HX) to detect a conductivity of the dialysate.

If the conductivity of the dialysate is outside of the acceptable range (e.g., either too low or too high), but within a predetermined range (e.g., that is broader than the acceptable range), then a safety system in electrical communication with the conductivity sensor will adjust a flow rate of infusion of the bicarbonate solution or the dilution water to achieve a conductivity within the acceptable range. If the conductivity level of the dialysate is outside of the predetermined physiologically safe range, then, in some implementations, the fluid conditioning system 100 will attempt to restore the safe fluid parameters and continue the treatment. For example, valves V3 and V4 will adjust to direct fluid through the bypass fluid line 336 and close fluid lines 324 and 325 until a time at which the conductivity has again stably reached a physiologically safe range, at which time valves V3, V4 will adjust to close the bypass fluid line 336 and direct fluid to and from the dialysis system 301 via fluid lines 324 and 325. In some implementations, a user may also be instructed to check that fluid levels of the bicarbonate solution and the dilution water are non-zero upon return of the conductivity to a physiologically safe range.

Once the conductivity of the regenerated ("clean") dialysate reaches a predetermined value in a range of about 13.8 mS/cm to about 14.0 mS/cm and remains at that level without infusion of the bicarbonate solution to regulate the conductivity of the dialysate, the first phase of the treatment stage concludes, and the second phase of the treatment stage begins.

During the second (e.g., later, final) phase of the treatment stage, bicarbonate is no longer used to regulate (e.g., increase) the conductivity of the dialysate, and dilution water is the sole substance at valve V5 that is used to regulate (e.g., decrease) the conductivity of the dialysate until the end of the treatment stage (e.g., the end of the second phase). Accordingly, port (b) of valve V5 is closed, while port (a) of valve V5 is opened. If the conductivity of the dialysate is too high during the second phase of the treatment stage, then dilution water is infused into the dialysate to lower the conductivity of the dialysate.

Over the course of the second phase of the treatment stage, an amount of ammonium captured in the sorbent cartridge 303 increases, such that a capacity of the sorbent cartridge 303 to absorb additional ammonium gradually decreases, and a level of ammonia and ammonium salts within the regenerated dialysate eventually increases, once the capacity of the sorbent to adsorb ammonium is exhausted. The ammonia sensor NH detects the level of ammonia within the regenerated dialysate at a location downstream of the sorbent cartridge 303.

The treatment stage (e.g., including both the first and second phases) typically lasts a duration of about 120 min to about 300 min. For example, 240 minutes (e.g., 4 hours) is a standard duration that typically achieves adequate treatment for the vast majority of patients. Furthermore, most treatment stages will end after four hours without reaching a threshold ammonium concentration of 2 mg/dL (e.g., without ever approaching exhaustion of the filtering capabilities of the sorbent cartridge 303). The fluid conditioning system 100 will sound an audio alert signifying that the treatment completed successfully and that the patient can disconnect himself or herself from the dialyzer 337. However, if the ammonium level in the dialysate (e.g., as detected by the ammonia sensor NH) indicates that the sorbent cartridge 303 is no longer absorbing enough ammonium from the spent dialysate to maintain the ammonium level at or below an acceptable value of about 2 mg/dL prior to the standard treatment duration, then the treatment stage will conclude prematurely. Such conditions may occur occasionally for larger patients that have very high blood urea nitrogen (BUN) levels.

In some embodiments, the ammonia sensor 165 and the cooperating ammonia detector 121 together provide an ammonia detection system 700 of the fluid conditioning system 100, as illustrated in FIG. 26. As discussed above with respect to FIGS. 18 and 19, the sorbent cartridge 303 is designed to regenerate spent dialysate that circulates through the fluid circuit 350. The spent dialysate contains urea that has diffused across the dialyzer 337 from the patient's blood, and ammonium is produced within the dialysate as a result of urea decomposition within the sorbent cartridge 303. The sorbent cartridge 303 is therefore designed to remove ammonium as part of the process of regenerating the spent dialysate. Ammonium that is not removed from the dialysate within the sorbent cartridge 303 can generate ammonia within the circulating dialysate. Therefore, the ammonia detection system 700 is positioned downstream of the sorbent cartridge 303 (e.g., but upstream of the primary reservoir 304, shown in FIG. 18) for determining whether an ammonium level within the regenerated dialysate that exits the sorbent cartridge 303 is within an acceptable range.

Ammonium, by itself, may not pose a direct health threat to the patient. However, the ammonium transferred to the patient (e.g., into the patient's blood) through the dialyzer 337 can generate ammonia (e.g., ammonia gas) either in the fluid circuit 350 or in the patient's blood, and ammonia is toxic above a certain threshold concentration (e.g., about 100 μg/dL). Depending on a pH and a temperature of the dialysate within the fluid circuit 350, trace amounts of ammonia gas are generated within the dialysate from the ammonium present in the dialysate. Therefore, the ammonia detection system 700 is positioned just downstream of sorbent cartridge 303 in order to identify ammonium leakage in the dialysate and thereby protect the patient from overexposure to ammonia.

Once the treatment stage concludes, the fluid circuit 350 can be drained of spent dialysate, and the spent dialysate can be disposed of as waste. In some examples, the bags 306, 307, 308, and 309 and the various fluid lines can be manually removed and discarded while still containing dialysate. In some examples, the patient may disconnect from the dialysis system 301 and drain the fluid lines 323 and 326 to a waste receptacle to empty the various components of the fluid conditioning system 100. In some examples, the fluid conditioning system 100 may be operated to run either or both of pumps P1 and P2 in a forward direction or a reverse direction to drain any of the bags 306, 307, 308, 309, the sorbent cartridge 303, the prime tank 302, the primary reservoir 304, and the secondary reservoir 305. In some examples, the fluid conditioning system 100 may be operated to run pumps P4 and P3 in a forward direction to drain the bags 306, 307, 308, and 309. In some examples, such operation of pumps P4, P3 may be carried out based on readings at conductivity meter CT1. For example, upon detection of a sufficiently low threshold conductivity, the electrolyte bag 306 may be assumed to have been emptied, such that a next bag or fluid line can be drained.

Throughout the fluid conditioning cycle, pressure transducers PT1, PT2, PT3, and PT4 detect fluid pressures to regulate pump flow rates. For example, during all stages (e.g., the priming, infusion, and treatment stages) of the fluid conditioning cycle, pressure transducer PT1 forms a closed pump control loop 328 with pump P1 by detecting a fluid pressure of the dialysate within the fluid line 312 (e.g., located downstream of pump P1) and providing a feedback signal to pump P1 indicative of the fluid pressure. Based on the fluid pressure of the dialysate, an angular speed (e.g., an RPM level) of pump P1 is adjusted to maintain the flow rate within a desired range. During the treatment stage of the fluid conditioning cycle, pressure transducer PT4 forms an additional closed pump control loop 329 with pump P1 by detecting a fluid pressure of the dialysate exiting the dialysis system 301 (e.g., upstream of pump P1) and providing a forward signal to pump P1 indicative of the fluid pressure. Based on the fluid pressure of the dialysate, the angular speed of pump P1 is adjusted to closely match the flow rate at pump P1 with that of the dialysate exiting the dialysis system 301. Accordingly, the fluid pressure of the dialysate within the fluid line 312 (e.g., downstream of pump P1) is at least in part affected by the fluid pressure of the dialysate exiting the dialysis system 301 (e.g., upstream of pump P1).

Similarly, during all stages (e.g., the priming, infusion, and treatment stages) of the fluid conditioning cycle, pressure transducer PT2 forms a closed pump control loop 330 with pump P2 by detecting a fluid pressure of the dialysate within the fluid line 315 (e.g., located downstream of pump P2) and providing a feedback signal to pump P2 indicative of the fluid pressure. Based on the fluid pressure of the dialysate, an angular speed of pump P2 is adjusted to maintain the flow rate within a desired range. During the treatment stage of the fluid conditioning cycle, the flow rate at which pump P3 pumps fluid is regulated by a feedback signal from conductivity meter CT1 to form the pump control loop 331, and the flow rate at which pump P4 pumps the electrolyte solution is regulated by a feedback signal from pump P2 to form the pump control loop 332, as discussed above.

During all stages of the fluid conditioning cycle, pressure transducers PT3 and PT4 detect operation of the dialyzer 337. If measurements at pressure transducers PT3 and PT4 indicate that there is no fluid flow through the dialyzer 337, then the fluid conditioning system 100 will enter the bypass mode to flow dialysate through fluid line 336 and to avoid delivering dialysate to the dialysis system 301 via fluid lines 324, 325.

Figure 23:
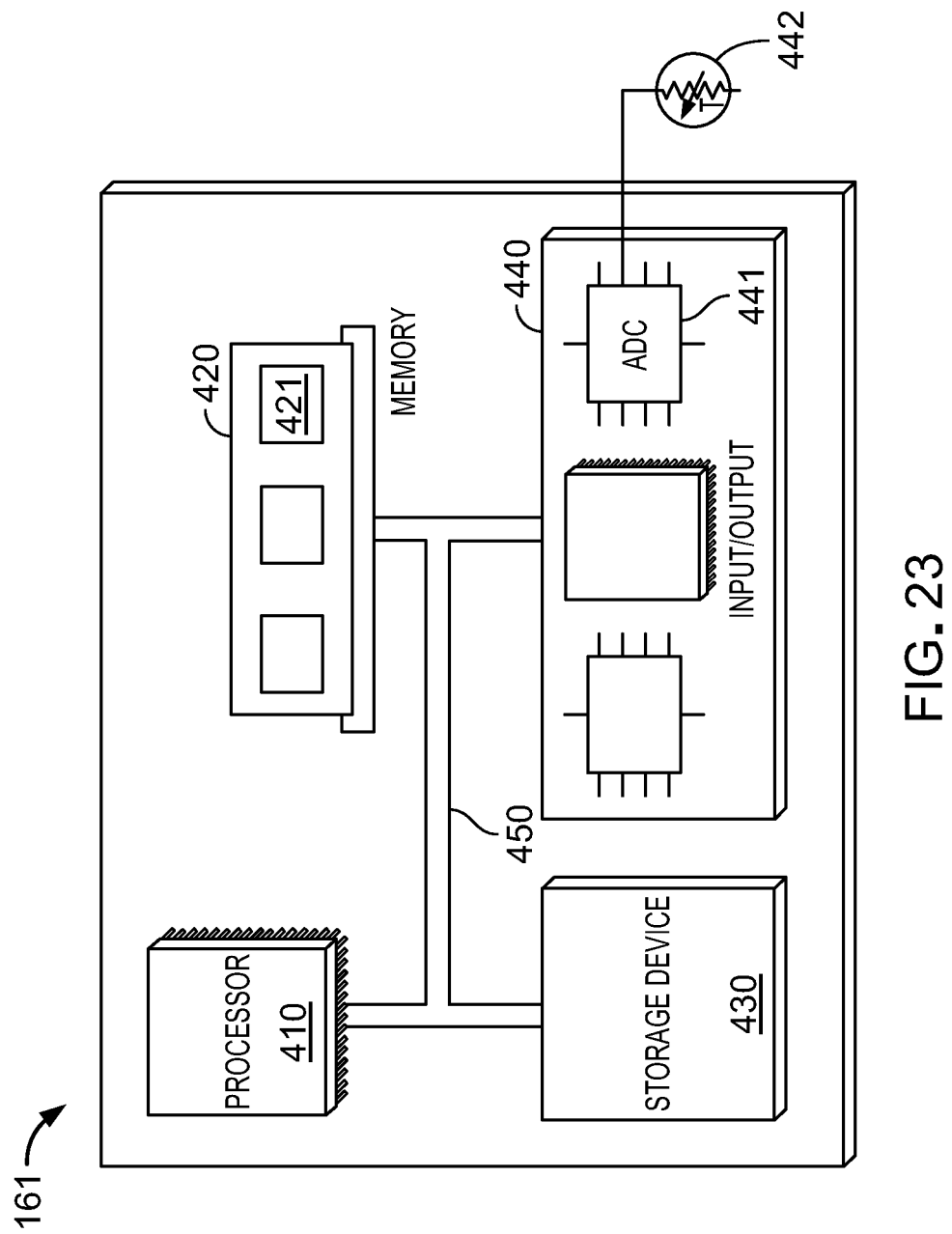
FIG. 23 provides a block diagram of a control system of the fluid conditioning system of FIG. 1.

FIG. 23 provides a block diagram of the control system 161. The control system 161 includes a processor 410, a memory 420, a storage device 430, and an input/output interface 440. In some embodiments, the control system 161 includes more than one processor 410, memory 420, storage device 430, and/or input/output interface 440. Each of the components 410, 420, 430, and 440 can be interconnected, for example, using a system bus 450. The processor 410 is capable of processing instructions for execution within the control system 161. The processor 410 can be a single-threaded processor, a multi-threaded processor, or a quantum computer. The processor 410 is capable of processing instructions stored in the memory 420 or on the storage device 430.

The memory 420 stores information within the control system 161. In some implementations, the memory 420 is a computer-readable medium. The memory 420 can, for example, be a volatile memory unit or a non-volatile memory unit. The storage device 430 is capable of providing mass storage for the control system 139. In some implementations, the storage device 430 is a non-transitory computer-readable medium. The storage device 430 can include, for example, a hard disk device, an optical disk device, a solid-state drive, a flash drive, magnetic tape, or some other large capacity storage device. The storage device 430 may alternatively be a cloud storage device, e.g., a logical storage device including multiple physical storage devices distributed on a network and accessed using a network.

The input/output interface 440 provides input/output operations for the control system 161. In some implementations, the input/output interface 440 includes one or more of network interface devices (e.g., an Ethernet card), a serial communication device (e.g., an RS-232 10 port), and/or a wireless interface device (e.g., an 802.11 card, a 3G wireless modem, or a 4G wireless modem). In some implementations, the input/output device includes driver devices configured to receive input data and send output data to other input/output devices, e.g., keyboard, printer and display devices (e.g., the display screen 148). In some implementations, mobile computing devices, mobile communication devices, and other devices are used.

In some implementations, the input/output interface 440 includes at least one analog-to-digital converter 441. An analog-to-digital converter converts analog signals to digital signals, e.g., digital signals suitable for processing by the processor 410. In some implementations, one or more sensing elements are in communication with the analog-to-digital converter 441, as will be discussed in more detail below.

In some implementations, the control system 161 is a microcontroller. A microcontroller is a device that contains multiple elements of a computer system in a single electronics package. For example, the single electronics package could contain the processor 410, the memory 420, the storage device 430, and input/output interfaces 440.

FIGS. 24 and 25 provide block diagrams of a hardware system 500 and a software system 600 of the fluid conditioning system 100 that are provided by the control system 161. As shown in FIG. 24, the hardware system 500 is provided by a circuit board for generating GUIs for display on the display screen 148 and one or more circuit boards 135 for controlling the electromechanical peripheral components of the fluid conditioning system 100, and the various electromechanical peripheral components. The software system 600 can be broken down into an external view 610, an application layer 620, and a driver layer 630. The external view 610 includes user interfaces provided by the GUIs, lights, sounds, and debug ports. The application layer 620 includes business logic, and the driver layer 630 is configured to implement peripheral-specific code (e.g., communication protocols and stepper motor drivers).

Although the example control system 161, the example hardware system 500, and the example software system 600 have been described respectively in FIGS. 23-25, implementations of the subject matter and the functional operations described above can be implemented in other types of digital electronic circuitry, or in computer software, firmware, or hardware, including the structures disclosed in this specification and their structural equivalents, or in combinations of one or more of them.

A number of embodiments have been described in detail above. However, various modifications to these embodiments may be made without departing from the spirit and scope of the above disclosures. For example, while the fluid conditioning system 100 has been described and illustrated as including the pressure transducers 119 (PT1, PT2, PT3, PT4) for regulating pump flow rates, in some embodiments, a fluid conditioning system that is otherwise similar in construction and function to the fluid conditioning system 100 may alternatively include flow meters instead of pressure transducers for regulating pump flow rates. In some embodiments, a fluid conditioning system that is otherwise similar in construction and function to the fluid conditioning system 100 may not include pressure transducers or flow meters and may instead be RPM-controlled based on a detailed knowledge of the system operation to regulate pump flow rates.

While the fluid conditioning system 100 has been described and illustrated as including peristaltic pumps 103, 104 (P1, P2, P3, P4), in some embodiments, a fluid conditioning system that is otherwise similar in construction and function to the fluid conditioning system 100 may alternatively include a different type of pump, such as an impeller pump, a linear displacement pump, positive displacement pump, or a centrifugal pump.

While the fluid conditioning system 100 has been described and illustrated as including one overflow reservoir (e.g., the secondary reservoir 305), in some embodiments, a fluid conditioning system that is otherwise similar in construction and function to the fluid conditioning system 100 may include one or more additional overflow reservoirs. For example, in some embodiments, an additional reservoir may be connected to the fluid circuit 350 upstream of pump P1 or downstream of pump P2. In some embodiments, an additional reservoir may have a capacity different than that of either reservoir 304 or reservoir 305 or may have a zero volume capacity. In some embodiments, a reservoir may be permanently connected to a drain.

While the heater bag 153 has been described and illustrated as being arranged downstream of pump P2 of the fluid conditioning system 100, in some embodiments, a fluid conditioning system that is otherwise similar in construction and function to the fluid conditioning system 100 may include a heater bag or other heating element that is arranged at a different location along the fluid circuit 350 in order to achieve optimal temperature control of fluid flowing through the fluid circuit 350. For example, in some embodiments, a heater bag may be positioned immediately downstream of the sorbent cartridge 303 and may be powered based on signals from temperature sensor T1 to ensure that the temperature of the dialysis fluid is not high enough to damage internal components of the sorbent cartridge 303. In some embodiments, a heater bag may be located along the fluid circuit 350 anywhere between valve V1 and valve V2, as advantageous (e.g., to promote dissolution of the dry chemicals in the supply bags 306, 307, 309).

While the fluid conditioning system 100 has been described as including three-way valves V1-V7, in some embodiments, a fluid conditioning system that is otherwise similar in construction and function to the fluid conditioning system 100 may alternatively include one or more two-way valves to achieve the fluid flow path scenarios discussed above.

While an operation of the fluid conditioning system 100 has been described and illustrated with respect to certain flow rates, fluid volumes, temperatures, pressures, and time periods, in some embodiments, the fluid conditioning system 100 may be operated to carry out a fluid conditioning cycle with one or more different flow rates, fluid volumes, temperatures, pressures, and time periods, while still functioning to adequately condition dialysate for use in a cooperating dialysis system.

Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

Exemplary Enumerated Embodiments

1. A sorbent cartridge device, comprising:
an ion-exchange material comprising zirconium phosphate,
wherein the device comprises less than about 0.1 mg of leachable phosphate ions per about 1 g of the ion-exchange material.

2. The device of embodiment 1, comprising from about 0.01 mg to about 0.03 mg of leachable phosphate ions per about 1 g of the ion-exchange material.

3. The device of embodiment 1, further comprising a phosphate-adsorbing material comprising a zirconium oxide.

4. The device of embodiment 3, wherein the weight ratio between the zirconium phosphate and the zirconium oxide in the device is from about 10:1 to about 40:1.

5. The device of embodiment 3, comprising a homogenous mixture of the zirconium phosphate and the zirconium oxide.

6. The device of embodiment 3, comprising a layer of the zirconium phosphate and a layer of the zirconium oxide.

7. The device of embodiment 1, further comprising a urea-decomposing material.

8. The device of embodiment 7, wherein the urea-decomposing material is a urease enzyme.

9. The device of embodiment 7, further comprising alumina.

10. The device of embodiment 1, wherein the zirconium phosphate comprises an alkaline zirconium phosphate.

11. The device of embodiment 10, wherein the alkaline zirconium phosphate is prepared by a process comprising:
drying an acid zirconium phosphate to obtain a dry acid zirconium phosphate;
combining the dry acid zirconium phosphate with an aqueous solution to obtain an aqueous slurry of the acid zirconium phosphate; and
combining the slurry with an alkali hydroxide to obtain the alkaline zirconium phosphate.

12. The device of embodiment 1, comprising:
sodium content of about 60 mg to about 100 mg per about 1 g of the ion-exchange material;
ammonia or ammonium adsorption capacity of about 15 mg to about 20 mg per about 1 g of the ion-exchange material; and
a weight ratio of P to Zr from about 1.5:1 to about 2:1.

13. A dialysis system comprising:
a dialysate generation machine;
a pump adapted to move fluid through the dialysate generation machine; and
a sorbent cartridge device fluidically connected to the dialysate generation machine, wherein
the device comprises an ion-exchange material comprising zirconium phosphate and less than about 0.1 mg of leachable phosphate ions per about 1 g of the ion-exchange material.

14. The system of embodiment 13, wherein the device comprises from about 0.01 mg to about 0.03 mg of leachable phosphate ions per about 1 g of the ion-exchange material.

15. The system of embodiment 13, wherein the device comprises a phosphate-adsorbing material comprising a zirconium oxide.

16. The system of embodiment 15, wherein the weight ratio between the zirconium phosphate and the zirconium oxide in the device is from about 10:1 to about 40:1.

17. The system of embodiment 13, wherein the device comprises a urea-decomposing material.

18. The system of embodiment 13, wherein the zirconium phosphate comprises an alkaline zirconium phosphate.

19. A method of removing one or more substances from a spent dialysis solution, the method comprising passing the spent dialysis solution through a sorbent cartridge device comprising an ion-exchange material comprising zirconium phosphate,
wherein the device comprises less than about 0.1 mg of leachable phosphate ions per about 1 g of the ion-exchange material.

20. The method of embodiment 19, the one or more substances comprise ammonia or ammonium.

Other embodiments are within the scope of the following claims.

What is claimed is:

1. A sorbent cartridge device, comprising:
an ion-exchange material comprising zirconium phosphate,
wherein the device comprises less than about 0.1 mg of leachable phosphate ions per about 1 g of the ion-exchange material, and
weight ratio of P to Zr in the ion-exchange material is from about 1.5:1 to about 2:1.

2. The device of claim 1, comprising from about 0.01 mg to about 0.03 mg of leachable phosphate ions per about 1 g of the ion-exchange material.

3. The device of claim 1, further comprising a phosphate-adsorbing material comprising a zirconium oxide.

4. The device of claim 3, wherein the weight ratio between the zirconium phosphate and the zirconium oxide in the device is from about 10:1 to about 40:1.

5. The device of claim 3, comprising a homogenous mixture of the zirconium phosphate and the zirconium oxide.

6. The device of claim 3, comprising a layer of the zirconium phosphate and a layer of the zirconium oxide.

7. The device of claim 1, further comprising a urea-decomposing material.

8. The device of claim 7, wherein the urea-decomposing material is a urease enzyme.

9. The device of claim 7, further comprising alumina.

10. The device of claim 1, wherein the zirconium phosphate comprises an alkaline zirconium phosphate.

11. The device of claim 10, wherein the alkaline zirconium phosphate is prepared by a process comprising:
drying an acid zirconium phosphate to obtain a dry acid zirconium phosphate;
combining the dry acid zirconium phosphate with an aqueous solution to obtain an aqueous slurry of the acid zirconium phosphate; and
combining the slurry with an alkali hydroxide to obtain the alkaline zirconium phosphate.

12. The device of claim 1, comprising:
sodium content of about 60 mg to about 100 mg per about 1 g of the ion-exchange material;
ammonia or ammonium adsorption capacity of about 15 mg to about 20 mg per about 1 g of the ion-exchange material.

13. A dialysis system comprising:
a dialysate generation machine;
a pump adapted to move fluid through the dialysate generation machine; and
a sorbent cartridge device fluidically connected to the dialysate generation machine, wherein
the device comprises an ion-exchange material comprising zirconium phosphate and less than about 0.1 mg of leachable phosphate ions per about 1 g of the ion-exchange material, wherein weight ratio of P to Zr in the ion-exchange material is from about 1.5:1 to about 2:1.

14. The system of claim 13, wherein the device comprises from about 0.01 mg to about 0.03 mg of leachable phosphate ions per about 1 g of the ion-exchange material.

15. The system of claim 13, wherein the device comprises a phosphate-adsorbing material comprising a zirconium oxide.

16. The system of claim 15, wherein the weight ratio between the zirconium phosphate and the zirconium oxide in the device is from about 10:1 to about 40:1.

17. The system of claim 13, wherein the device comprises a urea-decomposing material.

18. The system of claim 13, wherein the zirconium phosphate comprises an alkaline zirconium phosphate.

19. A method of removing one or more substances from a spent dialysis solution, the method comprising passing the spent dialysis solution through a sorbent cartridge device comprising an ion-exchange material comprising zirconium phosphate,
wherein the device comprises less than about 0.1 mg of leachable phosphate ions per about 1 g of the ion-exchange material and wherein weight ratio of P to Zr in the ion-exchange material is from about 1.5:1 to about 2:1.

20. The method of claim 19, the one or more substances comprise ammonia or ammonium.

* * * * *